(12) United States Patent
Kosugi et al.

(10) Patent No.: US 11,311,462 B2
(45) Date of Patent: Apr. 26, 2022

(54) ADHESIVE MONOMERS FOR DENTAL MATERIALS

(71) Applicants: Mitsui Chemicals, Inc., Tokyo (JP); KULZER GMBH, Hanau (DE)

(72) Inventors: Yoko Kosugi, Ichihara (JP); Akiko Matsumoto, Narashino (JP); Kazuhiko Yoshinaga, Ichihara (JP); Michael Gerlach, Hofheim (DE); Maria Lechmann-Dorn, Frankfurt (DE); Jutta Schneider, Runkel (DE); Andreas Utterodt, Neu-Anspach (DE)

(73) Assignees: MITSUI CHEMICALS, INC., Tokyo (JP); KULZER GMBH, Hanau (DE)

( * ) Notice: Subject to any disclaimer, the term of this patent is extended or adjusted under 35 U.S.C. 154(b) by 385 days.

(21) Appl. No.: 16/488,299

(22) PCT Filed: Mar. 29, 2018

(86) PCT No.: PCT/JP2018/013232
§ 371 (c)(1),
(2) Date: Aug. 23, 2019

(87) PCT Pub. No.: WO2018/181707
PCT Pub. Date: Oct. 4, 2018

(65) Prior Publication Data
US 2019/0374440 A1 Dec. 12, 2019

(30) Foreign Application Priority Data
Mar. 31, 2017 (JP) .............................. JP2017-072681

(51) Int. Cl.
| A61K 6/60 | (2020.01) |
| A61K 6/30 | (2020.01) |
| A61K 6/74 | (2020.01) |
| A61K 6/838 | (2020.01) |
| C08F 20/36 | (2006.01) |

(52) U.S. Cl.
CPC ............... *A61K 6/60* (2020.01); *A61K 6/30* (2020.01); *A61K 6/74* (2020.01); *A61K 6/838* (2020.01); *C08F 20/36* (2013.01)

(58) Field of Classification Search
CPC combination set(s) only.
See application file for complete search history.

(56) References Cited

U.S. PATENT DOCUMENTS

| 4,539,382 A | 9/1985 | Omura et al. |
| 4,612,384 A | 9/1986 | Omura et al. |
| 4,650,847 A | 3/1987 | Omura et al. |
| 4,663,184 A | 5/1987 | Hegel |
| 9,987,199 B2 | 6/2018 | Inaki et al. |
| 2009/0043009 A1 | 2/2009 | Sang |
| 2013/0047887 A1* | 2/2013 | Trujillo-Lemon ..... A61K 6/887 106/35 |
| 2014/0296364 A1* | 10/2014 | Moszner ................ A61K 6/30 522/171 |
| 2015/0190313 A1 | 7/2015 | Inaki et al. |
| 2017/0020791 A1 | 1/2017 | Moszner et al. |
| 2019/0374440 A1* | 12/2019 | Kosugi .................... A61K 6/30 |
| 2019/0374441 A1* | 12/2019 | Kosugi ................ C07C 271/16 |

FOREIGN PATENT DOCUMENTS

| EP | 0074708 A2 | 3/1983 |
| EP | 2873410 A1 | 5/2015 |
| EP | 3604318 A1 | 2/2020 |
| JP | S58021607 A | 2/1983 |
| JP | S62099388 A | 5/1987 |
| JP | 2006-298771 A | 11/2006 |
| JP | 2010235554 A | 10/2010 |
| JP | 2014091692 A * | 5/2014 |
| JP | 2017025058 A | 2/2017 |
| WO | 2011041677 A2 | 4/2011 |

OTHER PUBLICATIONS

International Search Report (PCT/ISA/210) dated Jul. 3, 2018, by the Japanese Patent Office as the International Searching Authority for International Application No. PCT/JP2018/013232.
Written Opinion (PCT/ISA/237) dated Jul. 3, 2018, by the Japanese Patent Office as the International Searching Authority for International Application No. PCT/JP2018/013232.
Altin Ayse et al: "Synthesis and photopolymerization of novel, highly reactive phosphonated-urea-methacrylates for dental materials", Reactive and Functional Polymers, vol. 73, No. 9, Jul. 16, 2013 (Jul. 16, 2013), pp. 1319-1326, XP028689612.
Yohann Catel et al: "Monomers for adhesive polymers. XV. Synthesis, photopolymerization, and adhesive properties of polymerizable [beta]-ketophosphonic acids", Journal of Polymer Science Part A: Polymer Chemistry, Oct. 1, 2014 (Oct. 1, 2014), pages n/a-n/a, XP055731220, US ISSN:0887-624X, DOI: 10.1002/pola.27423.
Yohann Catel et al: "Monomers for adhesive polymers, 13. 1 Synthesis, radical photopolymerization and adhesive properties of polymerizable 2-substituted 1,3-propylidenediphosphonic acids", Designated Monomers and Polymers, vol. 17, No. 3, Oct. 14, 2013 (Oct. 14, 2013), pp. 286-299, XP055731222, DOI: 10.1080/15685551.2013.840503.
Melek Naz Guven et al: "Urea dimethacrylates functionalized with bisphosphonate/bisphosphonic acid for improved dental materials", Journal of Polymer Science Part A: Polymer Chemistry, vol. 55, No. 19, Jul. 6, 2017 (Jul. 6, 2017), pp. 3195-3204, XP055731227, US ISSN:0887-624X, DOI:10.1002/pola.28684.

(Continued)

Primary Examiner — Peter A Salamon
(74) Attorney, Agent, or Firm — Buchanan, Ingersoll & Rooney PC

(57) ABSTRACT

Provided are adhesive monomers for dental materials including compounds represented by the general formula (1) below, in which the core (X) and the terminal group (Y1) are bonded to each other directly or via the linking group (Z): $X(Y1)n^{1a}(Z—Y1)n^{1b}(1)$ wherein $n^{1a}$ represents the number of terminal groups (Y1) directly bonded to the core (X), $n^{1b}$ represents the number of terminal groups (Y1) bonded to the core (X) via the linking group (Z), and the sum of $n^{1a}$ and $n^{1b}$ is equal to the valence of the core (X); the core (X), the linking group (Z) and the terminal group (Y1) are further defined. The adhesive monomers can enhance adhesive strength to the tooth in dental treatment, and impart high mechanical strength to cured products.

13 Claims, No Drawings

(56) References Cited

OTHER PUBLICATIONS

Perez-Garrido A et al: "QSAR models to predict mutagenicity of acrylates, methacrylates and @a,@b-unsaturated carbonyl compounds", Dental Materials, Elsevier, Amsterdam, NL, vol. 26, No. 5, May 1, 2010 (May 1, 2010), pp. 397-415, XP026994108, ISSN:0109-5641 [Retrieved on Feb. 1, 2010].
Extended European Search Report dated Sep. 25, 2020, issued by the European Patent Office in corresponding European Application No. 18777195.1-1107, (11 pages).
Tauscher, et al., "Monomers for adhesive polymers, 17.a Synthesis, photopolymerization and adhesive properties of polymerizable phosphonic acids bearing urea groups", Designed Monomers and Polymers, Sep. 2016, vol. 19, No. 1, pp. 77-88. (the reference is cited in an Office Action dated Aug. 17, 2021, for corresponding EP patent application No. 18777195.1).
Catel, et al., "Monomers for adhesive polymers, 18. Synthesis, photopolymerization and adhesive properties of polymerizable α-phosphonooxy phosphonic acids", Designed Monomers and Polymers, Sep. 2017, vol. 20, No. 1, pp. 106-117. (the reference is cited in an Office Action dated Aug. 17, 2021, for corresponding EP patent application No. 18777195.1).

* cited by examiner

ADHESIVE MONOMERS FOR DENTAL MATERIALS

TECHNICAL FIELD

The present invention relates to adhesive monomers for dental materials, dental materials including the monomers, and kits including the dental materials.

BACKGROUND ART

In recent years, the concept of minimal intervention (MI) has been proposed from the standpoint of tooth preservation, and such clinical approaches as anticipation of remineralization of initial dental caries and minimal invasion in cavity formation have been popularized. In the case where a dental caries part is restored using a composite resin, an adhesive material for bonding the resin to the tooth is necessary (Non-Patent Literature 1). In the context of MI, development of restorative materials having high tooth adhesiveness, as well as development of adhesive monomers ensuring sufficient adhesive strength with a small bonding area and having toughness and durability, and improvement of tooth surface treatment methods, is strongly desired. A typical adhesive monomer for dental materials serves as a coupling agent between the resin and the tooth as the adhesive monomer for dental materials contains a carboxylic acid or a phosphate group at the end. MDP (10-methacryloyloxydecyl dihydrogen phosphate) having a phosphoric acid ester group is a useful phosphoric acid monomer which is not only used for adhesive materials but also blended with many dental materials such as composite resins because the monomer has higher bonding performance as compared to carboxylic acid-based adhesive monomers such as MAC-10 (11-methacryloxy-1,1-undecane dicarbonic acid) and 4-META (4-methacryloxyethyl trimellitate anhydride) (see, for example, Patent Literature 1). However, MDP is a monofunctional monomer, so that there is a limit to resin matrix formation, and thus enhancement of strength cannot be expected. On the other hand, phosphoric acid monomers containing a plurality of acrylic groups in the molecule have been reported. The phosphoric acid monomers can be expected to enhance resin strength, but have the problem that sufficient adhesive strength is not developed because the distance between the phosphoric acid ester group and the acrylate in the molecule, the acidity environment of the phosphoric acid ester group reaction field and the distance between the crosslinking points of acrylates are not adequate (see, for example, Patent Literatures 2 and 3). Thus, it is strongly desired to develop novel adhesive acrylate compounds which have high strength and adhesiveness and which can be blended with resin bonding materials and composite resin materials.

CITATION LIST

Patent Literature

Patent Literature 1: JP-A-S58-21607
Patent Literature 2: JP-A-2010-235554
Patent Literature 3: US 2009/0043009

Non-Patent Literature

Non-Patent Literature 1: Norbert Moszner et al., Chemical aspects of self-etching enamel-dentin adhesives: A systematic review, Dental Materials, 21, 2005, pp. 895-910

SUMMARY OF INVENTION

Technical Problem

In view of the above-described problems, an object of the present invention is to provide adhesive monomers for dental materials having the function of enhancing adhesive strength with the tooth in dental treatment.

Solution to Problem

The present inventors have conducted studies for solving the above-described problems, and as a resultant found that compositions containing (meth)acrylate compounds having phosphorus-containing groups and carbamate groups have high adhesive strength with the tooth. Consequently, the present invention has been completed.

The present invention includes the subject matters described in [1] to [11] below. [1] A adhesive monomer for dental materials comprising a compound represented by the general formula (1) below, in which the core (X) below and the terminal group (Y1) below are bonded to each other directly or via the linking group (Z) below:

[Chem. 1]

$$X(Y1)n^{1a}(Z-Y1)n^{1b} \tag{1}$$

(in the general formula (1), $n^{1a}$ represents the number of terminal groups (Y1) directly bonded to the core (X), $n^{1b}$ represents the number of terminal groups (Y1) bonded to the core (X) via the linking group (Z), and the sum of $n^{1a}$ and $n^{1b}$ is equal to the valence of the core (X); the core (X) is a $C_{1\text{-}200}$ polyvalent organic group having a valence of not less than 3 containing an oxygen atom or a nitrogen atom in which an atom bonded to the terminal group (Y1) or the linking group (Z) is the oxygen atom or the nitrogen atom; the terminal group (Y1) is a phosphorus-containing group represented by the general formula (2) below, a phosphorus-containing group represented by the general formula (3) below, a (meth)acryloyl group-containing group (Y2) represented by the general formula (4) below, a (meth)acryloyl group, a $C_{1\text{-}20}$ hydrocarbon group or a hydrogen atom, and a plurality of terminal groups (Y1) may be the same as or different from each other, with the proviso that among all the terminal groups (Y1) in the compound represented by the general formula (1), one or more terminal groups are phosphorus-containing groups represented by the general formula (2) below or phosphorus-containing groups represented by the general formula (3) below, and one or more terminal groups are (meth)acryloyl group-containing groups (Y2); and the linking group (Z) is a divalent group represented by the general formula (5) below, and when the compound represented by the general formula (1) contains a plurality of linking groups (Z), the linking groups (Z) may be the same as or different from each other)

[Chem. 2]

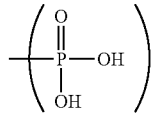

(2)

[Chem. 3]

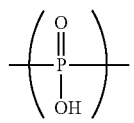

(3)

(in the general formula (3), one end of the group is bonded to the core (X) or the linking group (Z), and the other end of the group is bonded to the core (X) or the linking group (Z) present in another compound represented by the general formula (1))

[Chem. 4]

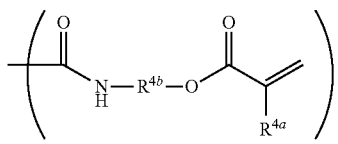

(4)

(in the general formula (4), $R^{4a}$ represents a hydrogen atom or a methyl group, $R^{4b}$ represents a $C_{2-6}$ linear alkylene group or a $C_{2-6}$ linear oxyalkylene group, and the linear alkylene group or the linear oxyalkylene group is optionally substituted with a $C_{1-6}$ alkyl group or a (meth)acryloyloxymethylene group in place of a hydrogen atom); and

[Chem. 5]

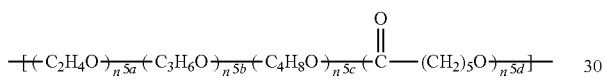

(5)

(in the general formula (5), $n^{5a}$, $n^{5b}$, $n^{5c}$ and $n^{5d}$ represent the unit numbers of respective repeating units, and are each 0 to 100, the sum of $n^{5a}$, $n^{5b}$, $n^{5c}$ and $n^{5d}$ is 1 to 100, the left end of the group is bonded to the core (X), and the right end of the group is bonded to the terminal group (Y1)).

[2] The adhesive monomer for dental materials according to [1], wherein the terminal group (Y1) is a phosphorus-containing group represented by the general formula (2), a phosphorus-containing group represented by the general formula (3), a (meth)acryloyl group-containing group (Y2) represented by the general formula (4), or a hydrogen atom.

[3] The adhesive monomer for dental materials according to [1] or [2], wherein the terminal group (Y1) is a phosphorus-containing group represented by the general formula (2), a phosphorus-containing group represented by the general formula (3), or a (meth)acryloyl group-containing group (Y2) represented by the general formula (4).

[4] The adhesive monomer for dental materials according to any of [1] to [3], wherein $n^{5a}$, $n^{5b}$, $n^{5c}$ and $n^{5d}$ in the linking group (Z) are each 0 to 20, and the sum of $n^{5a}$, $n^{5b}$, $n^{5c}$ and $n^{5d}$ is 1 to 20.

[5] The adhesive monomer for dental materials according to any of [1] to [4], wherein the linking group (Z) is a divalent group represented by the general formula (6) below:

[Chem. 6]

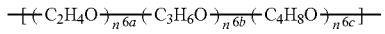

(6)

(in the general formula (6), $n^{6a}$, $n^{6b}$ and $n^{6c}$ represent the unit numbers of respective repeating units, and are each 0 to 20, the sum of $n^{6a}$, $n^{6b}$ and $n^{6c}$ is 1 to 20, the left end of the group is bonded to the core (X), and the right end of the group is bonded to the terminal group (Y1)).

[6] The adhesive monomer for dental materials according to any of [1] to [5], wherein the linking group (Z) is a divalent group represented by the general formula (7) below:

[Chem. 7]

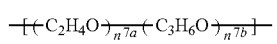

(7)

(in the general formula (7), $n^{7a}$ and $n^{7b}$ represent the unit numbers of respective repeating units, and are each 0 to 20, the sum of $n^{7a}$ and $n^{7b}$ is 1 to 20, the left end of the group is bonded to the core (X), and the right end of the group is bonded to the terminal group (Y1)).

[7] The adhesive monomer for dental materials according to any of [1] to [6], wherein the core (X) is an organic group having a valence of 3 to 12.

[8] The adhesive monomer for dental materials according to any of [1] to [7], wherein the core (X) is at least one selected from the group consisting of groups represented by the general formulas (8a) to (8j) below:

[Chem. 8]

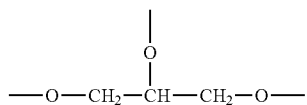

(8a)

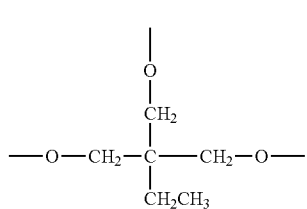

(8b)

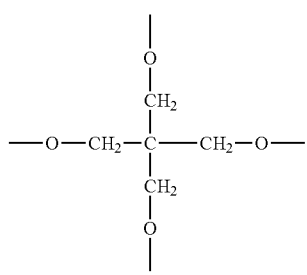

(8c)

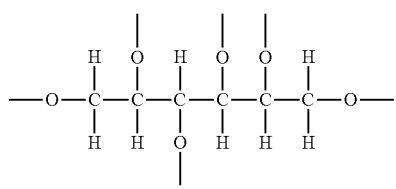

(8d)

-continued (8e)
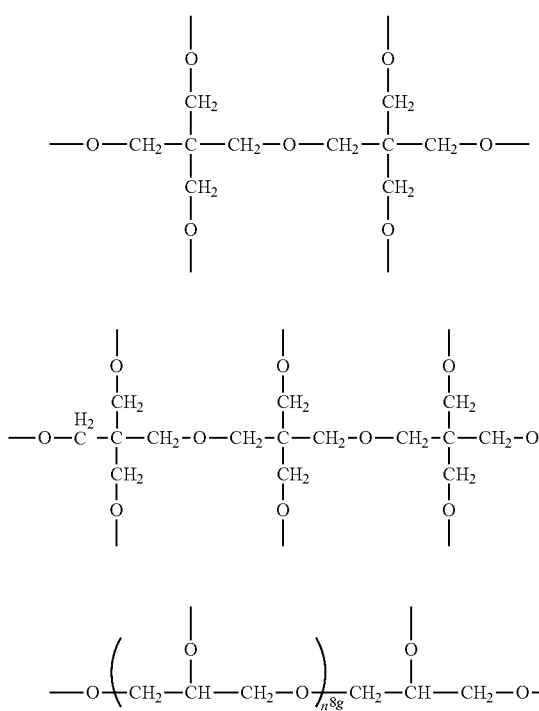

(8f)

(8g)

(in the general formula (8 g), $n^{8g}$ is an integer of 1 to 40).

(8h)
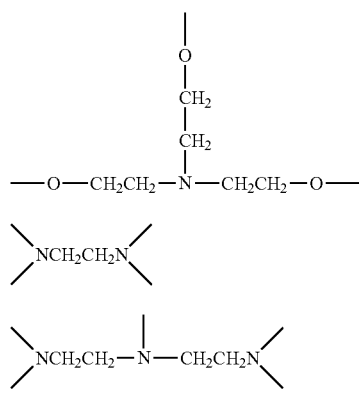

(8i)

(8j)
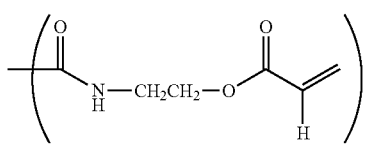

[9] The adhesive monomer for dental materials according to any of [1] to [8], wherein the (meth)acryloyl group-containing group (Y2) is at least one selected from the group consisting of groups represented by the general formulas (4a) to (4f) below:

[Chem. 9]

(4a)
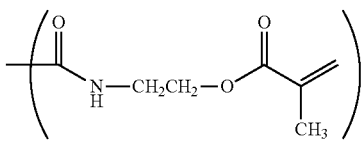

(4b)
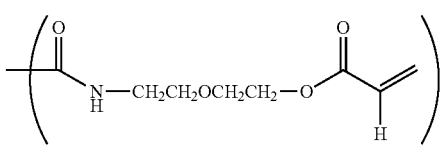

(4c)
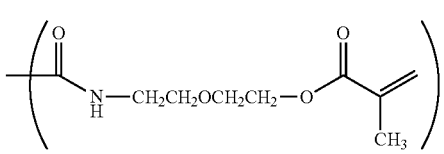

(4d)
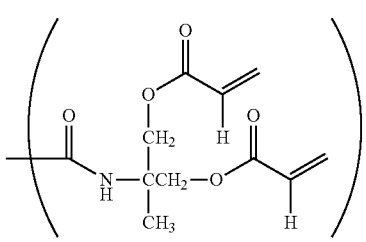

(4e)

(4f)
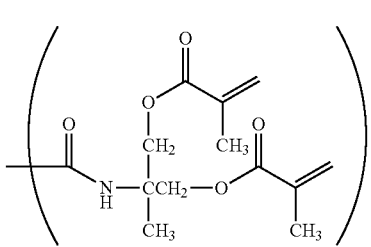

[10] A monomer composition for dental materials comprising the adhesive monomer for dental materials according to any of [1] to [9].

[11] The monomer composition for dental materials according to [10], wherein the monomer composition for dental materials is negative in a reverse mutation test.

[12] A dental material comprising the adhesive monomer for dental materials according to any of [1] to [9].

[13] The dental material according to [12], wherein the dental material is negative in a reverse mutation test.

[14] A kit comprising the dental material according to [12] or [13].

Advantageous Effects of Invention

The adhesive monomer for dental materials of the present invention has the function of enhancing adhesive strength with the tooth in dental treatment.

DESCRIPTION OF EMBODIMENTS

Hereinafter, the present invention will be described in detail. Herein, the "(meth)acryl" means acryl or methacryl, and for example, the "(meth)acrylic acid" means methacrylic acid or acrylic acid. Similarly, the "(meth)acryloyl" means "acryloyl" or "methacryloyl", and the "(meth)acrylate" means "acrylate" or "methacrylate".

[Adhesive Monomer for Dental Materials]

An adhesive monomer for dental materials according to the invention is a compound represented by the general formula (1) below, in which the core (X) below and the terminal group (Y1) below are bonded to each other directly or via the linking group (Z) below.

[Chem. 10]

$$X(Y1)n^{1a}(Z-Y1)n^{1b} \quad (1)$$

In the general formula (1), $n^{1a}$ represents the number of terminal groups (Y1) directly bonded to the core (X), $n^{1b}$ represents the number of terminal groups (Y1) bonded to the core (X) via the linking group (Z), and the sum of $n^{1a}$ and $n^{1b}$ is equal to the valence of the core (X). The combination of $n^{1a}$ and $n^{1b}$ is not limited as long as each of $n^{1a}$ and $n^{1b}$ is an integer of not less than 0 and the sum thereof is not less than 3. As an example of the combination, $n^{1a}$ is 0 and $n^{1b}$ is an integer of not less than 3, and in this case, all the terminal groups (Y1) are bonded to the core X via the linking group (Z). As another example of the combination, $n^{1b}$ is 0 and $n^{1a}$ is an integer of not less than 3, and in this case, all the terminal groups (Y1) are directly bonded to the core X.

[Core (X)]

The core (X) is a polyvalent organic group having a valence of not less than 3 containing an oxygen atom or a nitrogen atom in which an atom bonded to the terminal group (Y1) or the linking group (Z) is the oxygen atom or the nitrogen atom. The oxygen atom or nitrogen atom bonded to the terminal group (Y1) or the linking group (Z) is bonded to a methylene group or a divalent aromatic carbon group in addition to the terminal group (Y1) or the linking group (Z). Any hydrogen atom present in the methylene group or the divalent aromatic carbon group may be substituted by a $C_{1-12}$ monovalent hydrocarbon group. The number of carbon atoms in the core (X) is normally in the range of 1 to 200, preferably 1 to 100, more preferably 1 to 30, still more preferably 2 to 20.

The valence of the core (X) is not less than 3 as described above, and preferably 3 to 12, more preferably 3 to 8. The atom bonded to the terminal group (Y1) or the linking group (Z) is selected from an oxygen atom and a nitrogen atom as described above, and is preferably an oxygen atom. Examples of the core (X) include groups represented by the general formulas (8a) to (8j) below.

[Chem. 11]

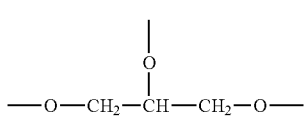

(8a)

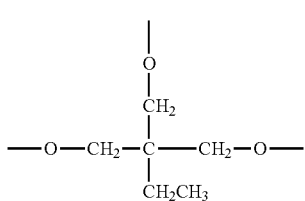

(8b)

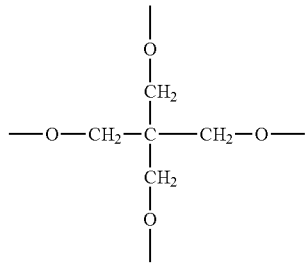

(8c)

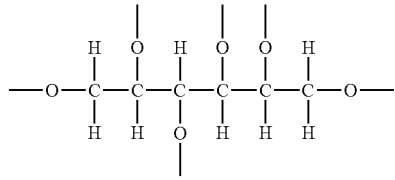

(8d)

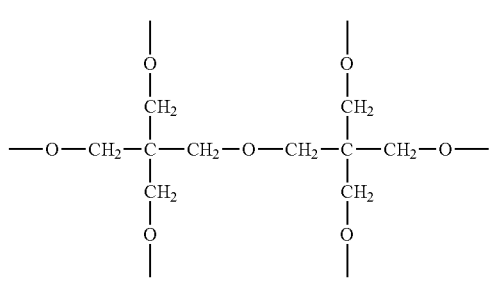

(8e)

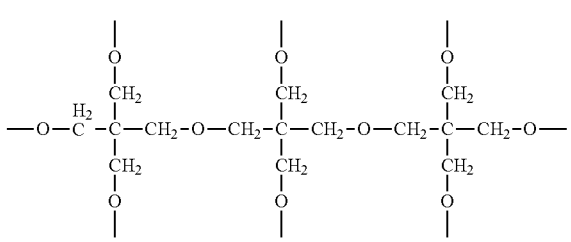

(8f)

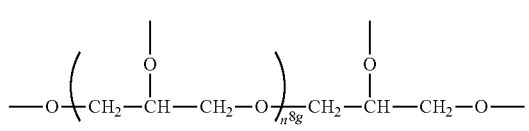

(8g)

(in the general formula (8g), $n^{8g}$ is an integer of 1 to 40).

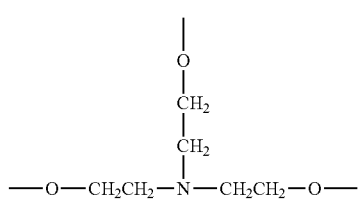

(8h)

(8i)

(8j)

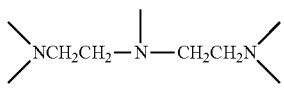

$n^{8g}$ in the general formula (8 g) is an integer of 1 to 40, preferably 1 to 20, more preferably 1 to 10, still more preferably 1 to 5.

[Terminal Group (Y1)]

The terminal group (Y1) is a phosphorus-containing group represented by the general formula (2) below, a phosphorus-containing group represented by the general formula (3) below, a (meth)acryloyl group-containing group (Y2) represented by the general formula (4) below, a (meth)acryloyl group, a $C_{1-20}$ hydrocarbon group or a hydrogen atom, and a plurality of terminal groups (Y1) may be the same as or different from each other, with the proviso that among all the terminal groups (Y1) in the compound represented by the general formula (1), one or more terminal groups are phosphorus-containing groups represented by the general formula (2) below or phosphorus-containing groups represented by the general formula (3) below, and one or more terminal groups are (meth)acryloyl group-containing groups (Y2).

[Chem. 12]

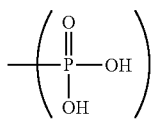

(2)

[Chem. 13]

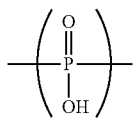

(3)

In the general formula (3), one end of the group is bonded to the core (X) or the linking group (Z), and the other end of the group is bonded to the core (X) or the linking group (Z) present in another compound represented by the general formula (1).

[Chem. 14]

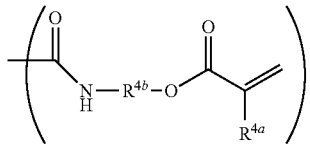

(4)

In the general formula (4), $R^{4a}$ represents a hydrogen atom or a methyl group, $R^{4b}$ represents a $C_{2-6}$ linear alkylene group or a $C_{2-6}$ linear oxyalkylene group, and the linear alkylene group or the linear oxyalkylene group is optionally substituted with a $C_{1-6}$ alkyl group or a (meth)acryloyloxymethylene group in place of a hydrogen atom. Examples of the (meth)acryloyl group-containing group (Y3) represented by the general formula (4) include groups represented by the general formulas (4a) to (4f) below.

[Chem. 15]

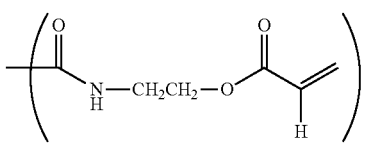
(4a)

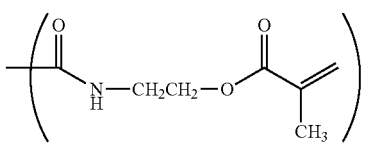
(4b)

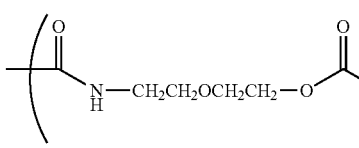
(4c)

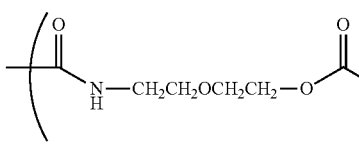
(4d)

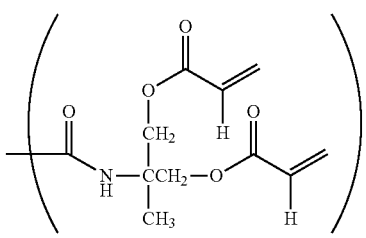
(4e)

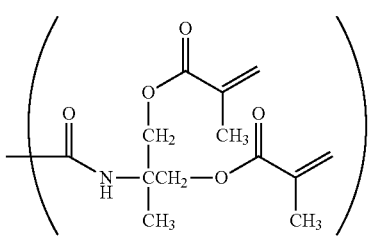
(4f)

The terminal group (Y1) is a phosphorus-containing group represented by the general formula (2), a phosphorus-containing group represented by the general formula (3), a (meth)acryloyl group-containing group (Y2) represented by the general formula (4), a (meth)acryloyl group, a $C_{1-20}$ hydrocarbon group or a hydrogen atom as described above, preferably a phosphorus-containing group represented by the general formula (2), a phosphorus-containing group represented by the general formula (3), a (meth)acryloyl group-containing group (Y2) represented by the general formula (4), or a hydrogen atom, more preferably a phosphorus-containing group represented by the general formula (2), a phosphorus-containing group represented by the general formula (3), or a (meth)acryloyl group-containing group (Y2) represented by the general formula (4).

[Linking Group (Z)]

The linking group (Z) is a divalent group represented by the general formula (5) below, and when the compound represented by the general formula (1) contains a plurality of linking groups (Z), the linking groups (Z) may be the same as or different from each other.

[Chem. 16]

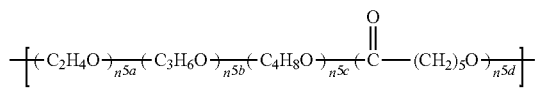
(5)

In the general formula (5), $n^{5a}$, $n^{5b}$, $n^{5c}$ and $n^{5d}$ represent the unit numbers of respective repeating units, and are each 0 to 100, preferably 0 to 20. The sum of $n^{5a}$, $n^{5b}$, $n^{5c}$ and $n^{5d}$ is 1 to 100, preferably 1 to 20. The left end of the group is bonded to the core (X), and the right end of the group is bonded to the terminal group (Y1).

The repeating unit represented by —$C_2H_4O$— in the general formula (5) is an oxyethylene unit. Examples of the oxyethylene unit include —$CH_2CH_2O$— and —$CH(CH_3)O$—. Of these oxyethylene units, —$CH_2CH_2O$— is preferable. These oxyethylene units may be present singly, or two or more thereof may be present in combination.

The repeating unit represented by —$C_3H_6O$— in the general formula (5) is an oxypropylene unit. Examples of the oxypropylene unit include groups such as —$CH_2CH_2CH_2O$—, —$CH(CH_3)CH_2O$— and —$CH_2CH(CH_3)O$—. Of these oxypropylene units, —$CH(CH_3)CH_2O$— and —$CH_2CH(CH_3)O$— are preferable. These oxypropylene units may be present singly, or two or more thereof may be present in combination.

The repeating unit represented by —$C_4H_8O$— in the general formula (5) is an oxybutylene unit. Examples of the oxybutylene unit include groups such as —$CH_2CH_2CH_2CH_2O$—, —$CH(CH_3)CH_2CH_2O$—, —$CH_2CH(CH_3)CH_2O$—, —$CH_2CH_2CH(CH_3)O$—, —$CH(CH_2CH_3)CH_2O$—, —$CH_2CH(CH_2CH_3)O$—, —$CH(CH_3)CH(CH_3)O$—, —$C(CH_3)_2CH_2O$— and —$CH_2C(CH_3)_2O$—. Of these oxybutylene units, —$CH_2CH_2CH_2CH_2O$— is preferable. These oxybutylene units may be present singly, or two or more thereof may be present in combination.

The repeating unit represented by —$CO(CH_2)_5O$— in the general formula (5) is one unit of a polycaprolactone chain.

The repeating unit may be composed of one type of repeating unit, or two or more types of repeating units. When the repeating unit includes two or more types of repeating units, the form in which these repeating units are present is not particularly limited, and for example, the repeating units may be randomly present, or a certain number of certain repeating units may be grouped, that is, repeating units may be present in the form of blocks. Further, the sequence of these repeating units is not limited.

The linking group (Z) is preferably a divalent group represented by the general formula (6) below. When the compound represented by the general formula (1) contains a plurality of linking groups (Z), the linking groups (Z) may be the same as or different from each other.

[Chem. 17]

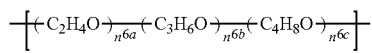
(6)

In the general formula (6), $n^{6a}$, $n^{6b}$ and $n^{6c}$ represent the unit numbers of respective repeating units, and are each 0 to 100, preferably 0 to 20. The sum of $n^{6a}$, $n^{6b}$ and $n^{6c}$ is 1 to 100, preferably 1 to 20. The left end of the group is bonded to the core (X), and the right end of the group is bonded to the terminal group (Y1). The descriptions of the repeating units in the general formula (6) are the same as the descriptions of the repeating units in the general formula (5).

The linking group (Z) is more preferably a divalent group represented by the general formula (7) below. When the compound represented by the general formula (7) contains a plurality of linking groups (Z), the linking groups (Z) may be the same as or different from each other.

[Chem. 18]

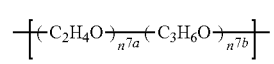
(7)

In the general formula (7), $n^{7a}$ and $n^{7b}$ represent the unit numbers of respective repeating units, and are each 0 to 100, preferably 0 to 20. The sum of $n^{7a}$ and $n^{7b}$ is 1 to 100, preferably 1 to 20. The left end of the group is bonded to the core (X), and the right end of the group is bonded to the terminal group (Y1). The descriptions of the repeating units in the general formula (7) are the same as the descriptions of the repeating units in the general formula (5).

More specific examples of the linking group (Z) may include linking groups having repeating units composed of only oxyethylene units (linking groups in which $n^{7b}$ is 0, and $n^{7a}$ is 1 to 100, preferably 1 to 20 in the general formula (7)), linking groups having repeating units composed of only oxypropylene units (linking groups in which $n^{7a}$ is 0, and $n^{7b}$ is 1 to 100, preferably 1 to 20 in the general formula (7)), and linking groups having a block structure of polymer block composed of oxypropylene units/polymer block composed of oxyethylene units/polymer block composed of oxypropylene units (linking groups having a structure in which blocks are linked in the structure (7') below in the general formula (7)).

[Chem. 19]

(7')

In the general formula (7'), $n^{7a1}$, $n^{7a2}$ and $n^{7b}$ represent the unit numbers of respective repeating units, and are each 1 to 100, preferably 1 to 20. The sum of $n^{7a1}$, $n^{7a2}$ and $n^{7b}$ is 1 to 100, preferably 1 to 20. The left end of the group is bonded to the core (X), the right end of the group is bonded to the terminal group (Y1), and the oxypropylene polymer blocks and the oxyethylene polymer block in the bracket are bonded in the order presented. The descriptions of the repeating units in the general formula (7') are the same as the descriptions of the repeating units in the general formula (5).

Examples of the adhesive monomer for dental materials of the invention include compounds represented by the general formulas (10a) to (10v) below.

[Chem. 20]
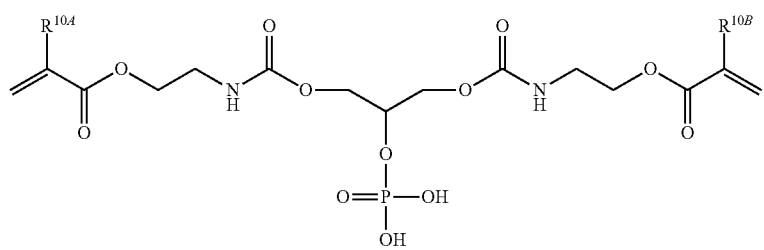
(10a)
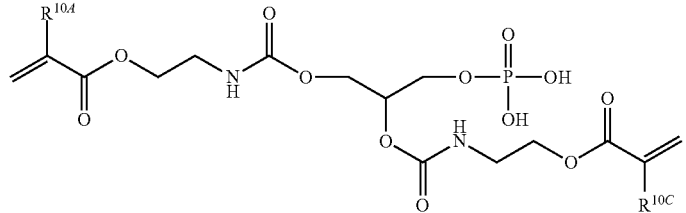
(10b)
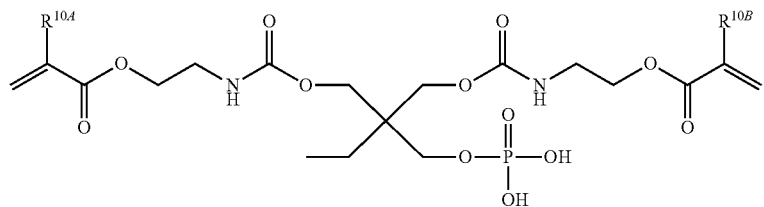
(10c)
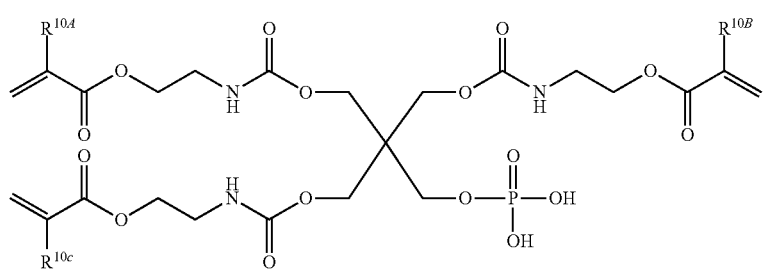
(10d)
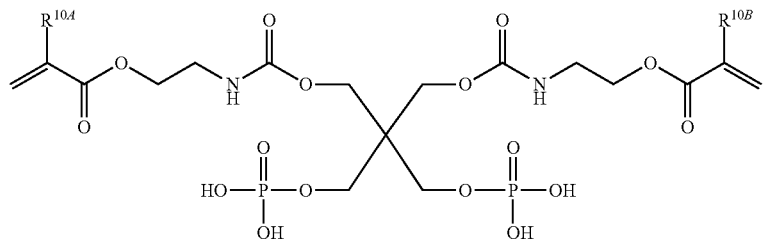
(10e)
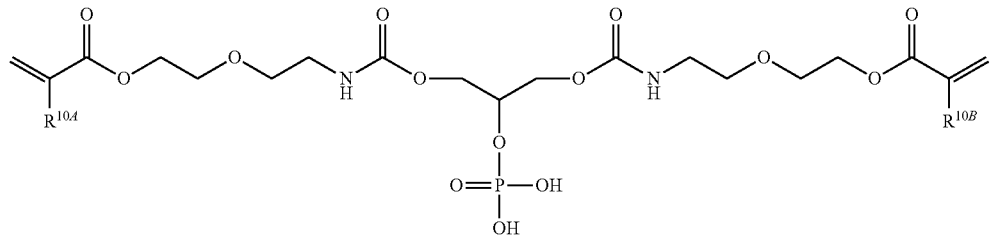
(10f)

-continued
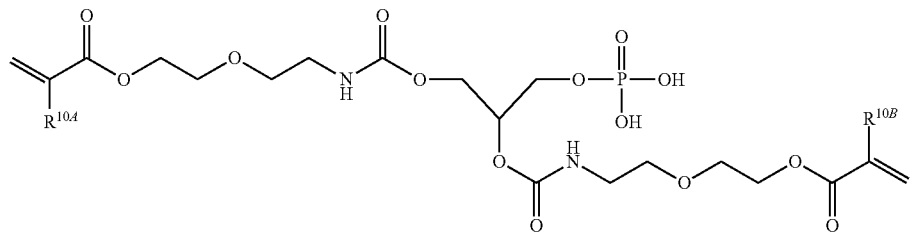
(10g)
[Chem. 21]
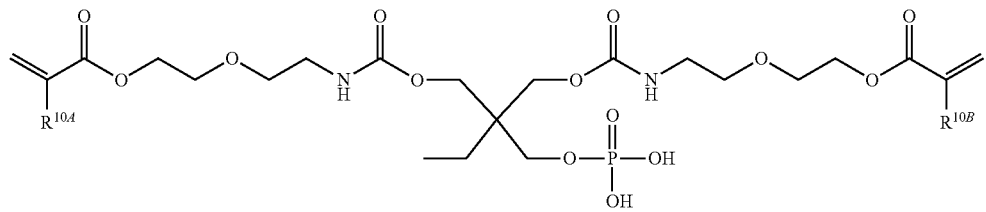
(10h)
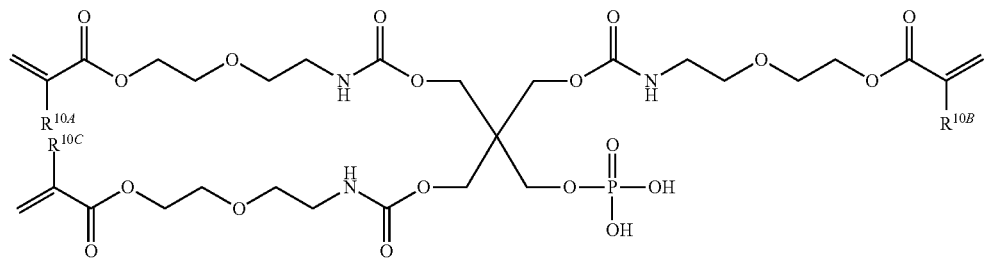
(10i)
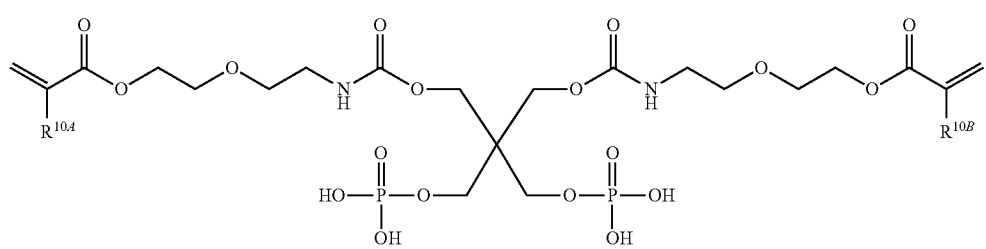
(10j)
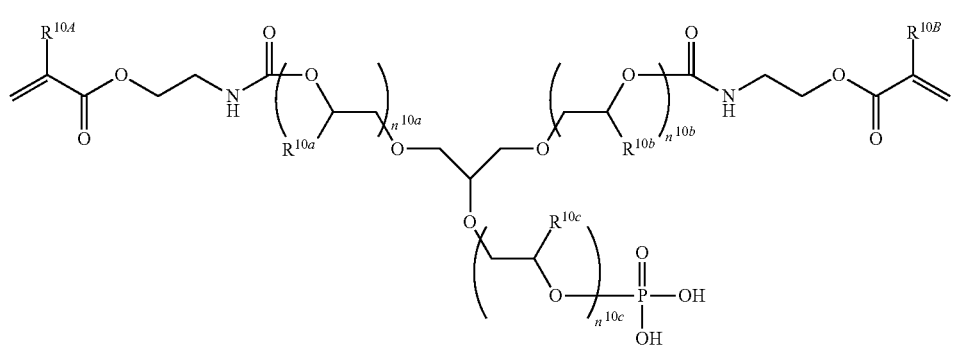
(10k)

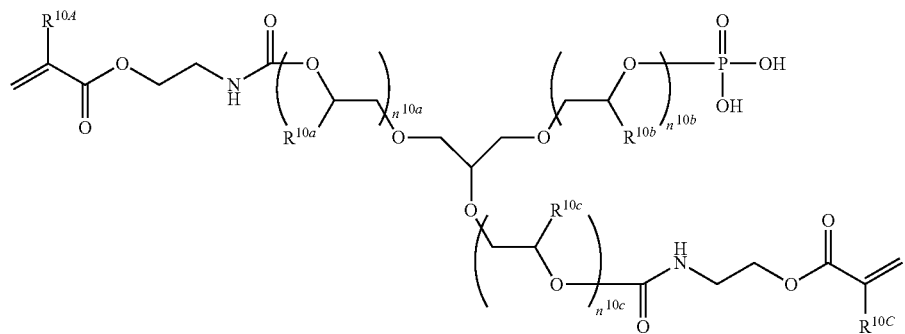
(10l)
[Chem. 22]
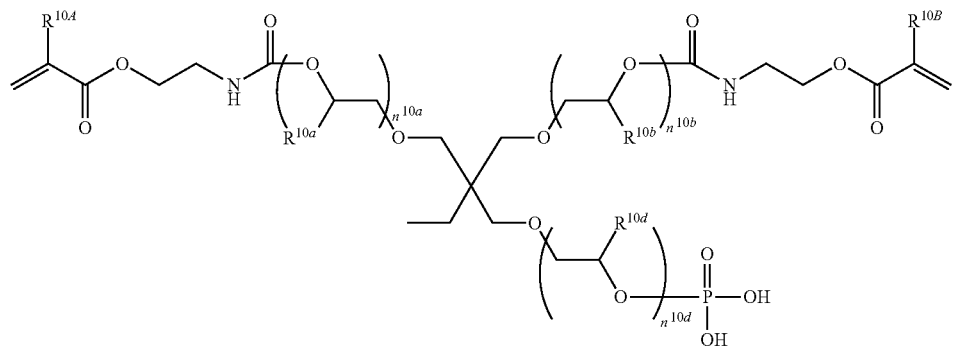
(10m)
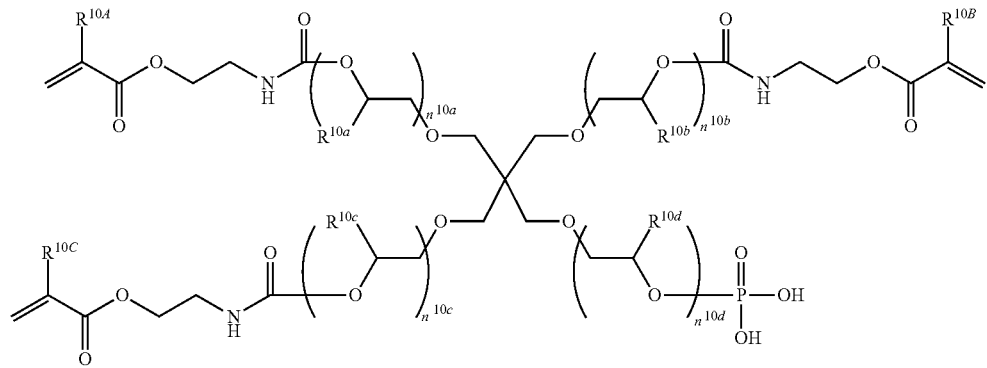
(10n)
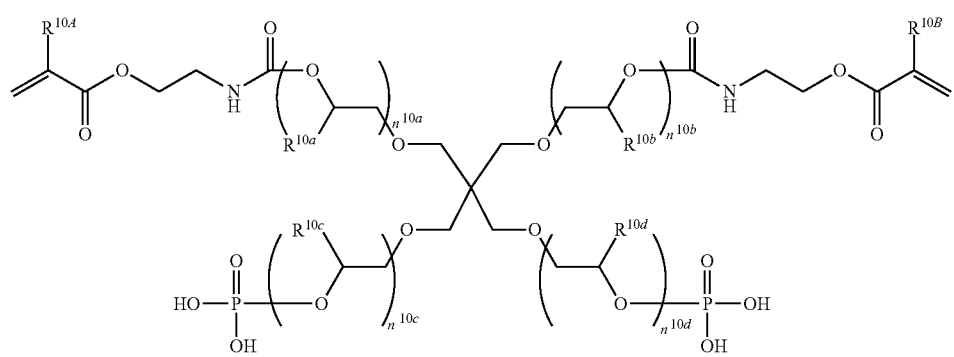
(10o)

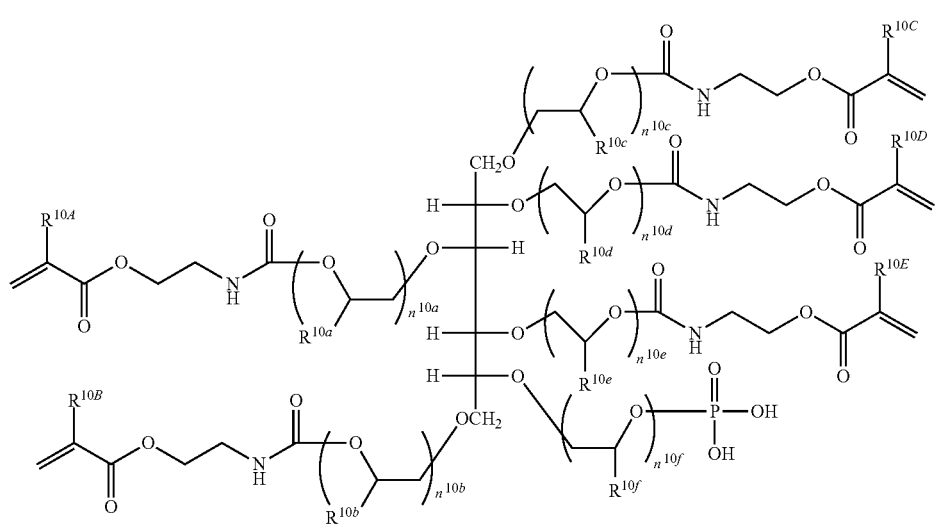
(10p)
[Chem. 23]
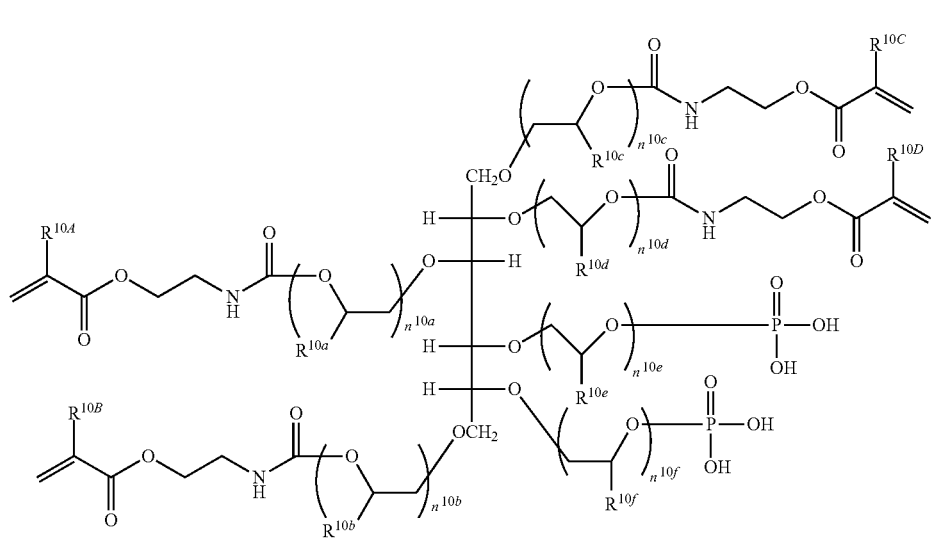
(10q)
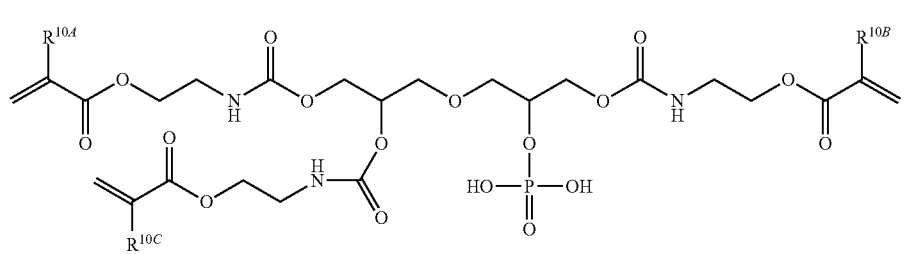
(10r)

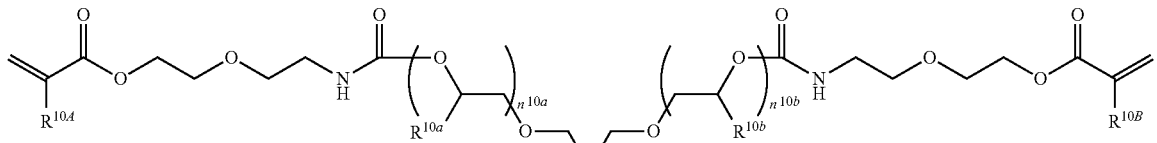

(10s)

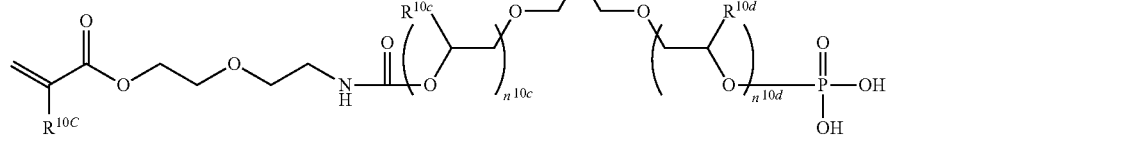

(10t)

[Chem. 24]

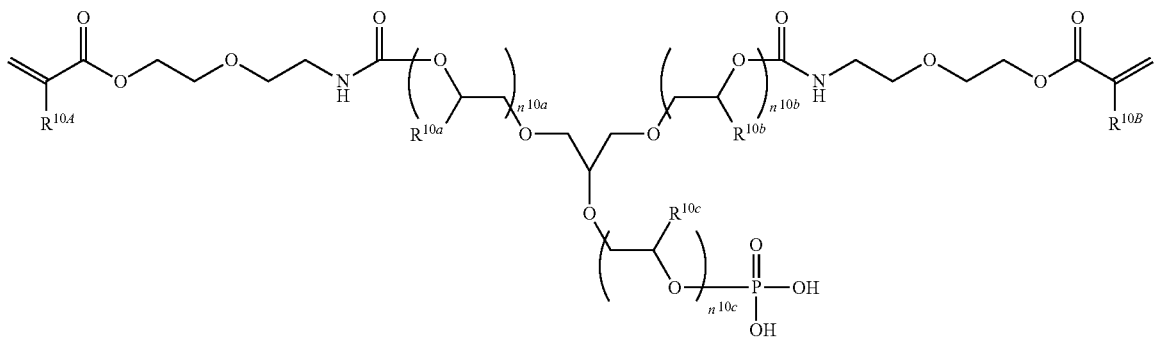

(10u)

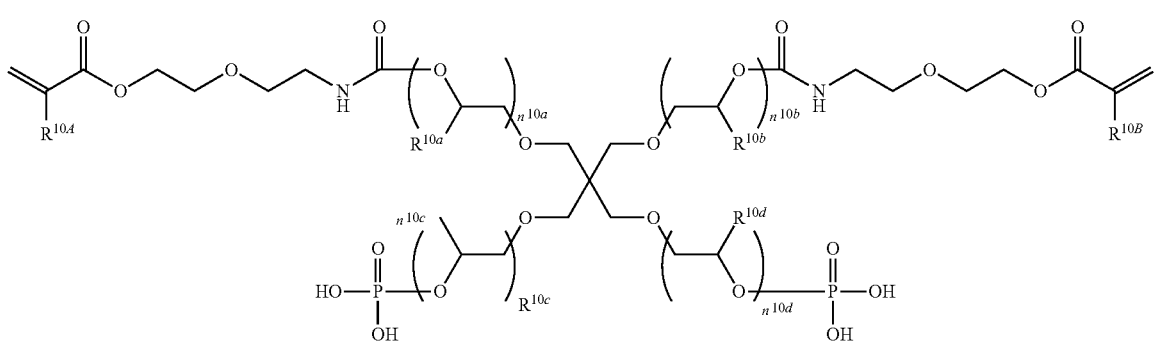

(10v)

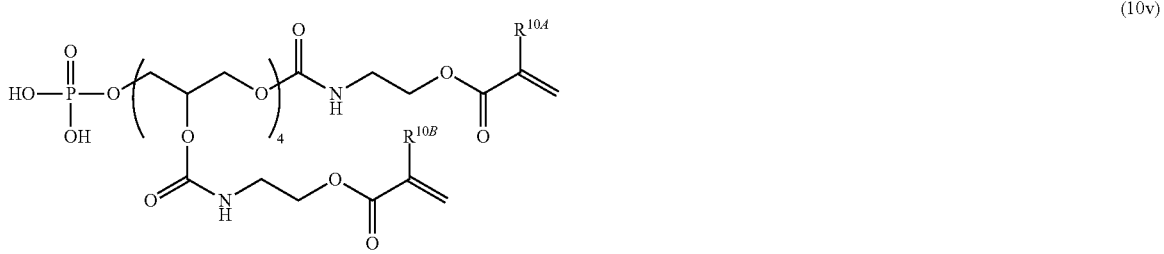

In the general formulas (10a) to (10v), $R^{10A}$, $R^{10B}$, $R^{10C}$, $R^{10D}$, $R^{10E}$, $R^{10a}$, $R^{10b}$, $R^{10c}$, $R^{10d}$, $R^{10e}$ and $R^{10f}$ are each a hydrogen atom or a methyl group. $n^{10a}$, $n^{10b}$, $n^{10c}$, $n^{10d}$, $n^{10e}$ and $n^{10f}$ represent the unit numbers of respective repeating units (specifically oxyethylene units or oxypropylene units), and each in the range of 1 to 100, preferably 1 to 20, and the unit numbers of the respective repeating units may be the same as or different from each other. Each repeating unit may be composed of one type of unit (oxyethylene unit or oxypropylene unit), or composed of two types of units (oxyethylene unit and oxypropylene unit). When the repeating unit is composed of two types of units, constituent units may be randomly present, or a certain number of certain repeating units may be grouped, that is, repeating units may be present in the form of blocks. Further, the sequence of these repeating units is not limited.

[Method for Producing Adhesive Monomer for Dental Materials]

The adhesive monomer for dental materials of the invention may be produced by a known method.

For example, a corresponding hydroxyl group-containing compound or amino group-containing compound, preferably a corresponding hydroxyl group-containing compound is reacted with a known phosphorylating agent (for example phosphorus pentaoxide, phosphorus pentachloride, phosphorus trichloride, phosphorus oxychloride or phosphorus pentasulfide) by a known method to form hydroxyl groups or amino groups, preferably hydroxyl groups, present in the compound into phosphoric acid esters or phosphoric acid amides.

The hydroxyl group or amino group-containing compound corresponding to the adhesive monomer for dental materials may be represented by the general formula (11) below, in which the core (X) below and the terminal group (Y3) below are bonded to each other directly or via the linking group (Z) below.

[Chem. 25]

$$X(Y3)_{n^{11a}}(Z\text{---}Y3)_{n^{11b}} \quad (1)$$

In the general formula (11), $n^{11a}$ represents the number of terminal groups (Y3) directly bonded to the core (X), $n^{11b}$ represents the number of terminal groups (Y3) bonded to the core (X) via the linking group (Z), and the sum of $n^{11a}$ and $n^{11b}$ is equal to the valence of the core (X). The combination of $n^{11a}$ and $n^{11b}$ is not limited as long as each of $n^{11a}$ and $n^{11b}$ is an integer of not less than 0 and the sum thereof is not less than 3. As an example of the combination, $n^{11a}$ is 0 and $n^{11b}$ is an integer of not less than 3, and in this case, all the terminal groups (Y3) are bonded to the core (X) via the linking group (Z). As another example of the combination, $n^{11b}$ is 0 and $n^{11a}$ is an integer of not less than 3, and in this case, all the terminal groups (Y3) are directly bonded to the core (X). The core (X) and the linking group (Z) are as described for the general formula (1)

[Terminal Group (Y3)]

The terminal group (Y3) is a (meth)acryloyl group-containing group (Y2) represented by the general formula (4), a (meth)acryloyl group, a $C_{1-20}$ hydrocarbon group or a hydrogen atom, preferably a (meth)acryloyl group-containing group (Y2) represented by the general formula (4), a (meth)acryloyl group or a hydrogen atom, more preferably (meth)acryloyl group-containing group (Y2) represented by the general formula (4) or a hydrogen atom. A plurality of terminal groups (Y3) may be the same as or different from each other, with the proviso that among all the terminal groups (Y3) in the compound represented by the general formula (11), one or more terminal groups are (meth) acryloyl group-containing groups (Y2), and one or more terminal groups are hydrogen atoms, preferably, two or more terminal groups are (meth)acryloyl group-containing groups (Y2), and one or more terminal groups are hydrogen atoms.

In production of the adhesive monomer for dental materials of the invention by the above method, all the hydroxyl groups or amino groups in the corresponding hydroxyl group or amino group-containing compound may be formed into phosphoric acid esters or phosphoric acid amides, or some hydroxyl groups or amino groups may remain. The products thus obtained can be used as the adhesive monomer for dental materials of the invention as long as they contain compounds represented by the general formula (1).

Further, in production of the adhesive monomer for dental materials of the invention by the above method, one ester group or amide group may be introduced, or two ester groups or amide groups may be introduced on one phosphorus atom. The products thus obtained can be used as the adhesive monomer for dental materials of the invention as long as they contain compounds represented by the general formula (1).

Specific Examples of Compounds of the General Formula (11)

Examples of the compounds of the general formula (11) include (meth)acryloyl group-containing group (Y2)-containing alcohols or (meth)acryloyl group-containing group (Y2)-containing polyols represented by the general formulas (11a) to (11v) below.

[Chem. 26]

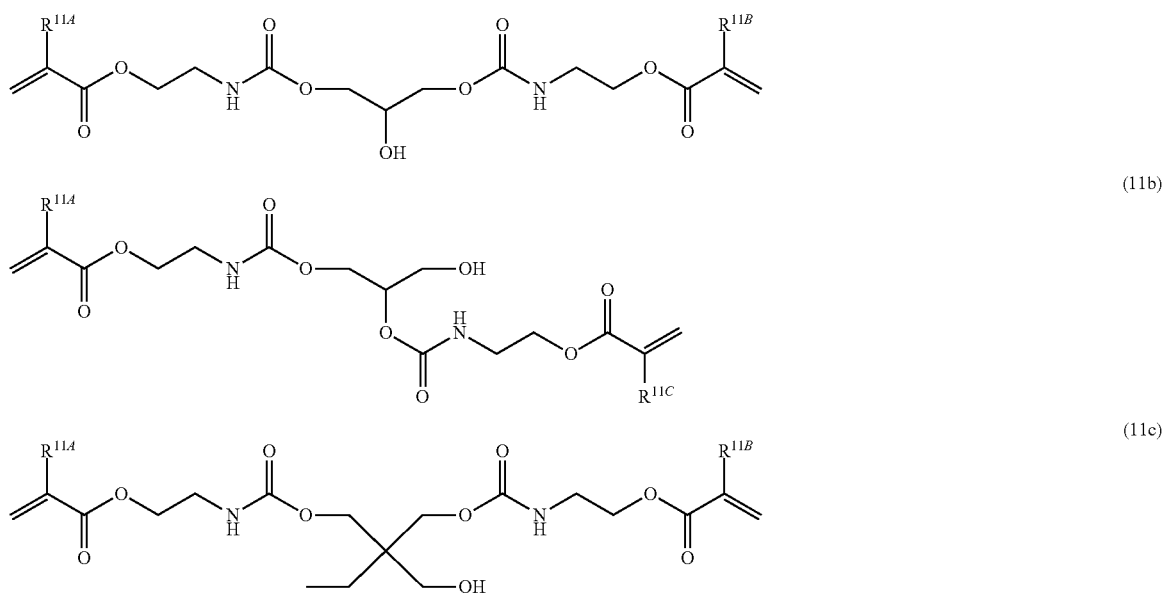

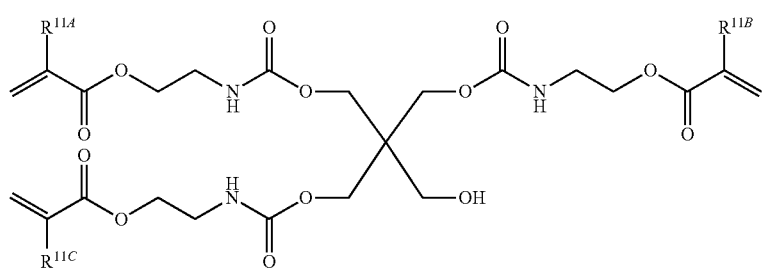
(11d)
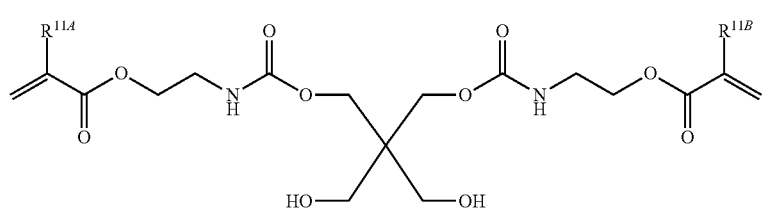
(11e)
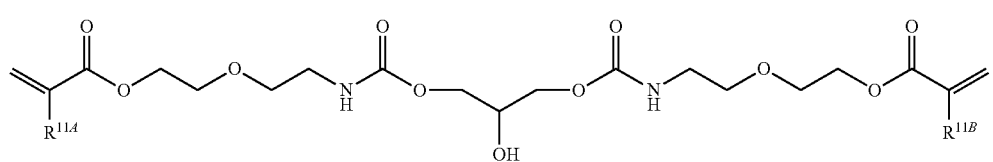
(11f)
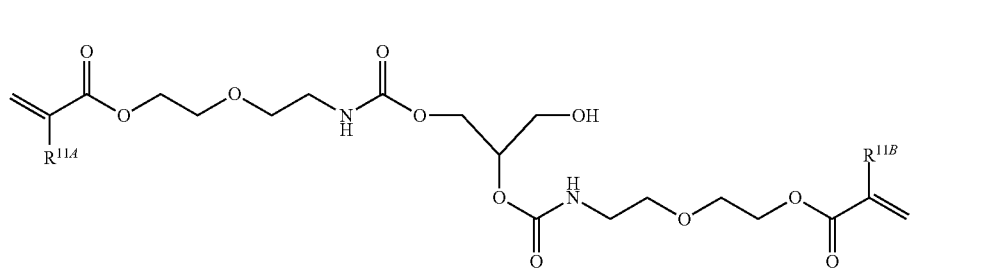
(11g)
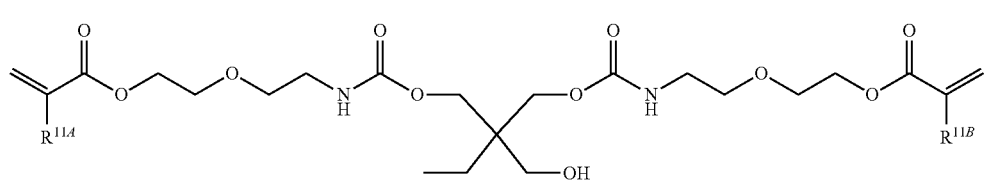
(11h)
[Chem. 27]
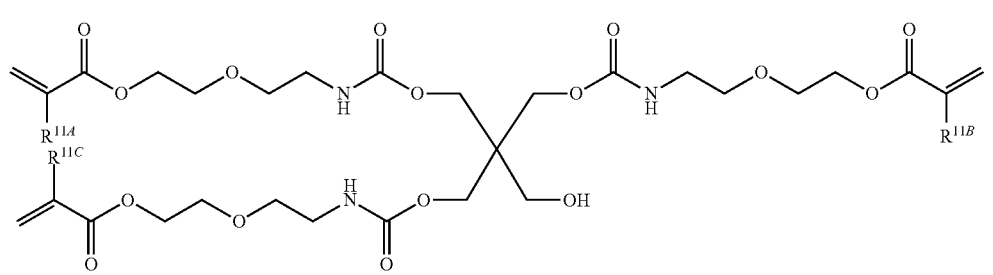
(11i)
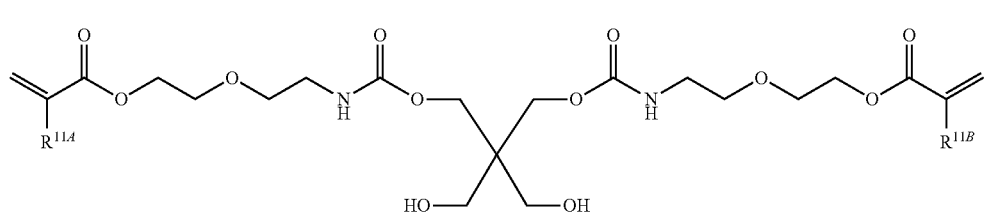
(11j)

(11k)
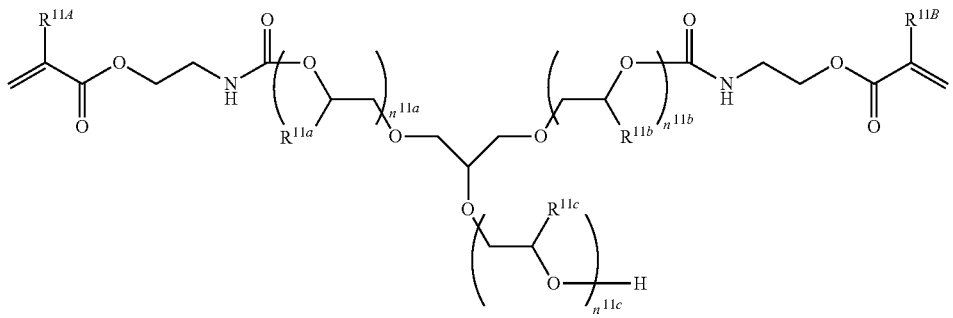
(11l)
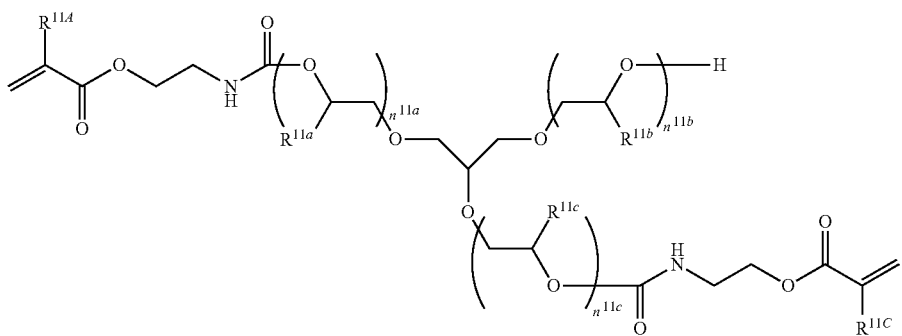
(11m)
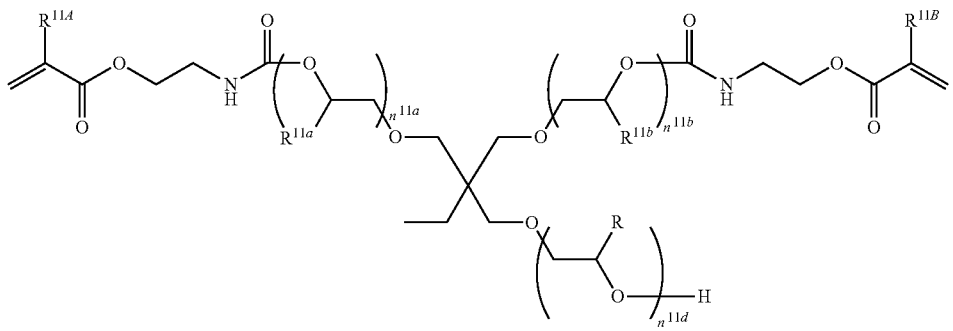
[Chem. 28]
(11n)
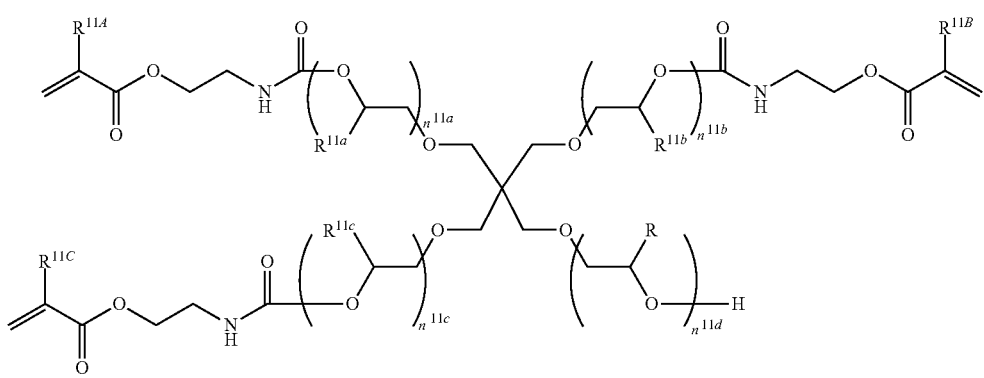

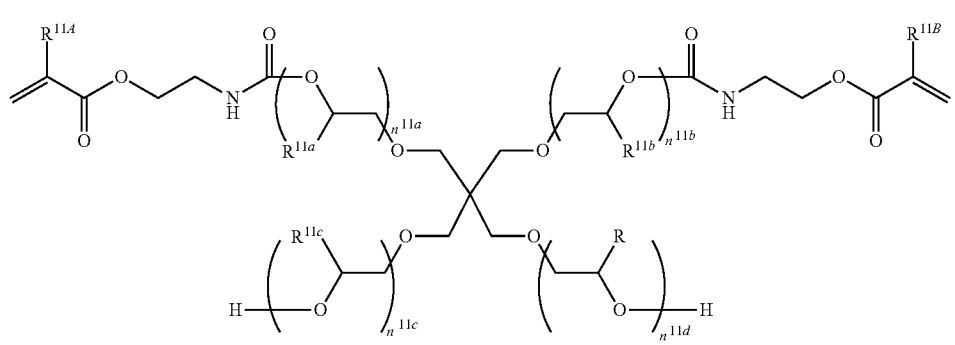
(11o)
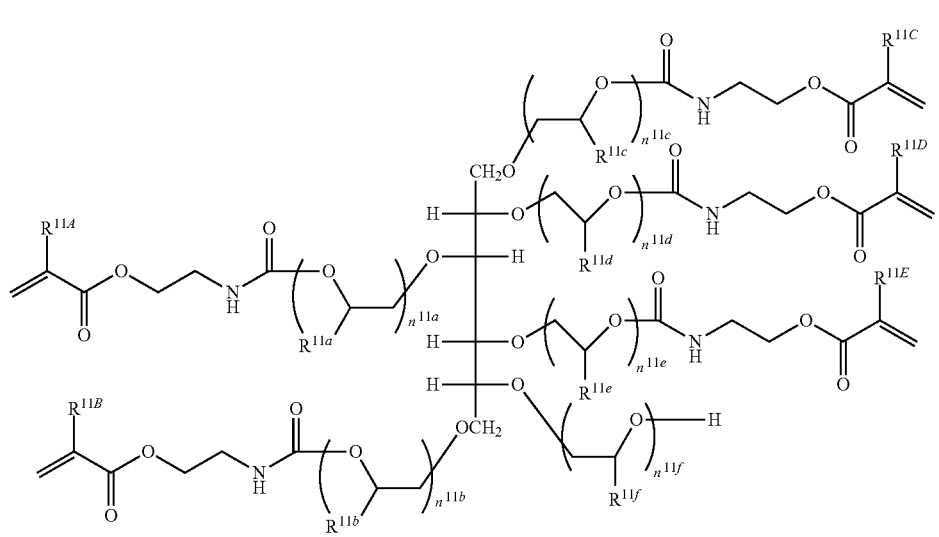
(11p)
[Chem. 29]
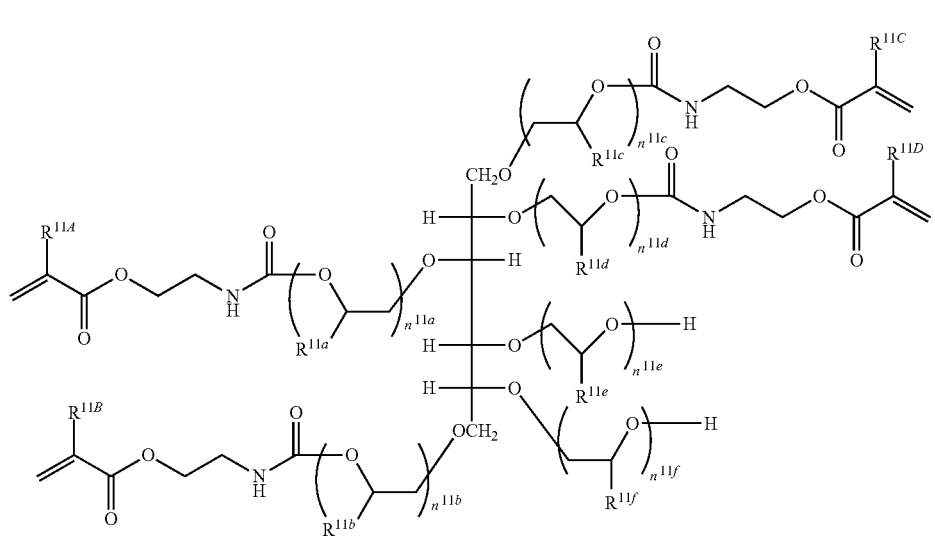
(11q)
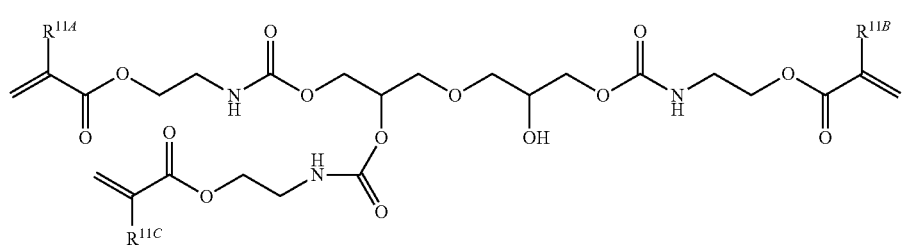
(11r)

-continued

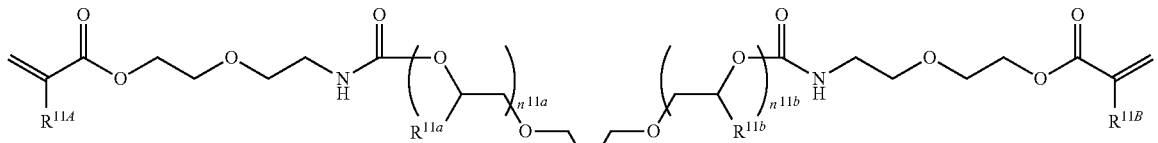
(11s)

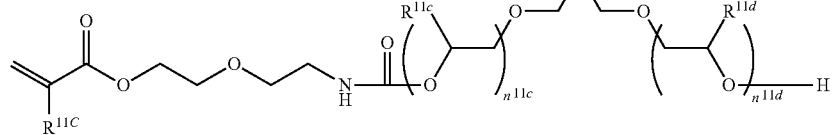
(11t)

[Chem. 30]

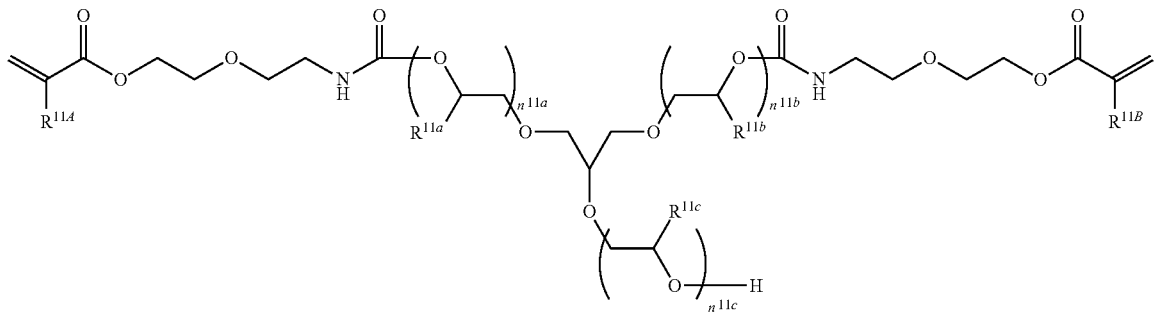
(11u)

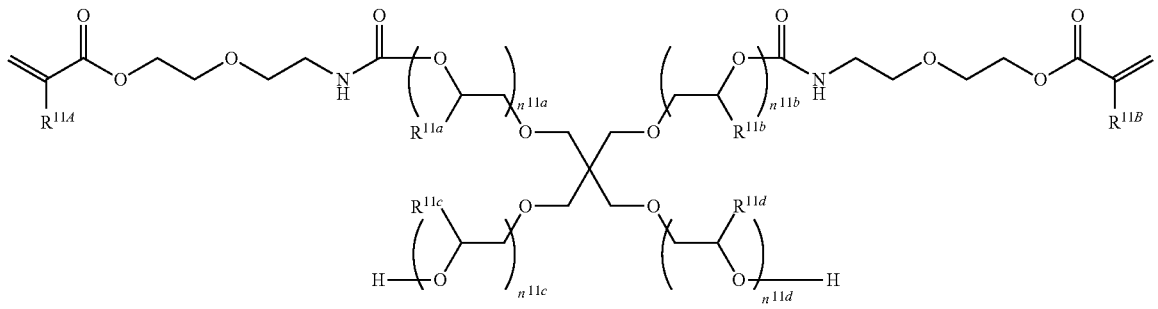
(11v)

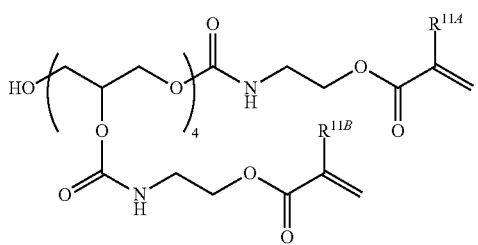

In the general formulas (11a) to (11v), $R^{11A}$, $R^{11B}$, $R^{11C}$, $R^{11D}$, $R^{11E}$, $R^{11a}$, $R^{11b}$, $R^{11c}$, $R^{11d}$, $R^{11e}$ and $R^{11f}$ are each a hydrogen atom or a methyl group. $n^{11a}$, $n^{11b}$, $n^{11c}$, $n^{11d}$, $n^{11e}$ and $n^{11f}$ represent the unit numbers of respective repeating units (specifically oxyethylene units or oxypropylene units), and each in the range of 1 to 100, preferably 1 to 20, and the unit numbers of the respective repeating units may be the same as or different from each other. Each repeating unit may be composed of one type of unit (oxyethylene unit or oxypropylene unit), or composed of two types of units (oxyethylene unit and oxypropylene unit). When the repeating unit is composed of two types of units, constituent units may be randomly present, or a certain number of certain repeating units may be grouped, that is, repeating units may be present in the form of blocks. Further, the sequence of these repeating units is not limited.

The method for producing the hydroxyl group-containing compound or amino group-containing compound corresponding to the adhesive monomer for dental materials of the invention is not particularly limited, and for example, the compound is obtained by reacting a (meth)acryloyl group-containing isocyanate compound represented by the general formula (12) below with a polyol compound under reaction conditions in which some hydroxyl groups remain.

[Chem. 31]

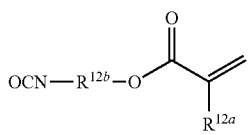

(12)

In the general formula (12), $R^{12a}$ represents a hydrogen atom or a methyl group, $R^{12b}$ represents a $C_{2-6}$ linear alkylene group or a $C_{2-6}$ linear oxyalkylene group, and the linear alkylene group or the linear oxyalkylene group is optionally substituted with a $C_{1-6}$ alkyl group or a (meth) acryloyloxymethylene group in place of a hydrogen atom.

[Monomer Composition for Dental Materials Containing Adhesive Monomer for Dental Materials]

The monomer composition for dental materials of the invention optionally contains polymerizable monomers other than the adhesive monomers for dental materials of the invention which can be blended with the later-described dental material (for example (meth)acrylate group-containing monomers other than the adhesive monomers for dental materials of the invention).

In the monomer composition for dental materials of the invention, for example, the content of the adhesive monomer for dental materials of the invention may be not less than 1.0 mass % (e.g. not less than 10 mass %, not less than 50 mass %, not less than 80 mass % or not less than 90 mass %) and may be not more than 100 mass % (e.g. not more than 99 mass %, not more than 90 mass %, not more than 80 mass %, not more than 50 mass % or not more than 10 mass %) based on the total amount of the monomer composition for dental materials.

(Reverse Mutation Test)

The monomer composition for dental materials according to the invention is preferably negative in a reverse mutation test. The reverse mutation test (Ames test) means a test for examining the mutagenicity of a monomer composition for dental materials using microorganisms. The reverse mutation test in the present invention is conducted by the following method.

Specifically, the reverse mutation test is conducted under a fluorescent lamp with an ultraviolet absorbing film and/or a LED in accordance with the following procedure.

First, to a sterilized test tube are added 0.1 mL of a test composition solution having dimethyl sulfoxide (DMSO) as a medium, and 0.5 mL of a 0.1 M phosphate buffer solution (pH 7.4) in the case where metabolic activation is not performed, or 0.5 mL of the later-described S9 mix in the case where metabolic activation is performed. Thereafter, 0.1 mL of the later-described bacterial suspension is added, and the resulting mixture is mixed. The resulting mixture is preincubated at about 100 rpm for 20 minutes, 2 mL of the later-described top agar is then added, and the resulting mixture is mixed, and overlaid on the later-described minimal glucose agar plate medium (five or more doses). After it is confirmed that the mixture has been overlaid and solidified, the minimal glucose agar plate medium is turned upside down, and culture is performed at 37° C. for 48 hours. Whether the result is negative or positive is determined on the cultured plate. When a negative control substance is subjected to the test, DMSO is used as the negative control substance, and 0.1 mL of the medium is added instead of the test composition solution in the above-described process.

After completion of the culture, the number of revertant colonies on each plate is measured.

Regarding the criterion for determining whether the result is negative or positive, it is determined that the monomer composition for dental materials is negative when the average number of colonies with the test composition is equal to or less than two times the average number of colonies with only the negative control substance for all strains, at all doses and in both the cases where metabolic activation is not performed and metabolic activation is performed.

In the reverse mutation test, the doses of a test substance present in the test composition solution (specifically, the adhesive monomer for dental materials present in the monomer composition for dental materials) are adjusted so that a maximum dose of 5000 µg per plate is followed by five or more doses descending in a geometric progression with a common ratio of 2 to 4.

The strain to be used is *Salmonella typhimurium* TA 100 or TA 1535, or *Escherichia coli* WP2uvrA, which are a base pair substitution mutant strain, or *Salmonella typhimurium* TA 98 or TA 1537, which are a frameshift mutant strain.

The minimal glucose agar plate medium to be used is Tesmedia AN Medium (manufactured by Oriental Yeast Co., Ltd., for testing of mutagenicity).

The number of the minimal glucose agar plate media per dose is not less than 2 for the negative control substance, and not less than 2 for the test composition.

The case where metabolic activation is performed means that S9 mix (a rat liver microsome fraction containing a coenzyme) is added together with a test substance, and the case where metabolic activation is not performed means that S9 mix is not added. Specifically, the S9 mix has the composition of S9: 0.1 mL (a supernatant portion of a liver homogenate centrifuged at 9000×g), $MgCl_2$: 8 µmol, KCl: 33 µmol, glucose-6-phosphoric acid: 5 µmol, NADPH: 4 µmol, NAPH: 4 µmol and sodium phosphate buffer solution (pH 7.4): 100 µmol.

The top agar to be used is a mixture obtained by subjecting an amino acid solution (0.5 mmol/L L-histidine, 0.5 mmol/L D-biotin and 0.5 mmol/L L-tryptophane) to filtration sterilization, subjecting a soft agar solution (0.6% (w/v) agar (Bacto-Agar) and 0.5% (w/v) sodium chloride) to high-pressure steam sterilization at 121° C. for 20 minutes, and mixing the amino acid solution and the melted soft agar solution at a volume ratio of 1:10.

In preparation of each bacterial suspension, the bacterial concentration is adjusted to not less than $1 \times 10^9$ bacteria per mL for each bacterium. For culture of each bacterium, a nutrient broth culture is used. The nutrient broth culture is prepared by dissolving Nutrient Broth No. 2 (Oxoid, Nutrient Broth No. 2) in purified water to a concentration of 2.5 wt %, and subjecting the resulting solution to high-pressure steam sterilization at 121° C. for 20 minutes.

(Cytotoxicity Test by NRU Method)

The monomer composition for dental materials according to the invention may allow the relative cell survival rate to fall within a certain range in a cytotoxicity test by an NRU method using the later-described Balb/3T3 cells. The cytotoxicity test is conducted by the following method.

Balb/3T3 cells (Balb/3T3 clone A31 cells (mouse skin-derived fibroblast cells)) are seeded at a density of 10000 cells per well in a 96-well plate, and precultured for 25 hours, the medium in each well is then removed, 0.1 mL of a test solution containing a test composition or a negative control solution is added to the cells, and the cells are cultured in a $CO_2$ incubator for 24 hours. Here, 12 wells are used for the negative control solution, and 6 wells are used for the test solution. After the culture, each well is observed under a microscope to confirm growth of the cells, the culture in each well is removed, and washing is performed with 0.15 mL of PBS. After the washing, 0.1 mL of an NR culture is added to each well, and the cells are cultured in a $CO_2$ incubator for 3 hours to perform staining. After the culture, the culture in each well is removed, and washing is performed with 0.15 mL of PBS. 0.15 ml of an NR-redissolving solution is added to each well, and shaken with a plate shaker for 10 minutes. Neutral red (NR) is dissolved in the NR-redissolving solution, the absorbance of the solution in each well is then measured at 540 nm, and the average value of the absorbances is determined. The absorbance of a solution in a well containing the test solution is calculated as a relative value against the absorbance of a solution in a well containing the negative control solution, with the latter absorbance set to 100, and the thus-obtained value is defined as a relative cell survival rate (%) of a test composition containing a test substance (a monomer composition for dental materials containing a adhesive monomer for dental materials).

For preparation of a test solution containing a test composition, a test composition is added to DMSO, and the resulting mixture is then diluted with DMSO to prepare a DMSO solution. Thereafter, 10 µL of the above-described DMSO solution is added per 2 mL of the later-described D05 culture, and the resulting mixture is stirred and mixed to prepare a test solution. The test solution is adjusted so that the test composition solution contains a test substance at a predetermined concentration (specifically, the monomer composition for dental materials contains a adhesive monomer for dental materials at a predetermined concentration).

The negative control solution is prepared by adding DMSO to the D05 culture to a concentration of 0.5 v/v %.

The D05 culture is D-MEM (Dulbecco's Modified Eagle's Medium 9, Cat No. 048-30275, containing 584 mg/L of glutamine and 5.958 g/L of HEPES) which contains 5 vol % of calf serum, 1 mmol/L sodium pyruvate and 1 vol % of a penicillin-streptomycin-amphotericin B suspension.

The D10 culture is D-MEM containing 10 vol % of calf serum, 1 vol % of a penicillin-streptomycin-amphotericin B suspension and 1 vol % of a 100 mmol/L sodium pyruvate solution.

The preculture of the Balb/3T3 cells is performed in the following manner: cells in the logarithmic growth phase are isolated using trypsin-EDTA, a cell suspension having a cell concentration of $1\times10^5$ cells/mL is then prepared using a D05 culture, and 0.1 mL of the cell suspension is then dispensed and seeded in a 96-well plate ($1\times10^4$ cells/well), and left standing in a $CO_2$ incubator for 25 hours.

The NR culture is a culture obtained by mixing an NR (neutral red) stock solution and a D10 culture at a ratio of 1:79, leaving the resulting mixture overnight at 37° C., and then removing the NR crystal by filtration with a filter.

The NR (neutral red) stock solution is a 0.4% (w/v) aqueous solution of neutral red (NR) (manufactured by Wako Pure Chemical Industries, Ltd.).

The NR-dissolving solution is a solution obtained by mixing acetic acid, ethanol and water at a ratio of 1:50:49. The NR-dissolving solution is prepared within an hour before use.

The concentration of the test substance of the test composition in the test solution may be, for example, 0.00164 mg/mL, 0.00410 mg/mL, 0.0102 mg/mL, 0.0256 mg/mL, 0.0640 mg/mL, 0.160 mg/mL, 0.400 mg/mL or 1.00 mg/mL.

When the concentration of the test substance of the test composition in the test solution is 0.00164 mg/mL, 0.00410 mg/mL, 0.0102 mg/mL, 0.0256 mg/mL, 0.0640 mg/mL, 0.160 mg/mL, 0.400 mg/mL or 1.00 mg/mL, the relative cell survival rate in the NRU method using the Balb/3T3 cells may be not less than 0.01% (e.g. not less than 0.05%, not less than 0.1%, not less than 0.5%, not less than 1.0%, not less than 5.0%, not less than 10%, not less than 20%, not less than 30%, not less than 40%, not less than 50%, not less than 60%, not less than 70%, not less than 80%, not less than 90%, not less than 95% or not less than 99%), and may be not more than 100% (e.g. not more than 99%, not more than 95%, not more than 90%, not more than 80%, not more than 70%, not more than 60%, not more than 50%, not more than 40%, not more than 30%, not more than 20%, not more than 10%, not more than 5.0%, not more than 1.0%, not more than 0.5%, not more than 0.1% or not more than 0.05%).

(Cell Test by WST Method)

The monomer composition for dental materials according to the invention may allow the relative cell growth rate to fall within a certain range in a cell test by a WST method using the Balb/3T3 cells. The cell test is conducted by the following method.

Balb/3T3 cells (Balb/3T3 clone A31 cells (mouse skin-derived fibroblast cells)) are seeded at a density of 2000 cells per well in a 96-well plate, and precultured for 24 hours, the culture in each well is then removed, 0.1 mL of a test solution containing a test composition or a negative control solution is added to the cells, and the cells are cultured in a $CO_2$ incubator for 48 hours. Here, 6 wells are used for the negative control solution, and 3 wells are used for the test solution.

After the culture, the test solution or the negative control solution is discarded, washing is performed with PBS, 0.2 mL of a DMEM culture containing a 10% WST-8 reagent is added to each well, and color reaction is carried out in a $CO_2$ incubator for 2 hours. The absorbance of the solution in the well after the reaction is measured at 450 nm and 650 nm by a microplate reader. A value obtained by subtracting the 650 nm-absorbance from the 450 nm-absorbance of the solution in each well is defined as the absorbance for each well, and with a negative value set to 0 if any, the average value of the absorbances is determined. A value obtained by dividing the average absorbance of the solution in wells containing the test solution by the average absorbance of the solution in wells containing the negative control solution is defined as a relative cell growth rate (%) of a test composition containing a test substance (a monomer composition for dental materials containing a adhesive monomer for dental materials).

For preparation of a test solution containing a test composition, a test composition is added to DMSO, and the resulting mixture is then diluted with DMSO to prepare a DMSO solution. Thereafter, 5 µL of the solution diluted with DMSO solution is added per mL of a DMEM culture to prepare a test solution. The test solution is adjusted so that the test composition solution contains a test substance at a predetermined concentration (specifically, the monomer composition for dental materials contains a adhesive monomer for dental materials at a predetermined concentration).

The negative control solution is prepared by adding DMSO to the DMEM culture to a concentration of 0.5 vol %.

The DMEM culture is Dulbecco's Modified Eagle's Medium (D-MEM) containing 10 vol % of calf serum and 1 vol % of a penicillin-streptomycin-amphotericin B suspension (×100).

The preculture of the Balb/3T3 cells is performed in the following manner: Balb/3T3 clone A31 cells in the logarithmic growth phase are isolated using 0.25% trypsin-1 mM EDTA, a cell suspension having a cell concentration of 20000 cells/mL is then prepared using a DMEM culture, and 0.1 mL of the cell suspension is then dispensed and seeded in a 96-well plate (2000 cells/well), and left standing in a $CO_2$ incubator for 24 hours.

The concentration of the test substance of the test composition in the test solution may be, for example, 0.00164 mg/mL, 0.00410 mg/mL, 0.0102 mg/mL, 0.0256 mg/mL, 0.0640 mg/mL, 0.160 mg/mL, 0.400 mg/mL or 1.00 mg/mL.

When the concentration of the test substance of the test composition in the test solution is 0.00164 mg/mL, 0.00410 mg/mL, 0.0102 mg/mL, 0.0256 mg/mL, 0.0640 mg/mL, 0.160 mg/mL, 0.400 mg/mL or 1.00 mg/mL, the relative cell growth blocking rate in the WST method using the Balb/3T3 cells may be not less than 0.001% (e.g. not less than 0.01%, not less than 0.05%, not less than 0.1%, not less than 0.5%, not less than 1.0%, not less than 5.0%, not less than 10%, not less than 20%, not less than 30%, not less than 40%, not less than 50%, not less than 60%, not less than 70%, not less than 80%, not less than 90%, not less than 95% or not less than 99%), and may be not more than 100% (e.g. not more than 99%, not more than 95%, not more than 90%, not more than 80%, not more than 70%, not more than 60%, not more than 50%, not more than 40%, not more than 30%, not more than 20%, not more than 10%, not more than 5.0%, not more than 1.0%, not more than 0.5%, not more than 0.1%, not more than 0.05% or not more than 0.01%).

[Dental Material Containing Adhesive Monomer for Dental Materials]

The adhesive monomer for dental materials of the invention is suitable as a raw material for dental materials because it is possible to enhance adhesive strength with the tooth in dental treatment while imparting sufficient mechanical strength to cured products of dental materials containing the adhesive monomer for dental materials of the invention. By blending the adhesive monomer for dental materials of the invention with components other than the adhesive monomers for dental materials of the invention (for example polymerizable monomers other than the adhesive monomers for dental materials of the invention ((meth)acrylate group-containing monomers other than the adhesive monomers for dental materials of the invention, monomers containing epoxy groups, and the like)), a dental material containing the adhesive monomer for dental materials of the invention can be produced.

[(Meth)Acrylate Group-Containing Monomers Other than Inventive Adhesive Monomers for Dental Materials]

Examples of the components other than the adhesive monomers for dental materials of the invention may include (meth)acrylate group-containing monomers other than the adhesive monomers for dental materials of the invention.

The (meth)acrylate group-containing monomer other than the adhesive monomers for dental materials of the invention contains one or more (meth)acrylate groups in the molecule. The number of polymerizable groups present may be 1, or not less than 2.

The (meth)acrylate group-containing monomer other than the adhesive monomers for dental materials of the invention may be composed of one compound, or composed of a mixture of two or more compounds.

Examples of the (meth)acrylate group-containing monomers other than the adhesive monomers for dental materials, which have only one polymerizable group, include monomers represented by the general formula (21) below.

[Chem. 32]

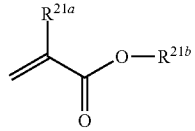

(21)

In the general formula (21), $R^{21a}$ represents hydrogen or a methyl group, and $R^{21b}$ represents a $C_{1-20}$ monovalent organic group which may contain oxygen or nitrogen.

Examples of the monovalent organic groups include hydrocarbon groups, for example, $C_{1-20}$ acyclic hydrocarbon groups such as alkyl groups, alkenyl groups and alkynyl groups, and $C_{1-20}$ cyclic hydrocarbon groups such as cycloalkyl groups, cycloalkenyl groups, cycloalkynyl groups and aryl groups; and $C_{1-20}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, alkoxyalkyl groups, alkoxyalkylene glycol groups and tetrahydrofurfuryl groups. The $C_{1-20}$ cyclic hydrocarbon groups may have acyclic hydrocarbon moieties. Further, the acyclic hydrocarbon moieties present in these groups may be linear or branched.

In the case where the $C_{1-20}$ hydrocarbon groups or the $C_{1-20}$ oxygen-containing hydrocarbon groups contain linear alkylene moieties, at least one of the methylene groups in such moieties may be substituted by an ester bond, an amide bond, a carbonate bond, a urethane bond (a carbamoyl group) or a urea bond (but the methylene groups are not substituted contiguously).

Further, hydrogen atoms present in the organic groups such as the $C_{1-20}$ hydrocarbon groups and the $C_{1-20}$ oxygen-containing hydrocarbon groups may be substituted by acid groups such as carboxyl groups and phosphate groups, and functional groups such as hydroxyl groups, amino groups and epoxy groups.

Examples of the methacryloyl group-containing compounds represented by the general formula (21) include methyl methacrylate, ethyl methacrylate, propyl methacrylate, butyl methacrylate, hexyl methacrylate, cyclohexyl methacrylate, ethoxydiethylene glycol methacrylate, methoxytriethylene glycol methacrylate, phenoxyethyl methacrylate, 2-hydroxyethyl methacrylate, 2-hydroxypropyl methacrylate, 2-hydroxybutyl methacrylate, 2-hydroxy-3-phenoxypropyl methacrylate, 4-hydroxybutyl methacrylate and 1,4-cyclohexanedimethanol monomethacrylate.

Examples of the acryloyl group-containing compounds represented by the general formula (21) include methyl acrylate, ethyl acrylate, propyl acrylate, butyl acrylate, hexyl acrylate, cyclohexyl acrylate, ethoxydiethylene glycol acrylate, methoxytriethylene glycol acrylate, phenoxyethyl acrylate, 2-hydroxyethyl acrylate, 2-hydroxypropyl acrylate, 2-hydroxybutyl acrylate, 2-hydroxy-3-phenoxypropyl acrylate, 4-hydroxybutyl acrylate and 1,4-cyclohexanedimethanol monoacrylate.

Examples of the (meth)acrylate group-containing monomers other than the adhesive monomers for dental materials of the invention, which have two or more polymerizable groups, include monomers represented by the general formula (22) below.

[Chem. 33]

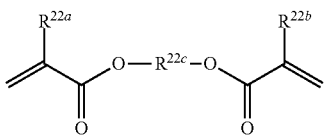

(22)

In the general formula (22), $R^{22a}$ and $R^{22b}$ each represent hydrogen or a methyl group and may be the same as or different from each other; and $R^{22c}$ represents a $C_{1-40}$ divalent organic group which may contain oxygen or nitrogen.

Examples of the divalent organic groups include hydrocarbon groups, for example, $C_{1-40}$ acyclic hydrocarbon groups such as alkylene groups, alkenylene groups and alkynylene groups, and $C_{1-40}$ cyclic hydrocarbon groups such as cycloalkylene groups, cycloalkenylene groups, cycloalkynylene groups and arylene groups; and $C_{1-40}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-40}$ cyclic hydrocarbon groups may have acyclic hydrocarbon moieties. Further, the acyclic hydrocarbon moieties present in these groups may be linear or branched.

In the case where the $C_{1-40}$ hydrocarbon groups or the $C_{1-40}$ oxygen-containing hydrocarbon groups contain linear alkylene moieties, at least one of the methylene groups in such moieties may be substituted by an ester bond, an amide bond, a carbonate bond, a urethane bond (a carbamoyl group) or a urea bond (but the methylene groups are not substituted contiguously).

Further, hydrogen atoms present in the organic groups such as the $C_{1-40}$ hydrocarbon groups and the $C_{1-40}$ oxygen-containing hydrocarbon groups may be substituted by acid groups such as carboxyl groups and phosphate groups, functional groups such as hydroxyl groups, amino groups and epoxy groups, and polymerizable groups such as acryloyl groups and methacryloyl groups.

Among the monomers represented by the general formula (22), some preferred monomers are those monomers in which $R^{22c}$ is a linear alkylene group having 2 to 20 carbon atoms, preferably 4 to 12 carbon atoms.

Examples of the compounds which correspond to the above preferred monomers and have methacryloyl groups include 1,4-butanediol dimethacrylate, 1,6-hexanediol dimethacrylate, 1,8-octanediol dimethacrylate, 1,9-nonanediol dimethacrylate and 1,10-decanediol dimethacrylate.

Examples of the compounds which correspond to the above preferred monomers and have acryloyl groups include 1,4-butanediol diacrylate, 1,6-hexanediol diacrylate, 1,8-octanediol diacrylate, 1,9-nonanediol diacrylate and 1,10-decanediol diacrylate.

Among the monomers represented by the general formula (22), other preferred monomers are those monomers in which $R^{22c}$ is a linear oxyalkylene group having 2 to 20 carbon atoms, preferably 4 to 12 carbon atoms.

Examples of the compounds which correspond to the above preferred monomers and have methacryloyl groups include ethylene glycol dimethacrylate, diethylene glycol dimethacrylate, triethylene glycol dimethacrylate, tetraethylene glycol dimethacrylate, polyethylene glycol dimethacrylate, tripropylene glycol dimethacrylate, tetrapropylene glycol dimethacrylate and polypropylene glycol dimethacrylate.

Examples of the compounds which correspond to the above preferred monomers and have acryloyl groups include ethylene glycol diacrylate, diethylene glycol diacrylate, triethylene glycol diacrylate, tetraethylene glycol diacrylate, polyethylene glycol diacrylate, tripropylene glycol diacrylate, tetrapropylene glycol diacrylate and polypropylene glycol diacrylate.

Among the monomers represented by the general formula (22), other preferred monomers are carbamoyl group-containing monomers represented by the general formula (23) below.

[Chem. 34]

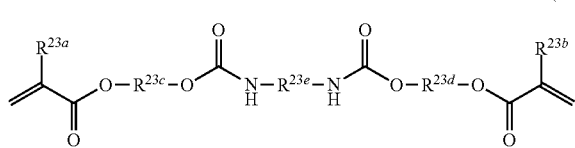

(23)

In the general formula (23), $R^{23a}$ and $R^{23b}$ each represent hydrogen or a methyl group and may be the same as or different from each other; and $R^{23c}$ and $R^{23d}$ each represent a $C_{1-12}$ divalent organic group which may contain oxygen, and may be the same as or different from each other.

Examples of the divalent organic groups include hydrocarbon groups, for example, $C_{1-12}$ acyclic hydrocarbon groups such as alkylene groups, and $C_{1-12}$ cyclic hydrocarbon groups such as cycloalkylene groups and arylene groups; and $C_{1-12}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-12}$ cyclic hydrocarbon groups may have acyclic hydrocarbon moieties. Further, the acyclic hydrocarbon moieties present in these groups may be linear or branched.

Further, hydrogen atoms present in the organic groups such as the $C_{1-12}$ hydrocarbon groups and the $C_{1-12}$ oxygen-containing hydrocarbon groups may be substituted by acid groups such as carboxyl groups and phosphate groups, functional groups such as hydroxyl groups, amino groups and epoxy groups, and polymerizable groups such as acryloyl groups and methacryloyl groups.

In the general formula (23), $R^{23e}$ represents a $C_{1-20}$ divalent organic group which may contain oxygen.

Examples of the divalent organic groups include hydrocarbon groups, for example, $C_{1-20}$ acyclic hydrocarbon groups such as alkylene groups, and $C_{1-20}$ cyclic hydrocarbon groups such as cycloalkylene groups and arylene groups; and $C_{1-20}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-20}$ cyclic hydrocarbon groups may have acyclic hydrocarbon moieties. Further, the acyclic hydrocarbon moieties present in these groups may be linear or branched.

Further, hydrogen atoms present in the organic groups such as the $C_{1-20}$ hydrocarbon groups and the $C_{1-20}$ oxygen-containing hydrocarbon groups may be substituted by acid groups such as carboxyl groups and phosphate groups, and functional groups such as hydroxyl groups, amino groups and epoxy groups.

Examples of the acryloyl group-containing compounds represented by the general formula (23) include urethane acrylates formed by the reaction between a hydroxyacrylate such as 2-hydroxyethyl acrylate, 2-hydroxypropyl acrylate, 2-hydroxybutyl acrylate, 2-hydroxy-3-phenoxypropyl acrylate, 4-hydroxybutyl acrylate or 1,4-cyclohexanedimethanol monoacrylate, and a diisocyanate such as 2,4- or 2,6-toluene diisocyanate, 4,4'-, 2,4'- or 2,2'-diphenylmethane-diisocyanate, 1,6-hexamethylene diisocyanate, or 2,2,4- or 2,4,4-trimethyl-1,6-hexamethylene-diisocyanate. Examples of such urethane acrylates include 2,2,4-trimethylhexamethylene bis(2-carbamoyloxyethyl) diacrylate.

Among the (meth)acryloyl group-containing compounds represented by the general formula (23), other preferred compounds may be at least one selected from the group consisting of compounds represented by the general formulas (24a) to (24e).

[Chem. 35]

(24a)

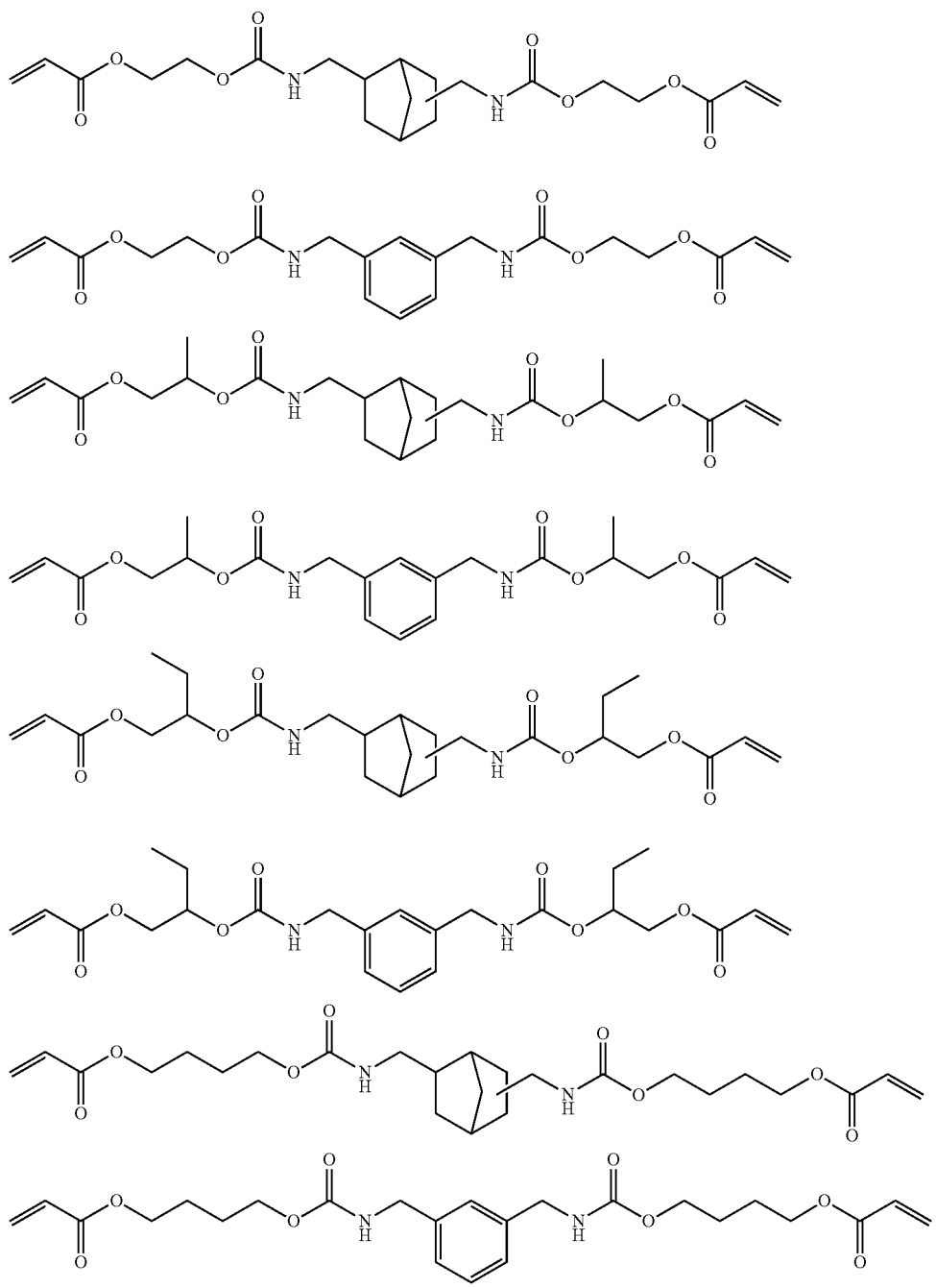

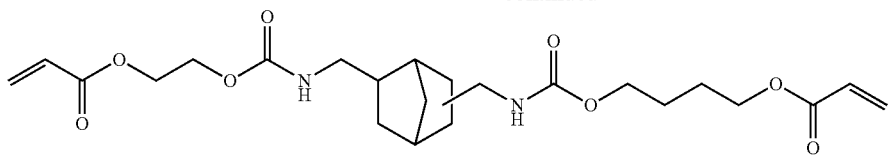
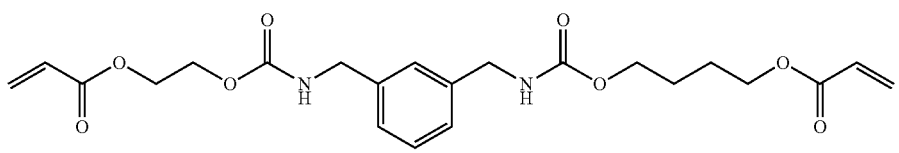
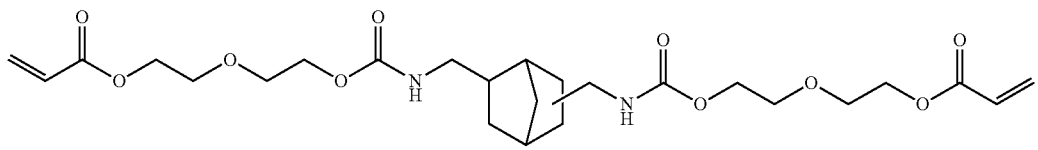
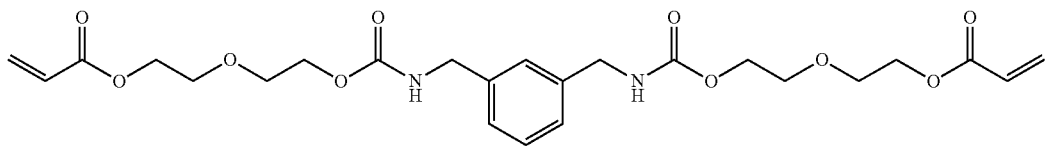
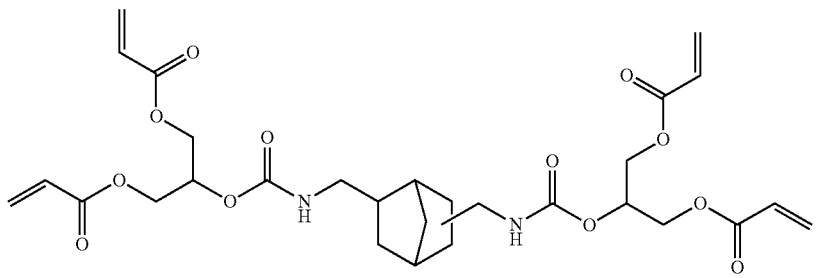
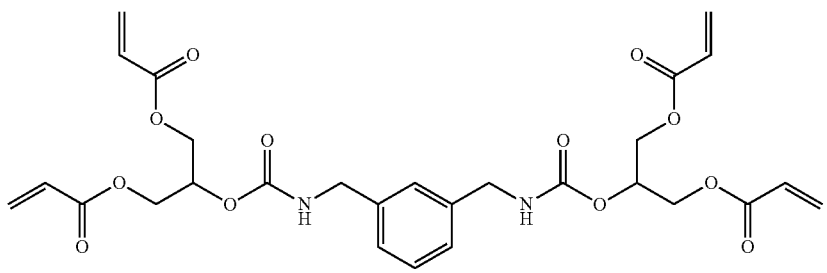
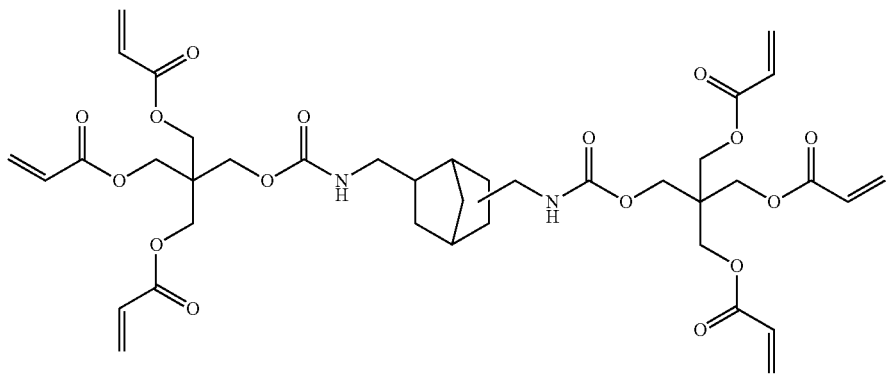

-continued
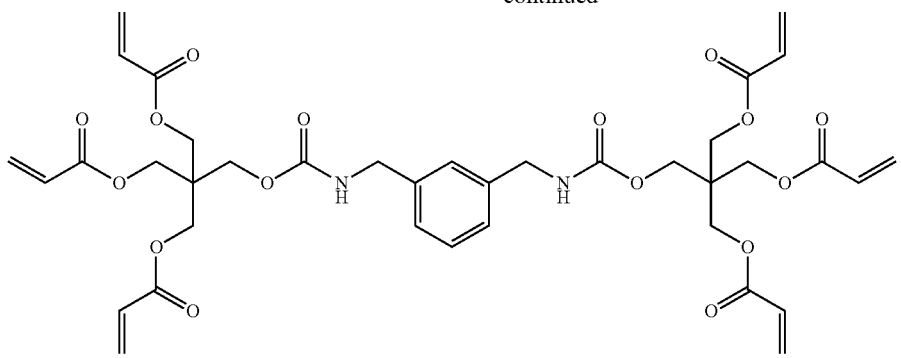
[Chem. 36]
(24b)
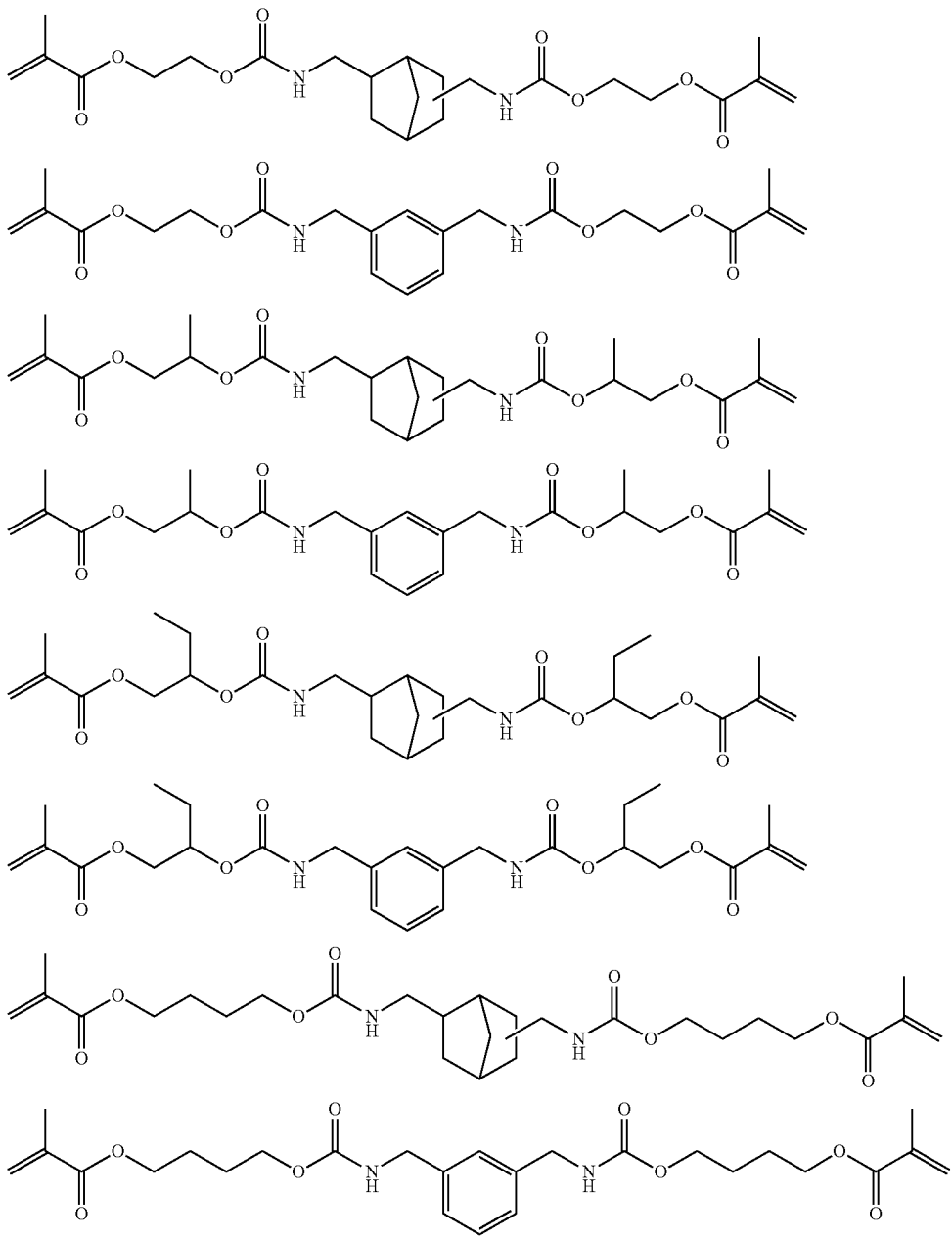

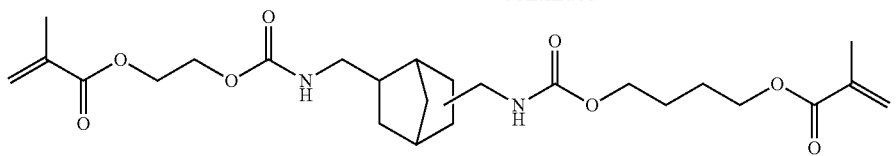
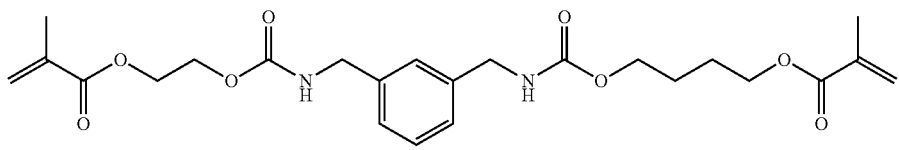
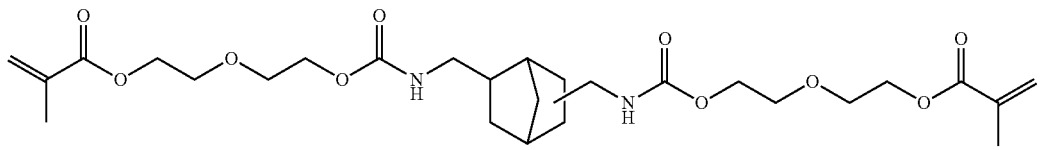
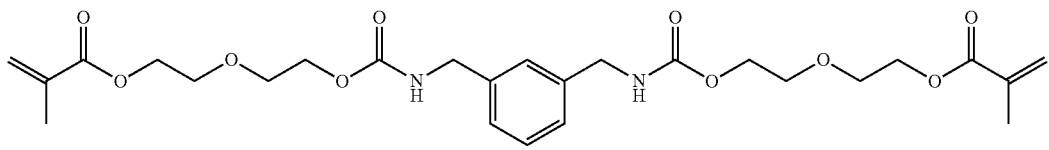
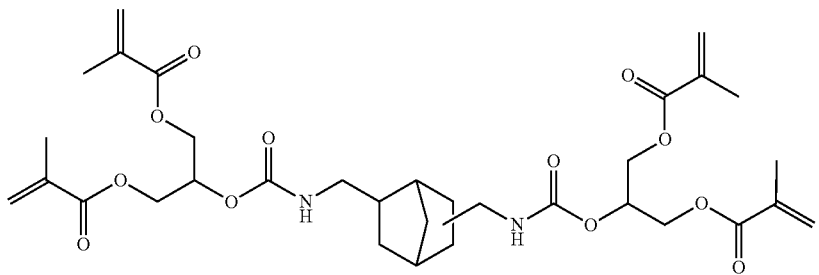
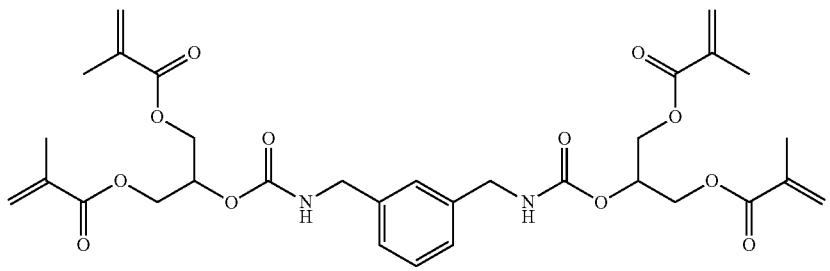
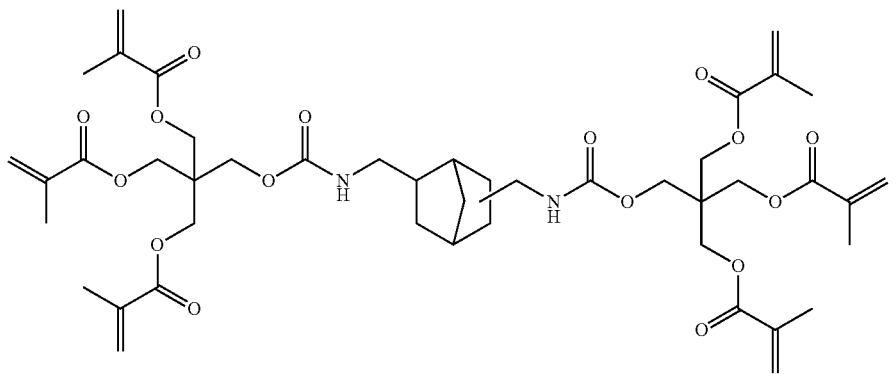

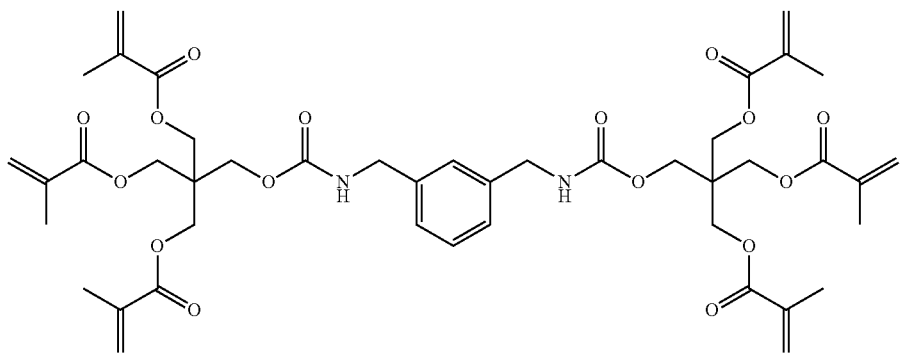
[Chem. 37]
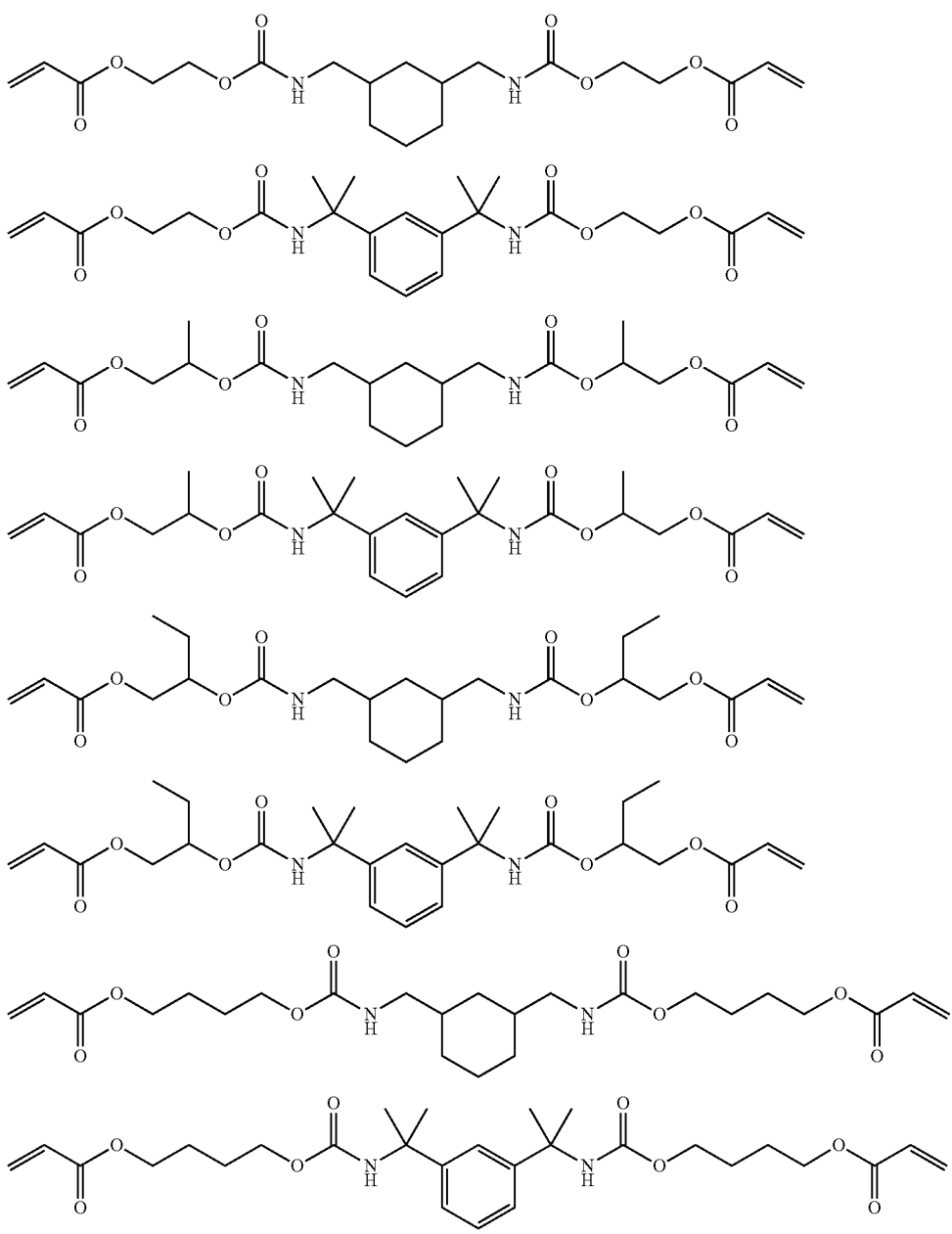
(24c)

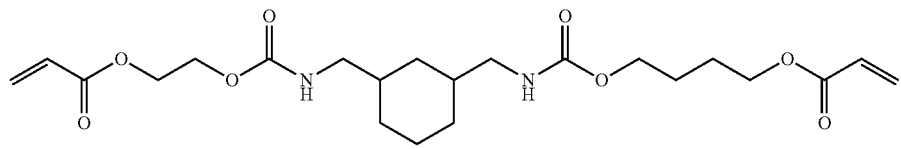
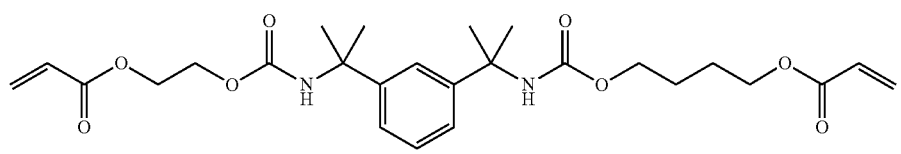
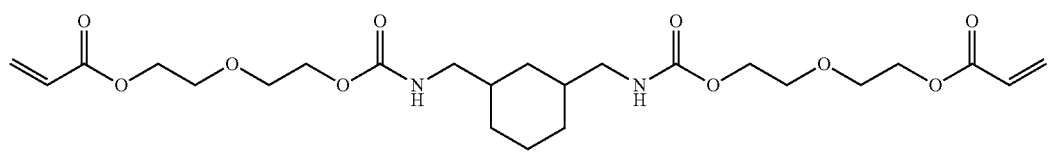
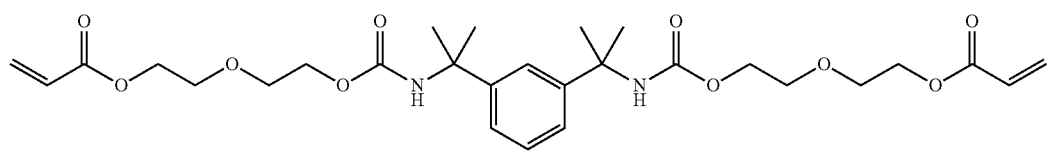
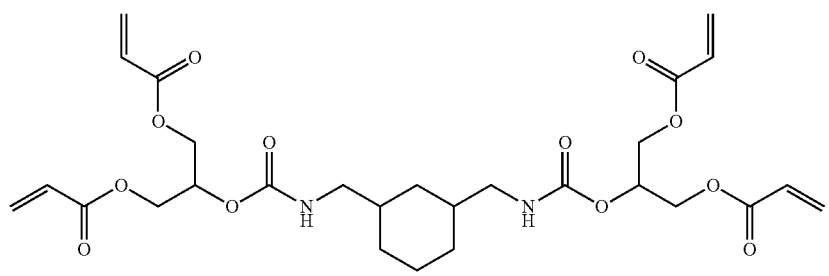
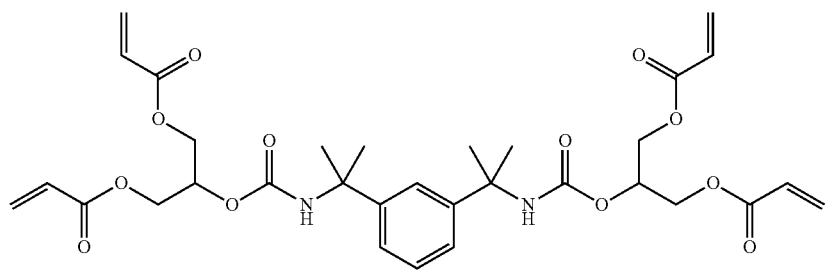
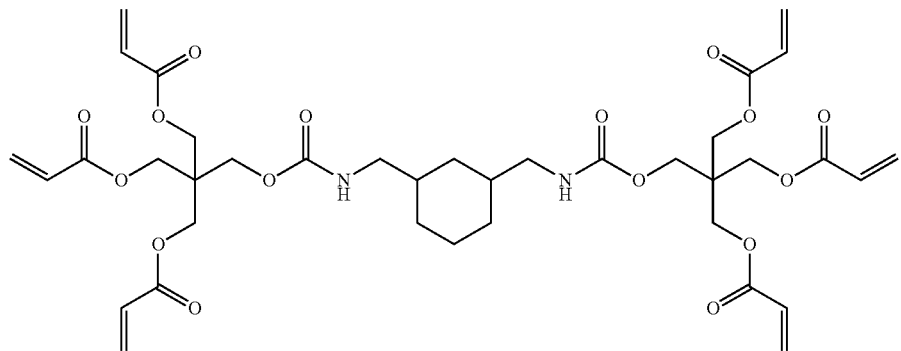

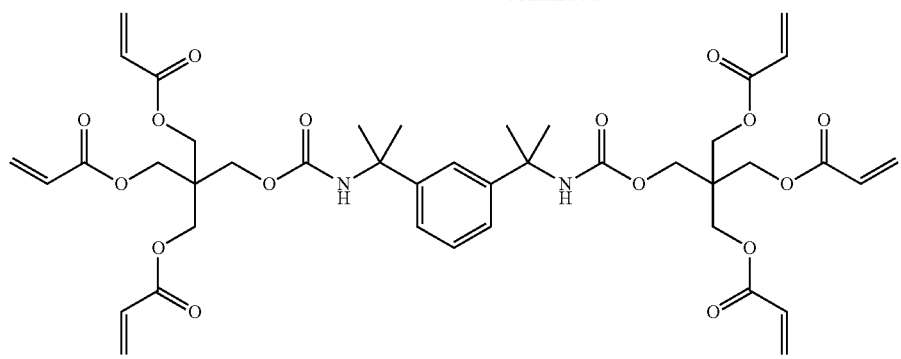
[Chem. 38]
(24d)
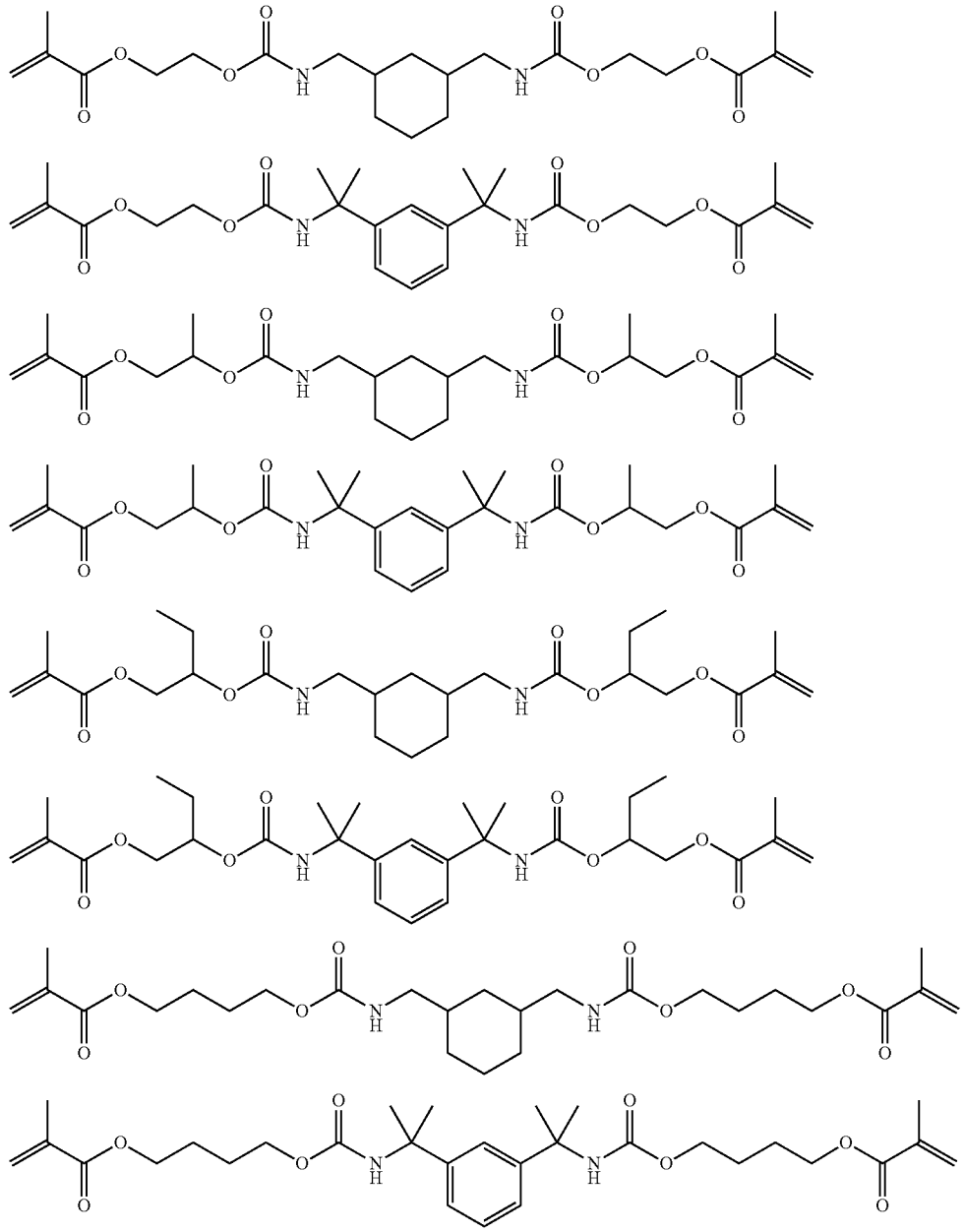

-continued
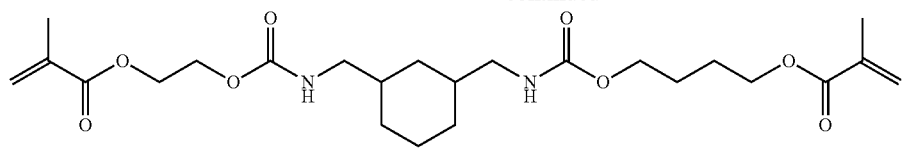
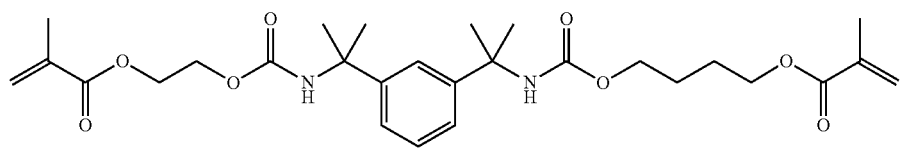
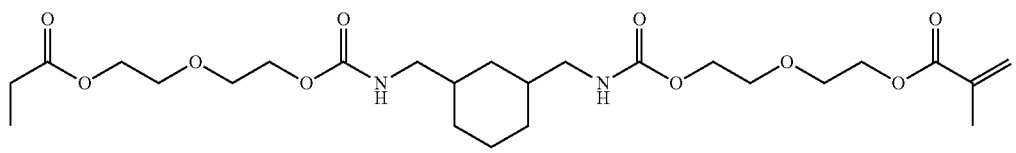
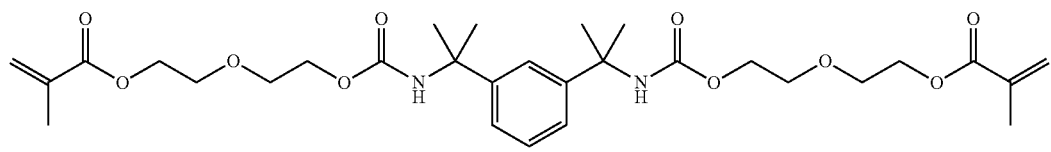
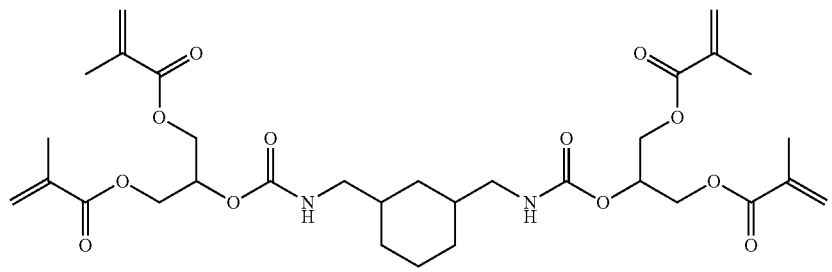
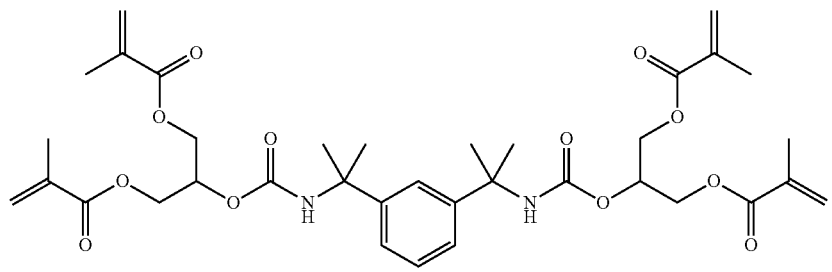
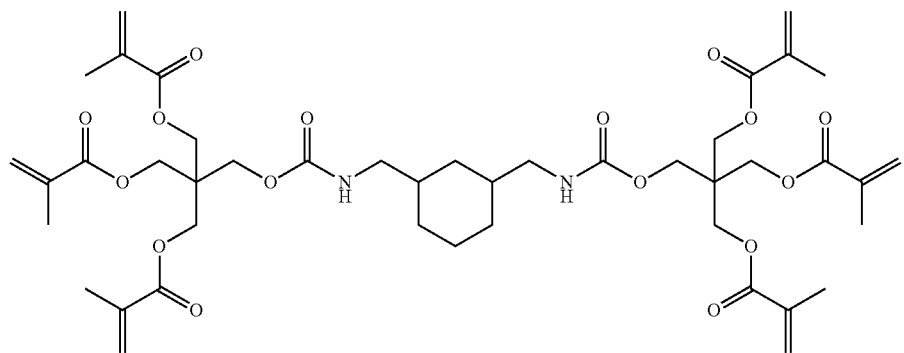

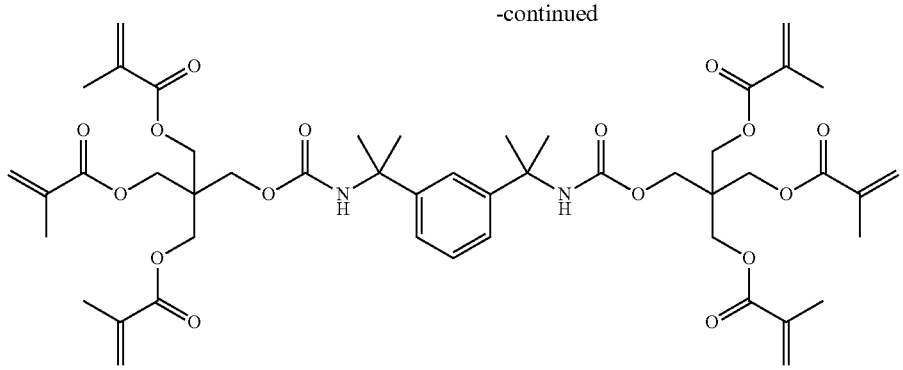
[Chem. 39]
(24e)
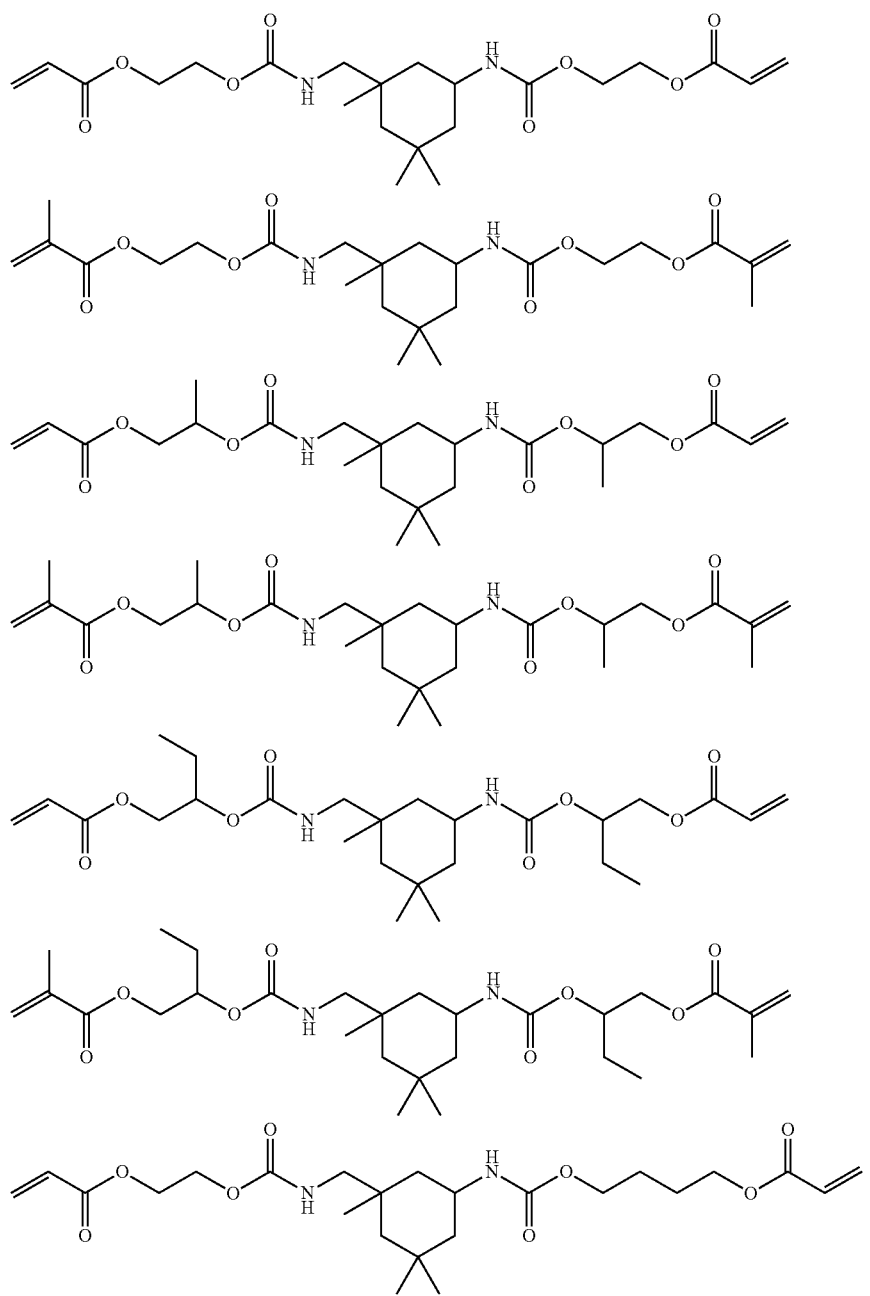

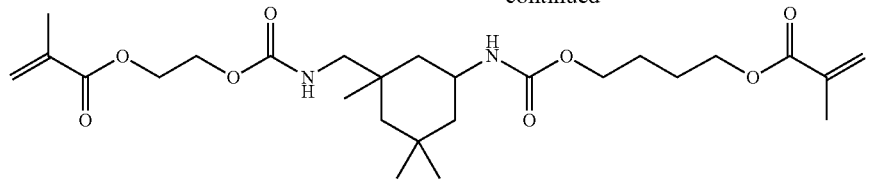
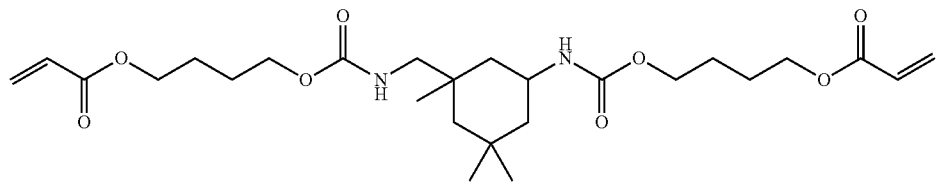
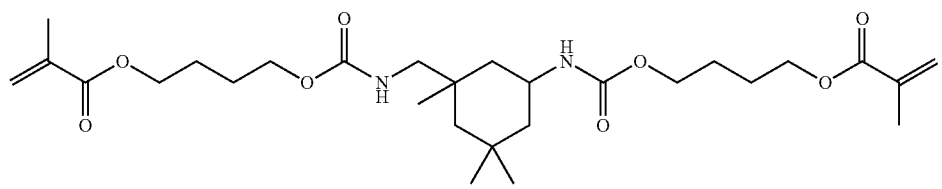
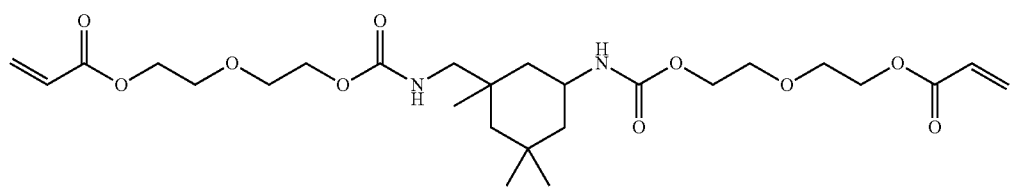
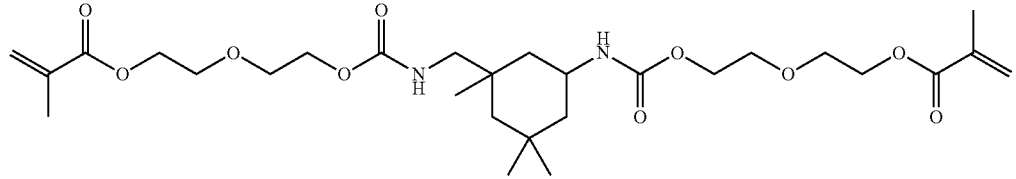
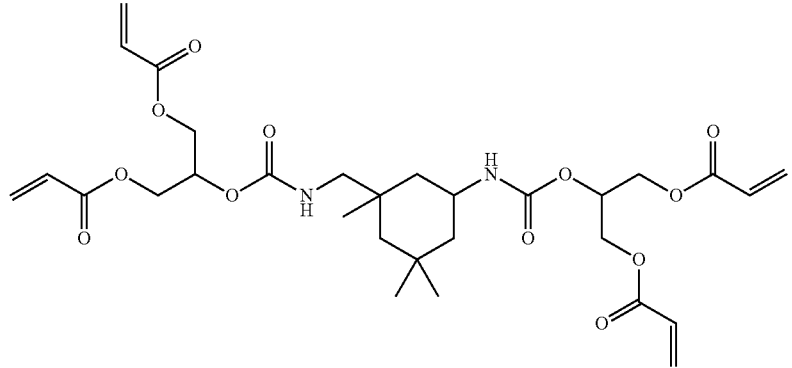
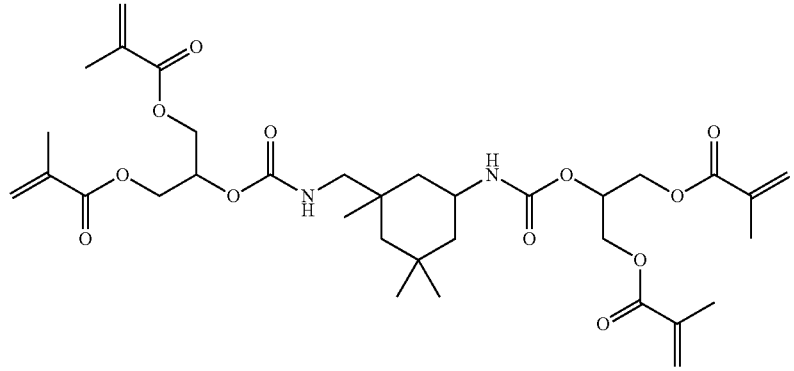

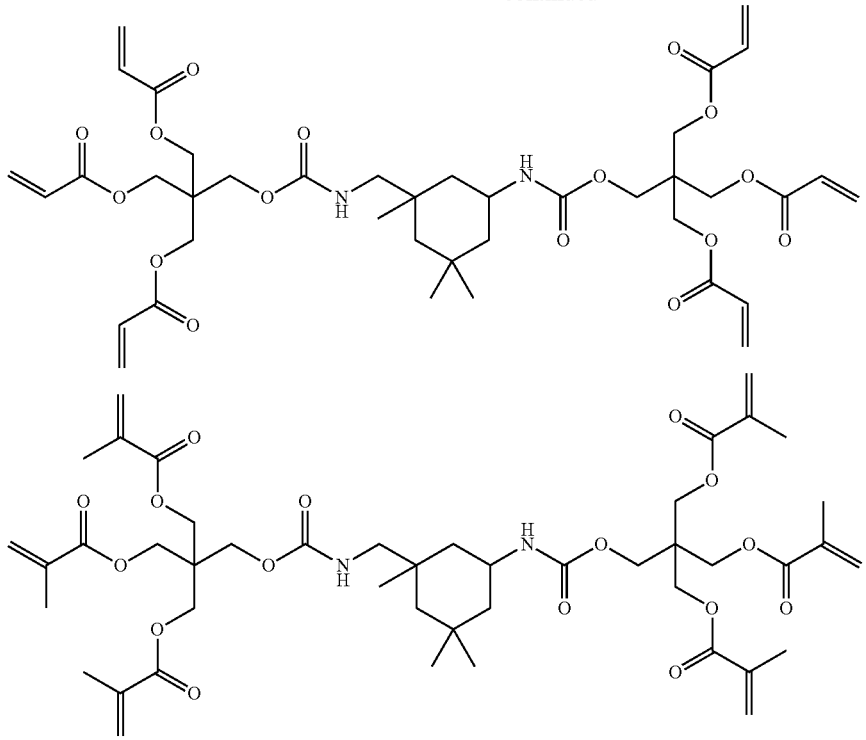

Further, among the monomers represented by the general formula (22), other preferred monomers may be monomers of the general formula (25) below.

[Chem. 40]

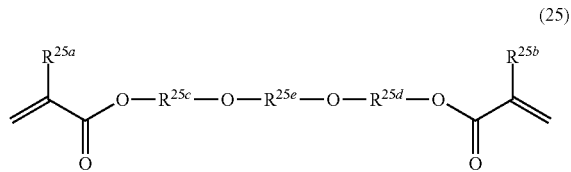

(25)

In the general formula (25), $R^{25a}$ and $R^{25b}$ each represent hydrogen or a methyl group and may be the same as or different from each other; and $R^{25c}$ and $R^{25d}$ each represent a $C_{1-12}$ divalent organic group which may contain oxygen, and may be the same as or different from each other. Examples of the divalent organic groups include hydrocarbon groups, for example, $C_{1-12}$ acyclic hydrocarbon groups such as alkylene groups, and $C_{1-12}$ cyclic hydrocarbon groups such as cycloalkylene groups and arylene groups; and $C_{1-12}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-12}$ cyclic hydrocarbon groups may have acyclic hydrocarbon moieties. Further, the acyclic hydrocarbon moieties present in these groups may be linear or branched. Further, hydrogen atoms present in the organic groups such as the $C_{1-12}$ hydrocarbon groups and the $C_{1-12}$ oxygen-containing hydrocarbon groups may be substituted by acid groups such as carboxyl groups and phosphate groups, functional groups such as hydroxyl groups, amino groups and epoxy groups, and polymerizable groups such as acryloyl groups and methacryloyl groups.

In the general formula (25), $R^{25e}$ represents a $C_{1-20}$ divalent organic group which may contain oxygen. Examples of the divalent organic groups include $C_{1-20}$ hydrocarbon groups such as alkylene groups, cycloalkylene groups and arylene groups; and $C_{1-20}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-20}$ cyclic hydrocarbon groups may have acyclic hydrocarbon moieties. Further, hydrogen atoms present in the organic groups such as the $C_{1-20}$ hydrocarbon groups and the $C_{1-20}$ oxygen-containing hydrocarbon groups may be substituted by acid groups such as carboxyl groups and phosphate groups, and functional groups such as hydroxyl groups, amino groups and epoxy groups.

Examples of the methacryloyl group-containing compounds represented by the general formula (25) include 2,2-bis[4-(3-methacryloyloxy-2-hydroxypropoxy)phenyl]propane (Bis-GMA), ethylene oxide-modified bisphenol A dimethacrylate and propylene oxide-modified bisphenol A dimethacrylate.

Examples of the acryloyl group-containing compounds represented by the general formula (25) include 2,2-bis[4-(3-acryloyloxy-2-hydroxypropoxy)phenyl]propane, ethylene oxide-modified bisphenol A diacrylate and propylene oxide-modified bisphenol A diacrylate.

When the dental material containing the adhesive monomer for dental materials of the invention is used in such an application as dental adhesive materials, the dental material may further contain, as a (meth)acrylate group-containing monomer other than the adhesive monomers for dental materials of the invention, a monomer exhibiting a bonding function. Examples of such adhesive (meth)acrylate group-containing monomers other than the adhesive monomers for dental materials of the invention include monomers having at least one polymerizable group selected from methacryloyl groups and acryloyl groups, and an acidic group (such monomers exclude the adhesive monomer for dental materials of the invention). Examples of the acidic groups include phosphate residues, pyrophosphate residues, thiophosphate residues, carboxylate residues and sulfonate residues.

Examples of the monomers having a methacryloyl group and a phosphate residue (such monomers exclude the adhesive monomer for dental materials of the invention) include 2-methacryloyloxyethyl dihydrogen phosphate, 9-methacryloyloxynonyl dihydrogen phosphate, 10-methacryloyloxydecyl dihydrogen phosphate, 11-methacryloyloxyundecyl dihydrogen phosphate, 20-methacryloyloxyeicosyl dihydrogen phosphate, 1,3-dimethacryloyloxypropyl-2-dihydrogen phosphate, 2-methacryloyloxyethyl phenyl phosphoric acid, 2-methacryloyloxyethyl 2'-bromoethyl phosphoric acid, methacryloyloxyethyl phenyl phosphonate, and acid chlorides of these compounds.

Examples of the monomers having a acryloyl group and a phosphate residue (such monomers exclude the adhesive monomer for dental materials of the invention) include 2-acryloyloxyethyl dihydrogen phosphate, 9-acryloyloxynonyl dihydrogen phosphate, 10-acryloyloxydecyl dihydrogen phosphate, 11-acryloyloxyundecyl dihydrogen phosphate, 20-acryloyloxyeicosyl dihydrogen phosphate, 1,3-diacryloyloxypropyl-2-dihydrogen phosphate, 2-acryloyloxyethyl phenyl phosphoric acid, 2-acryloyloxyethyl 2'-bromoethyl phosphoric acid, acryloyloxyethyl phenyl phosphonate, and acid chlorides of these compounds.

Examples of the monomers having a methacryloyl group and a pyrophosphate residue include di(2-methacryloyloxyethyl) pyrophosphate, and acid chlorides thereof.

Examples of the monomers having an acryloyl group and a pyrophosphate residue include di(2-acryloyloxyethyl) pyrophosphate, and acid chlorides thereof.

Examples of the monomers having a methacryloyl group and a thiophosphate residue include 2-methacryloyloxyethyl dihydrogen dithiophosphate, 10-methacryloyloxydecyl dihydrogen thiophosphate, and acid chlorides of these compounds.

Examples of the monomers having an acryloyl group and a thiophosphate residue include 2-acryloyloxyethyl dihydrogen dithiophosphate, 10-acryloyloxydecyl dihydrogen thiophosphate, and acid chlorides of these compounds.

Examples of the monomers having a methacryloyl group and a carboxylate residue include 4-methacryloyloxyethoxycarbonylphthalic acid, 5-methacryloylaminopentylcarboxylic acid, 11-methacryloyloxy-1,1-undecanedicarboxylic acid, and acid chlorides and acid anhydrides of these compounds.

Examples of the monomers having an acryloyl group and a carboxylate residue include 4-acryloyloxyethoxycarbonylphthalic acid, 5-acryloylaminopentylcarboxylic acid, 11-acryloyloxy-1,1-undecanedicarboxylic acid, and acid chlorides and acid anhydrides of these compounds.

Examples of the monomers having a methacryloyl group and a sulfonate residue include 2-sulfoethyl methacrylate and 2-methacrylamido-2-methylpropanesulfonic acid.

Examples of the monomers having an acryloyl group and a sulfonate residue include 2-sulfoethyl acrylate and 2-acrylamido-2-methylpropanesulfonic acid.

[Polymerization Initiators]

Among the components other than the adhesive monomers for dental materials of the invention in the dental materials of the invention, other components may be polymerization initiators.

The polymerization initiator may be any of general polymerization initiators used in the dental field, and is usually selected in consideration of the polymerizability of the polymerizable monomers, and the polymerization conditions.

In the case of self curing, for example, a redox polymerization initiator that is a combination of an oxidant and a reductant is preferable. When using a redox polymerization initiator, an oxidant and a reductant which are separately packaged need to be mixed with each other immediately before use.

The oxidants are not particularly limited. Examples thereof include organic peroxides such as diacyl peroxides, peroxy esters, dialkyl peroxides, peroxyketals, ketone peroxides and hydroperoxides. Examples of the organic peroxides include such diacyl peroxides as benzoyl peroxide, 2,4-dichlorobenzoyl peroxide and m-toluoyl peroxide; such peroxy esters as t-butyl peroxybenzoate, bis-t-butyl peroxyisophthalate, 2,5-dimethyl-2,5-bis(benzoylperoxy)hexane, t-butyl peroxy-2-ethylhexanoate and t-butyl peroxyisopropyl carbonate; such dialkyl peroxides as dicumyl peroxide, di-t-butyl peroxide and lauroyl peroxide; such peroxyketals as 1,1-bis(t-butylperoxy)-3,3,5-trimethylcyclohexane; such ketone peroxides as methyl ethyl ketone peroxide; and such hydroperoxides as t-butyl hydroperoxide.

The reductants are not particularly limited, but tertiary amines are usually used. Examples of the tertiary amines include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-i-propylaniline, N,N-dimethyl-4-t-butylaniline, N,N-dimethyl-3,5-di-t-butylaniline, N,N-bis(2-hydroxyethyl)-p-toluidine, N,N-bis(2-hydroxyethyl)-3,5-dimethylaniline, N,N-bis(2-hydroxyethyl)-3,4-dimethylaniline, N,N-bis(2-hydroxyethyl)-4-ethylaniline, N,N-bis(2-hydroxyethyl)-4-i-propylaniline, N,N-bis(2-hydroxyethyl)-4-t-butylaniline, N,N-di(2-hydroxyethyl)-3,5-di-i-propylaniline, N,N-bis(2-hydroxyethyl)-3,5-di-t-butylaniline, ethyl 4-dimethylaminobenzoate, n-butoxyethyl 4-dimethylaminobenzoate, (2-methacryloyloxy)ethyl 4-dimethylaminobenzoate, trimethylamine, triethylamine, N-methyldiethanolamine, N-ethyldiethanolamine, N-n-butyldiethanolamine, N-lauryldiethanolamine, triethanolamine, (2-dimethylamino)ethyl methacrylate, N,N-bis(methacryloyloxyethyl)-N-methylamine, N,N-bis(methacryloyloxyethyl)-N-ethylamine, N,N-bis(2-hydroxyethyl)-N-methacryloyloxyethylamine, N,N-bis(methacryloyloxyethyl)-N-(2-hydroxyethyl)amine and tris(methacryloyloxyethyl)amine.

Besides these organic peroxide/amine systems, other redox polymerization initiators such as cumene hydroperoxide/thiourea systems, ascorbic acid/$Cu^{2+}$ salt systems and organic peroxide/amine/sulfinic acid (or sulfinate salt) systems may be used. Further, other polymerization initiators such as tributyl borane and organic sulfinic acids are also suitably used.

In the case of thermal polymerization with heating, it is preferable to use peroxides or azo compounds.

The peroxides are not particularly limited, and examples thereof include benzoyl peroxide, t-butyl hydroperoxide and cumene hydroperoxide. The azo compounds are not particularly limited, and examples thereof include azobisisobutyronitrile.

In the case of photopolymerization with the application of visible lights, suitable initiators are redox initiators such as α-diketones/tertiary amines, α-diketones/aldehydes and α-diketones/mercaptans.

Examples of the photopolymerization initiators, although not particularly limited to, include α-diketones/reductants, ketals/reductants and thioxanthones/reductants. Examples of the α-diketones include camphorquinone, benzil and 2,3-pentanedione. Examples of the ketals include benzyl dimethyl ketal and benzyl diethyl ketal. Examples of the thioxanthones include 2-chlorothioxanthone and 2,4-diethylthioxanthone. Examples of the reductants include tertiary amines such as Michler's ketone, 2-(dimethylamino) ethyl methacrylate, N,N-bis[(meth)acryloyloxyethyl]-N-methylamine, ethyl N,N-dimethylaminobenzoate, butyl 4-dimethylaminobenzoate, butoxyethyl 4-dimethylaminobenzoate, N-methyldiethanolamine, 4-dimethylaminobenzophenone, N,N-bis(2-hydroxyethyl)-p-toluidine and dimethylaminophenanthrol; aldehydes such as citronellal, lauryl aldehyde, phthalic dialdehyde, dimethylaminobenzaldehyde and terephthalaldehyde; and thiol group-containing compounds such as 2-mercaptobenzoxazole, decanethiol, 3-mercaptopropyltrimethoxysilane, 4-mercaptoacetophenone, thiosalicylic acid and thiobenzoic acid. Organic peroxides may be added to these redox systems. That is, α-diketone/organic peroxide/reductant systems may be suitably used.

In the case of photopolymerization with the application of UV lights, some suitable initiators are benzoin alkyl ethers and benzyl dimethyl ketal. Further, such photopolymerization initiators as (bis)acylphosphine oxides are also suitably used.

Of the (bis)acylphosphine oxides, examples of the acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide and benzoyldi-(2,6-dimethylphenyl) phosphonate. Examples of the bisacylphosphine oxides include bis-(2,6-dichlorobenzoyl) phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl) phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide and (2,5,6-trimethylbenzoyl)-2,4,4-trimethylpentylphosphine oxide. These (bis)acylphosphine oxide photopolymerization initiators may be used singly or in combination with various reductants such as amines, aldehydes, mercaptans and sulfinate salts. These reductants may be suitably used also in combination with the visible light photopolymerization initiators described hereinabove.

The polymerization initiators or the photopolymerization initiators may be used singly, or two or more thereof may be used in appropriate combination. The amount thereof is usually in the range of 0.01 to 20 parts by weight, preferably 0.1 to 5 parts by weight per 100 parts by weight of the dental material.

[Fillers]

Among the components other than the adhesive monomers for dental materials of the invention in the dental materials according to the invention, other components may be fillers.

The filler may be any of general fillers used in the dental field. The fillers are usually broadly categorized into organic fillers and inorganic fillers.

Examples of the organic fillers include fine powders of polymethyl methacrylate, polyethyl methacrylate, methyl methacrylate-ethyl methacrylate copolymer, crosslinked polymethyl methacrylate, crosslinked polyethyl methacrylate, ethylene-vinyl acetate copolymer and styrene-butadiene copolymer.

Examples of the inorganic fillers include fine powders of various glasses (based on silicon dioxide and optionally containing oxides of, for example, heavy metals, boron and aluminum), various ceramics, diatomaceous earth, kaolin, clay minerals (such as montmorillonite), activated clay, synthetic zeolite, mica, calcium fluoride, ytterbium fluoride, calcium phosphate, barium sulfate, zirconium dioxide, titanium dioxide and hydroxyapatite. As specific examples of such inorganic fillers, those that are used as X-ray contrast agents are preferable. X-ray contrast agents include barium borosilicate glasses (such as Kimble Raysorb T3000, Schott 8235, Schott GM27884 and Schott GM39923), strontium boroaluminosilicate glasses (such as Raysorb T4000, Schott G018-093 and Schott GM32087), lanthanum glasses (such as Schott GM31684), fluoroaluminosilicate glasses (such as Schott G018-091 and Schott G018-117), and boroaluminosilicate glasses containing zirconium and/or cesium (such as Schott G018-307, G018-308 and G018-310).

Further, an organic inorganic composite filler may be used which is obtained by adding a polymerizable monomer beforehand to the inorganic filler to give a paste, which is then cured by polymerization and crushed.

In a preferred aspect of the dental material, the material contains a microfiller having a particle diameter of not more than 0.1 μm. Such a material is suited as a dental composite resin. Preferred examples of the materials for such micron size fillers include silica (for example, product name: AEROSIL), alumina, zirconia and titania. The addition of such a micron size inorganic filler is advantageous in order for a cured product of the composite resin to achieve high polish and smoothness by being polished.

These fillers may have been surface treated with agents such as silane coupling agents in accordance with purposes. Examples of such surface treating agents include known silane coupling agents, for example, organosilicon compounds such as γ-methacryloxyalkyltrimethoxysilanes (the number of carbon atoms between the methacryloxy group and the silicon atom: 3 to 12), γ-methacryloxyalkyltriethoxysilanes (the number of carbon atoms between the methacryloxy group and the silicon atom: 3 to 12), vinyltrimethoxysilane, vinylethoxysilane and vinyltriacetoxysilane. The surface treating agent is usually used with a concentration in the range of 0.1 to 20 parts by weight, and preferably 1 to 10 parts by weight per 100 parts by weight of the filler.

These fillers may be appropriately added according to the purpose of the dental material. These fillers are appropriately used singly, or two or more thereof are appropriately used in combination. The preferred range of the amount of the filler varies depending on the purpose of the dental material. For example, in the case where the dental material is used as a dental bonding material which is one of dental adhesives, the filler may be added in an amount of about 0.1 to 5 parts by weight per 100 parts by weight of the dental material in order to adjust the viscosity of the dental material. As another example, in the case where the dental material is used as a dental adhesive cement which is one of dental adhesives, the filler may be added in an amount of about 30 to 70 parts by weight per 100 parts by weight of the dental material in order to enhance the mechanical strength and adjust the viscosity. As still another example, in the case where the dental material is used as a dental adhesive composite resin which is one of dental adhesives, the filler may be added in an amount of about 50 to 90 parts by weight per 100 parts by weight of the dental material in order to enhance the mechanical strength and adjust the viscosity.

[Other Components]

The dental material of the invention may appropriately contain components other than the adhesive monomers for dental materials of the invention, the polymerizable monomer other than the adhesive monomers for dental materials of the invention (for example the (meth)acrylate group-containing monomer other than the adhesive monomers for dental materials of the invention, or the epoxy group-containing monomer), the polymerization initiator and the filler in accordance with the purpose. For example, the dental material may contain the aforementioned polymerization inhibitor for enhancing storage stability. To control the color tone, known colorants such as pigments and dyes may be added. Further, known reinforcing materials such as fibers may be added to increase the strength of cured products. In addition, solvents such as acetone, ethanol and water may be present as necessary.

[Ratio of Components]

The amount of the adhesive monomer for dental materials of the invention based on the amount of the dental material is not particularly limited, and is, for example, in the range of 0.1 to 99%. The preferred amount of the adhesive monomer for dental materials may vary depending on the purpose of the dental material. For example, the adhesive monomer for dental materials is added in an amount of 1 to 60 wt % based on the amount of the polymerizable monomer components (the dental hydroxyl group-containing monomer and the polymerizable monomer other than the hydroxyl group-containing monomers (for example the (meth)acrylate group-containing monomer other than the adhesive monomers for dental materials of the invention, or the epoxy group-containing monomer)). In particular, when the dental material is used as a dental adhesive material (bonding material, adhesive resin cement or filling adhesive composite resin), a dental primer or a dental fissure sealant, the amount of the adhesive monomer for dental materials is preferably 1 to 60 wt % based on the amount of the polymerizable monomer components.

(Reverse Mutation Test)

The dental material of the invention is preferably negative in a reverse mutation test. The reverse mutation test (Ames test) is conducted in accordance with the same procedure as that of the above-described reverse mutation test except that the dental material of the invention is used instead of the monomer composition for dental materials according to the invention.

(Cell Test in NRU Method)

The dental material of the invention may allow the relative cell survival rate to fall within a certain range in a cell test in the NRU method using Balb/3T3 cells. The cell test is conducted in accordance with the same procedure as that of the above-described cell test in the NRU method except that the dental material of the invention is used instead of the monomer composition for dental materials according to the invention. Further, the concentration of the test substance of the test material (the adhesive monomer for dental materials of the dental material) in the test solution, and the relative cell growth rate (%) in the dental material may be the same as in the case of the monomer composition for dental materials of the invention.

(Cell Test in WST Method)

The dental material of the invention may allow the relative cell growth rate to fall within a certain range in a cell test in the WST method using Balb/3T3 cells. The cell test is conducted in accordance with the same procedure as that of the above-described cell test in the WST method except that the dental material of the invention is used in place of the monomer composition for dental materials according to the invention. Further, the concentration of the test substance of the test material (the adhesive monomer for dental materials of the dental material) in the test solution, and the relative cell growth rate (%) in the dental material may be the same as in the case of the monomer composition for dental materials according to the invention.

[Method for Producing Dental Material]

A known method may be adopted without limitation as a method for producing the dental material of the invention by mixing the adhesive monomer for dental materials of the invention, the polymerizable monomer other than the adhesive monomers for dental materials of the invention (for example the (meth)acrylate group-containing monomer other than the adhesive monomers for dental materials of the invention, or the epoxy group-containing monomer), the polymerization initiator, the filler, other components and the like.

[Cured Product]

The dental material according to the invention may be cured under appropriate conditions in accordance with the manner in which the polymerization initiator initiates the polymerization. In the case where, for example, the dental material of the invention contains a visible light photopolymerization initiator, a desired cured product may be obtained by shaping the dental material into a prescribed form, and then irradiating the material with visible light for a prescribed time using a known irradiator. The conditions such as intensity and dose may be controlled appropriately in accordance with the curability of the dental material. The cured product that has been cured by the application of light such as visible light may be heat treated under more appropriate conditions, and thereby the mechanical properties of the cured product can be enhanced. Alternatively, in the case where the dental material according to the invention contains a heat polymerization initiator, a desired cured product may be obtained by shaping the dental material into a prescribed form, and then heating the material at an appropriate temperature for an appropriate time.

The thus-obtained cured product of the dental material according to the invention may be used for dental treatment purposes.

[Purposes]

The dental material according to the invention may be suitably used for dental treatment purposes, and may be used as, for example, a filling composite resin, a tooth crowning hard resin, a denture base resin, a denture base liner, an impression material, a dental adhesive material (orthodontic adhesive material, bonding material, adhesive resin cement, filling adhesive composite resin or resin glass ionomer cement), a dental primer, a dental fissure sealant, a CAD/CAM resin block, a temporary crown or an artificial dental material. The adhesive monomer for dental materials according to the invention is particularly suitable for dental adhesive materials and dental primers because the adhesive monomer for dental materials has the function of enhancing adhesive strength with the tooth in dental treatment and a property of increasing the mechanical strength of a cured product of the dental material blended.

While details of the reason why the dental material according to the invention may be particularly suitably used for dental adhesive materials and dental primers are unknown, the adhesive monomer for dental materials according to the invention contains both phosphate groups and (meth)acryloyl groups in the molecule as described above, and are thus supposed to have three functions: tooth surface etching ability derived from phosphoric acid as acidic groups, interaction with the tooth surface via phosphate groups and bonding to a resin matrix via (meth) acryloyl groups. Further, the adhesive monomer for dental materials according to the invention has a carbamate structure in the molecule. The carbamate structure is known to exhibit the effect of imparting high mechanical properties to a so-called urethane polymer due to the coagulation effect of the carbamate structure in the urethane polymer, and in the invention, the carbamate structure present in the molecule of the adhesive monomer for dental materials according to the invention may also have a favorable effect on the strength of the cured dental material according to the invention.

[Usage]

The dental material according to the invention may be used by any known methods generally adopted for dental materials without limitation. When, for example, the dental material according to the invention is used as a bonding material, the dental material is applied to a cavity in the mouth, then dried as necessary, and photocured with a known irradiator as necessary, and a filling composite resin is then packed.

When, for example, the dental material according to the invention is used as an adhesive resin cement, a tooth surface and a prosthesis bonded surface are treated with a primer as necessary, and the dental material according to the invention is then applied to the prosthesis, and the prosthesis is pressure-bonded at a prescribed site in the mouth.

When, for example, the dental material according to the invention is used as a tooth primer, the dental material is applied to a cavity in the mouth, then dried as necessary, and photocured with a known irradiator as necessary, and a prosthesis coated with an adhesive cement is pressure-bonded to the cavity.

When, for example, the dental material according to the invention is used as a filling adhesive composite resin, the dental material is directly packed in a cavity in the mouth, and then photocured with a known irradiator to achieve the purpose.

[Kits]

Kits according to the invention include the above-described dental material. The kits according to the invention include kits in which each component of the dental material is packed as one agent; and kits composed of a plurality of agents such that each component of the dental material is divided into two or more agents and packed in view of a polymerization type, storage stability and the like. The kits according to the invention may include other dental materials which are used in combination with the dental material according to the invention. Such kits are used for bonding materials, adhesive cements, primers, adhesive composite resins and the like.

EXAMPLES

The present invention will be described in further detail based on Examples hereinbelow without limiting the scope of the invention to such Examples.

Production Example 1

A 500-milliliter four-necked flask equipped with a stirring blade, a thermometer and a reflux tube was loaded with 100 g (1.09 mol, the number of moles of OH groups: 3.27 mol) of glycerin (manufactured by Sigma-Aldrich Co. LLC), 0.43 g (1000 ppm based on the total weight of reactants) of dibutyltin dilaurate (manufactured by Wako Pure Chemical Industries, Ltd.) and 0.22 g (500 ppm based on the total weight of reactants) of 2,6-t-butyl-4-methylphenol (manufactured by Wako Pure Chemical Industries, Ltd.), and heated to 55° C. Subsequently, 337 g (2.17 mol, ⅔ equivalents based on the number of moles of OH of glycerin used) of 2-methacryloyloxyethyl isocyanate (KARENZ MOI (registered trademark), manufactured by Showa Denko K.K.) was added dropwise over a period of 30 minutes. Reaction was carried out for 4 hours at a temperature of 80 to 85° C. The infrared absorption spectrum IR was measured (Spectrum Two, manufactured by PerkinElmer), and the result showed that the isocyanate-derived vibration at 2267 cm$^{-1}$ disappeared. A part of the product was taken, the hydroxyl group value thereof was measured in accordance with JIS K 0070, and the result showed that the hydroxyl group value was 138 mg KOH/g. The reaction product was subjected to liquid chromatography mass spectrometry (LC-MS analysis) (1.7 μm ACQUITY UPLC BEH C18 (2.1 mm×10 mm)/ACQUITY UPLC H-Class-SQ Detector 2, manufactured by Nihon Waters K.K.), and the result showed that the mass of [M-H]$^+$ was 403. This result demonstrated that the reaction product had a molecular weight of 402, and this molecular weight was consistent with that of the compound 1. The reaction product was discharged from the reaction vessel to give 417 g of a product containing the compound 1 below.

[Chem. 41]

[Compound 1]

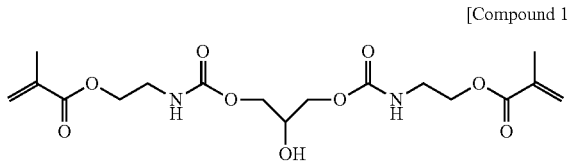

Subsequently, a 300-milliliter four-necked flask equipped with a stirring blade, a thermometer and a reflux tube was loaded with 152 g (hydroxyl group value: 138 mg KOH/g, equivalent of OH: 0.374 mol) of the reaction product containing the compound 1, 450 mL of ultradehydrated methylene chloride (manufactured by Wako Pure Chemical Industries, Ltd.) and 0.093 g (500 ppm based on the total weight of reactants) of 2,6-t-butyl-4-methylphenol. Subsequently, 34.1 g (0.240 mol, P equivalent: 0.480 mol) of diphosphorus pentaoxide (manufactured by Tokyo Chemical Industry Co., Ltd.) was added in three separate portions. Reaction was carried out for 6 hours at a reaction temperature equal to or higher than room temperature and not higher than 30° C. Thereafter, 150 mL of water was slowly added into the apparatus to completely deactivate unreacted diphosphorus pentaoxide at room temperature. The organic layer was extracted, and volatile components were distilled off. The reaction product was discharged from the reaction vessel to give 150 g of a product containing a phosphoric acid ester-containing urethane methacrylic compound of the structural formulas of the compounds 2-1 and 2-2 below. The reaction product was subjected to LC-MS analysis, and the result showed that the masses of [M-H]$^+$ were 483 and 867. This result indicated that the main products had a molecular weight of 482 and a molecular weight of 866, which were consistent with the molecular weight of the compound 2-1 below and the molecular weight of the compound 2-2 below, respectively.

[Chem. 42]

[Compound 2-1]

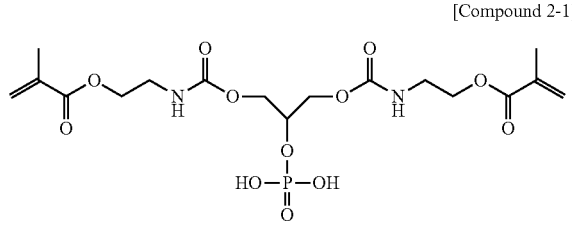

[Compound 2-2]

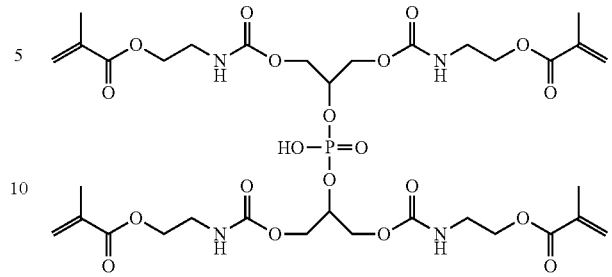

Production Example 2

Except that diglycerin (manufactured by NACALAI TESQUE, INC.) was used in place of the glycerin described in Production Example 1, the same synthesis operation as in Production Example 1 was carried out to give a product containing a compound 3 of the structural formula of the compound 3 below, and a phosphoric acid ester-containing compound 4 of the structural formula of the compound 4 below.

[Chem. 43]

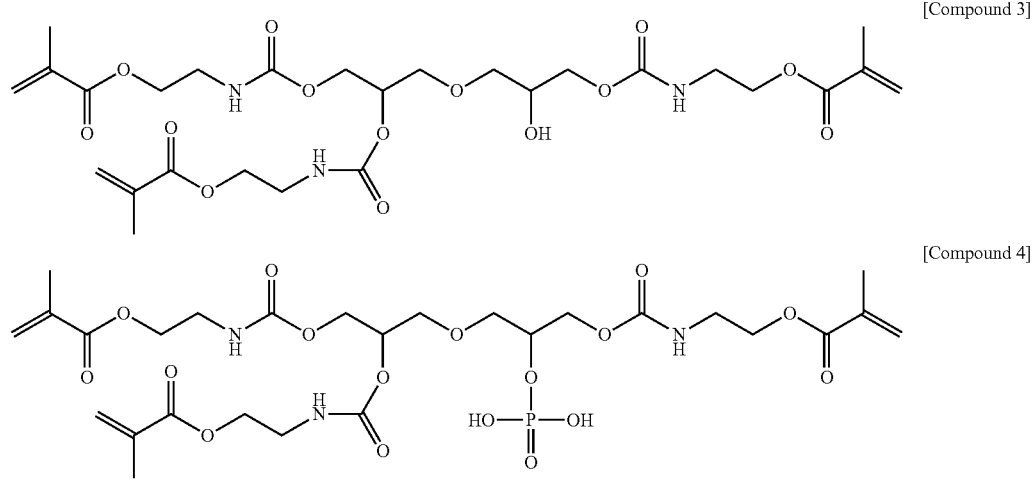

[Compound 3]

[Compound 4]

Production 3

Except that KARENZ MOI-EG (registered trademark) (manufactured by Showa Denko K.K.) containing oxyethylene units in the molecule was used in place of the 2-methacryloyloxyethyl isocyanate (KARENZ MOI (registered trademark)) described in Production Example 1, the same synthesis operation as in Production Example 1 was carried out to give a product containing a compound 5 of the structural formula of the compound 5 below, and a phosphoric acid ester-containing compound 6 of the structural formula of the compound 6 below.

[Chem. 44]

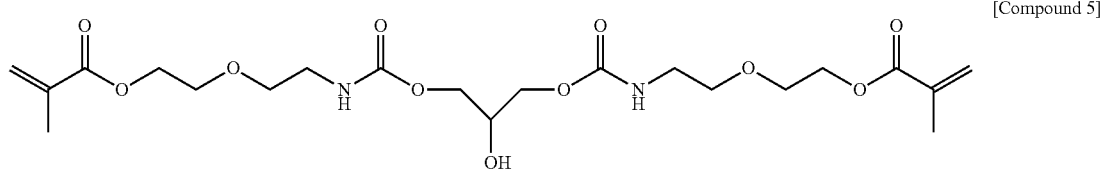

[Compound 5]

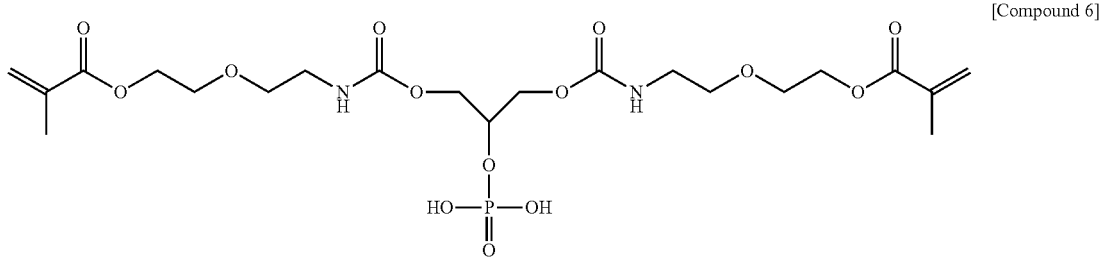

[Compound 6]

Production Example 4

A 300-milliliter four-necked flask equipped with a stirring blade, a thermometer and a reflux tube was loaded with 99.0 g of a polyol 1 (OH group: 1.63 mol) of the structural formula in Table 1 below (ACTCOL (registered trademark), manufactured by Mitsui Chemicals, Inc., average molecular weight: 182, hydroxyl group value: 926 mg KOH/g), 0.27 g (1000 ppm based on the total weight of reactants) of dibutyltin dilaurate and 0.14 g (500 ppm based on the total weight of reactants) of 2,6-t-butyl-4-methylphenol, and heated to 55° C. Subsequently, 171 g (1.10 mol, ⅔ equivalents based on the number of moles of OH of the polyol 1 used) of KARENZ MOI was added dropwise over a period of 20 minutes. Reaction was carried out for 8 hours at a reaction temperature of 80 to 85° C. IR measurement was performed, and the result showed that the isocyanate-derived vibration at 2267 cm$^{-1}$ disappeared. A part of the product was taken, the hydroxyl group value thereof was measured in accordance with JIS K 0070, and the result showed that the hydroxyl group value was 119 mg KOH/g. The reaction product was subjected to LC-MS analysis, and the result showed that the mass of [M-H]$^+$ was 489 and the mass of [M-Na]$^+$ was 511. This result demonstrated that the main product had a molecular weight of 488, and this molecular weight was consistent with that of the compound 1 in which one oxyethylene unit is introduced and a+b+c is equal to 1. The reaction product was discharged from the reaction vessel to give 260 g of a product containing a hydroxyl group-containing monomer represented by the structural formula of the compound 7 below.

[Chem. 45]

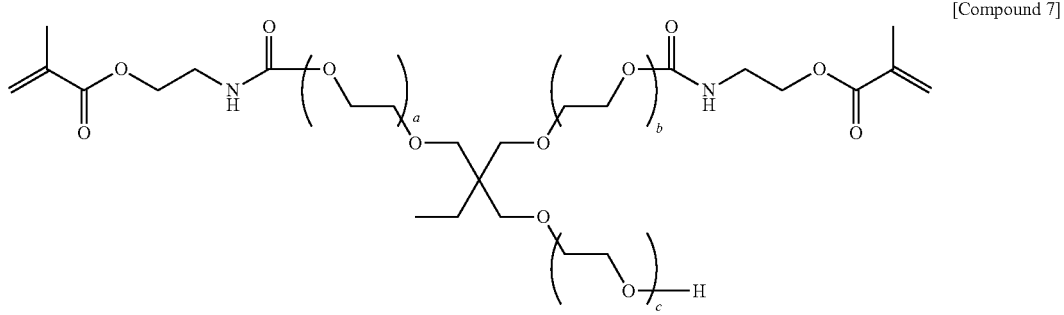

[Compound 7]

Subsequently, the obtained product was reacted with the diphosphorus pentaoxide described in Production Example 1 to give a product containing a phosphoric acid ester-containing compound represented by the structural formula of the compound 8 below.

[Chem. 46]

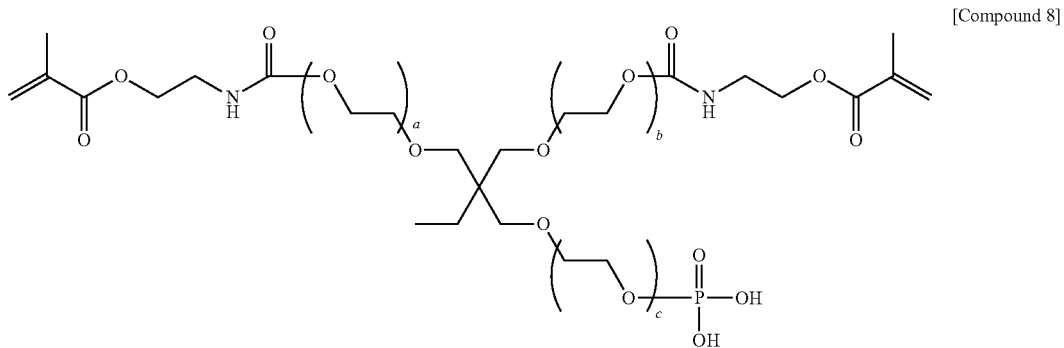

[Compound 8]

Production Examples 5 to 9 and 13

Except that the polyols shown in Table 1 below were used in place of the polyol described in Production Example 4, the same synthesis operation as in Production Example 4 was carried out to give products containing compounds represented by the structural formulas of the compounds 9 to 18, 25 and 26 below.

Production Examples 10 and 11

Except that the polyols shown in Table 1 below was used in place of the polyol described in Production Example 3, the same synthesis operation as in Production Example 4 was carried out to give products containing compounds represented by the structural formulas of the compounds 19 to 22 below.

Production Example 12

Except that ½ equivalents of KARENZ MOI-EG based on the number of moles of OH of the polyol shown in Table 1 below was used in place of KARENZ MOI described in Production Example 4, the same synthesis operation as in Production Example 4 was carried out to give products containing compounds represented by the structural formulas of the compounds 23 and 24 below.

TABLE 1

| Production Examples | Structural formulas of polyol raw materials/hydroxyl group values (mgKOH/g) | Structural formulas of monophosphoric acid ester group-containing compound precursors/hydroxyl group values (mgKOH/g) | Monophosphoric acid ester group-containing compounds |
|---|---|---|---|
| 1 | (diol structure) /92 | Compound 1 /138 | Compound 2 |
| 2 | (triol structure) /476 | Compound 3 /89 | Compound 4 |

TABLE 1-continued

| Production Examples | Structural formulas of polyol raw materials/hydroxyl group values (mgKOH/g) | Structural formulas of monophosphoric acid ester group-containing compound precursors/hydroxyl group values (mgKOH/g) | Monophosphoric acid ester group-containing compounds |
|---|---|---|---|
| 3 | HO–CH₂–C(OH)H–CH₂–OH / 92 | Compound 5 / 109 | Compound 6 |
| 4 | Pentaerythritol ethoxylate structure, average molecular weight 182/926 | Compound 7 / 119 | Compound 8 |

TABLE 1-continued

| Production Examples | Structural formulas of polyol raw materials/hydroxyl group values (mgKOH/g) | Structural formulas of monophosphoric acid ester group-containing compound precursors/hydroxyl group values (mgKOH/g) | Monophosphoric acid ester group-containing compounds |
|---|---|---|---|
| 5 | Average molecular weight 1000/168 | Compound 9/38 | Compound 10 |
| 6 | Average molecular weight 700/251 | Compound 11/61 | Compound 12 |

TABLE 1-continued

| Production Examples | Structural formulas of polyol raw materials/hydroxyl group values (mgKOH/g) | Structural formulas of monophosphoric acid ester group-containing compound precursors/hydroxyl group values (mgKOH/g) | Monophosphoric acid ester group-containing compounds |
|---|---|---|---|
| 7 | Average molecular weight 250/669 | Compound 13/100 | Compound 14 |
| 8 | Average molecular weight 400/396 | Compound 15/84 | Compound 16 |

TABLE 1-continued

| Production Examples | Structural formulas of polyol raw materials/hydroxyl group values (mgKOH/g) | Structural formulas of monophosphoric acid ester group-containing compound precursors/hydroxyl group values (mgKOH/g) | Monophosphoric acid ester group-containing compounds |
|---|---|---|---|
| 9 | 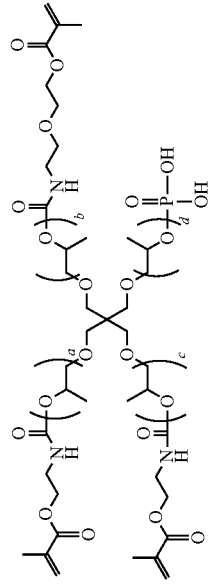 Average molecular weight 500/458 | 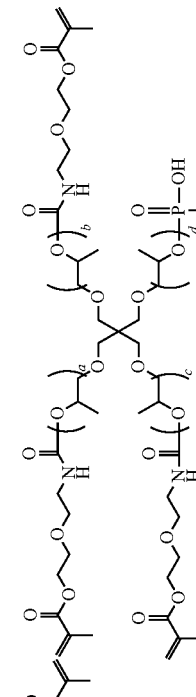 Compound 17/68 | Compound 18 |
| 10 | 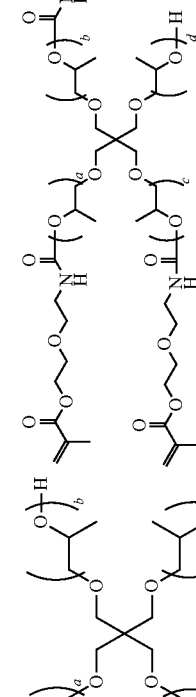 Average molecular weight 500/458 | 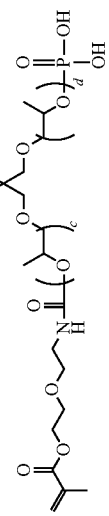 Compound 19/55 | Compound 20 |

TABLE 1-continued

Structural formulas of monophosphoric acid ester group-containing compound precursors/hydroxyl group values (mgKOH/g)

| Production Examples | Structural formulas of polyol raw materials/hydroxyl group values (mgKOH/g) | | Monophosphoric acid ester group-containing compounds |
|---|---|---|---|
| 11 | Average molecular weight 700/251 | Compound 21/50 | Compound 22 |
| 12 | Average molecular weight 500/458 | Compound 23/127 | Compound 24 |
| 13 | /126 | Compound 25/126 | Compound 26 |

Example 1

1.80 g (1.7 mmol) of the compound 2 obtained in Production Example 1, 2.5 g (5.3 mmol) of UDMA (2,2,4-trimethylhexamethylenebis(2-carbamoyloxyethyl) dimethacrylate) and 0.74 g (2.6 mmol) of TEGDMA (triethylene glycol dimethacrylate: NK Ester 3G, manufactured by Shin-Nakamura Chemical Co, Ltd.) were added into a container, and stirred to uniformity at 50° C. to give a polymerizable monomer composition. 0.5 parts by weight of TPO (2,4,6-trimethylbenzoyl-diphenyl-phosphine oxide: IRGACURE TPO, manufactured by BASF SE) was then added to and mixed with 100 parts by weight of the polymerizable monomer composition to give a uniform pasty composition to be used as a dental material. The composition of Example 1 is an example of compositions suitable for evaluation of performance as a resin.

[Bending Strength Test Method]

The composition prepared as described above was packed in a 2×2×25 mm SUS mold, covered with a cover film, and then irradiated with light from a dental visible light irradiator (α Light V, manufactured by J. Morita Tokyo MFG. Corp.) for 3 minutes on each side, namely, for a total of 6 minutes on both sides to cure the composition. The cured product was stored in deionized water at 37° C. for 24 hours, and then subjected to a three-point bending test with a general-purpose tester (Precise Versatile Material Tester 210X, manufactured by INTESCO Co., Ltd.) under conditions in which the distance between supports was 20 mm and the cross head speed was 1.0 mm/min. The results of the bending test of the cured products of the compositions to be used as the dental materials are shown in Table 2.

[Adhesive Strength Test Method]

A bovine lower anterior tooth extracted and kept in a frozen state was thawed by injection of water, and subjected to root amputation and pulp extirpation treatment. This was placed in a plastic cylindrical container having a diameter of 25 mm and a depth of 25 mm, and embedded in an acrylic resin. The surface thereof was wet-polished with #120 and #400 emery papers to expose enamel in a state of being parallel to the lip surface.

Next, compressed air was blown onto the flat surface for about 1 second, the prepared composition was then applied to the enamel flat surface, and compressed air was blown with a low blowing force. This surface was irradiated with light from a visible light irradiator (Translux 2Wave, manufactured by Heraeus Kulzer GmbH) for 20 seconds. Further, a plastic mold having a diameter of 2.38 mm (manufactured by Ultradent Products, Inc.) was then placed thereon, and a dental composite resin (Venus Diamond, manufactured by Heraeus Kulzer GmbH) was packed, irradiated with light from the visible light irradiator for 20 seconds, and thereby cured. Thereafter, the mold was removed to prepare an adhesive sample. The sample was stored in warm water at 37° C. for 24 hours, and a shear load which was parallel to the enamel and in contact with the surface of the bovine tooth was then applied at a cross head speed of 1.0 mm/min using a general-purpose tester (Precise Versatile Material Tester 210X, manufactured by INTESCO Co., Ltd.). The shear adhesive strength was determined from the shear load at the time when the columnar composition formed on the bovine tooth surface was separated from the surface.

The result of the shear test of the dental composition for dental materials is shown in Table 2.

Example 2 to 8

Except that the monophosphoric acid ester group-containing methacrylate compounds 4, 6, 8, 14, 18, 20 and 26 obtained in the above Production Examples were used in place of the compound 2, the same operation as in Example 1 was carried out to prepare polymerizable monomer compositions, and compositions to be used as dental materials. Subsequently, the same tests as in Example 1 were conducted to obtain bending strength and shear test results. The results are shown in Table 2.

Comparative Example 1

Except that MDP (10-methacryloyloxydecyl dihydrogen phosphate) was used in place of the compound 2, the same operation as in Example 1 was carried out to prepare a polymerizable monomer composition, and a composition to be used as a dental material. Subsequently, the same tests as in Example 1 were conducted to obtain bending strength and shear test results. The results are shown in Table 2.

TABLE 2

| | Phosphoric acid ester group-containing methacrylic compounds | Results of shear test on bovine tooth (MPa) | Cured product bending test result | |
|---|---|---|---|---|
| | | | Maximum stress (MPa) | Elastic modulus (GPa) |
| Example 1 | Compound 2 | 17.7 ± 3.4 | 102 | 2.3 |
| Example 2 | Compound 4 | 18.1 ± 4.9 | 102 | 2.4 |
| Example 3 | Compound 6 | 15.2 ± 5.4 | 89 | 2.0 |
| Example 4 | Compound 8 | 17.4 ± 6.7 | 106 | 2.2 |
| Example 5 | Compound 14 | 15.8 ± 2.6 | 95 | 2.1 |
| Example 6 | Compound 18 | 16.5 ± 4.8 | 97 | 2.0 |
| Example 7 | Compound 20 | 17.4 ± 5.7 | 93 | 2.0 |
| Example 8 | Compound 26 | 13.4 ± 1.5 | 93 | 2.1 |
| Comparative Example 2 | MDP | 14.5 ± 2.4 | 85 | 1.7 |

The results in Table 2 reveal that the compositions containing the adhesive monomers for dental materials of the invention have higher adhesive strength with the tooth as compared to the composition containing the conventional adhesive monomer for dental materials, and the cured products of the compositions containing the adhesive monomers for dental materials of the invention have more excellent strength as compared to the cured product of the composition containing the conventional adhesive monomer for dental materials. Thus, use of the adhesive monomer for dental materials of the present invention ensures that a dental adhesive material having high adhesive strength with the tooth and a dental cured product having high strength can be provided.

Example 9

1.2 g (60 parts by weight) of the compound 2 obtained in Production Example 1, 0.6 g (30 parts by weight) of UDMA (2,2,4-trimethylhexamethylenebis(2-carbamoyloxyethyl) dimethacrylate) and 0.2 g (10 parts by weight) of TEGDMA (triethylene glycol dimethacrylate: NK Ester 3G, manufactured by Shin-Nakamura Chemical Co, Ltd.) were added into a container, and stirred to uniformity at 50° C. to give a polymerizable monomer composition. 0.5 parts by weight of TPO (2,4,6-trimethylbenzoyl-diphenyl-phosphine oxide: IRGACURE TPO, manufactured by BASF SE) was then added to and mixed with 100 parts by weight of the polymerizable monomer composition to give a uniform pasty composition to be used as a dental material. The composition of Example 9 is an example of compositions suitable for evaluation of performance as a resin. Except that bovine tooth enamel and bovine tooth dentin were used, the same tests as in Example 1 were conducted to obtain bending strength and shear test results. The results are shown in Table 3.

Examples 10 to 17

Except that the phosphoric acid ester group-containing methacrylates 4, 6, 8, 14, 16, 18, 20 and 26 obtained in the above Production Examples were used in place of the compound 2, the same operation as in Example 9 was carried out to prepare compositions to be used as dental materials. Subsequently, the same tests as in Example 9 were conducted to obtain bending strength and shear test results. The results are shown in Table 3.

Comparative Example 2

Except that MDP (10-methacryloyloxydecyl dihydrogen phosphate) was used in place of the compound 2, the same operation as in Example 9 was carried out to prepare a composition to be used as a dental material. Subsequently, the same test as in Example 9 was conducted to obtain a shear test result. The result is shown in Table 3.

The results in Table 4 have also revealed that the compositions containing the adhesive monomers for dental materials of the invention have higher adhesive strength with the tooth as compared to the composition containing the conventional adhesive monomer for dental materials.

Example 22

0.48 g (8.0 parts by weight) of the compound 2 obtained in Production Example 1, 1.2 g (20 parts by weight) of UDMA (2,2,4-trimethylhexamethylenebis(2-carbamoyloxyethyl) dimethacrylate), 0.6 g (10 parts by weight) of TEGDMA (triethylene glycol dimethacrylate: NK Ester 3G, manufactured by Shin-Nakamura Chemical Co, Ltd.), 0.12 g (2.0 parts by weight) of 4-META (4-methacryloyloxyethyl trimellitic anhydride, manufactured by Wako Pure Chemical Industries, Ltd.), 0.012 g (0.2 parts by weight) of CQ (camphaquinone, manufactured by Wako Pure Chemical Industries, Ltd.) and 0.024 g (0.4 parts by weight) of 2-butoxyethyl 4-(dimethylamino)benzoate (manufactured by Tokyo Chemical Industry Co., Ltd.) were added into a container, and stirred to uniformity at 50° C. to give a mixture. To the mixture was added 3.6 g (59 parts by weight)

TABLE 3

| | Phosphoric acid ester group-containing methacrylic compounds | Results of shear test on bovine tooth | | Cured product bending test result | |
|---|---|---|---|---|---|
| | | Enamel (MPa) | Dentin (MPa) | Maximum stress (MPa) | Elastic modulus (GPa) |
| Example 9 | Compound 2 | 7.9 ± 3.0 | 7.7 ± 2.7 | 92 | 2.2 |
| Example 10 | Compound 4 | 14.0 ± 1.8 | 7.5 ± 2.0 | 88 | 2.3 |
| Example 11 | Compound 6 | 7.1 ± 2.7 | 6.1 ± 2.4 | 66 | 1.3 |
| Example 12 | Compound 8 | 9.0 ± 3.2 | 7.6 ± 1.4 | 68 | 1.4 |
| Example 13 | Compound 14 | 9.6 ± 2.7 | 5.2 ± 2.3 | 75 | 1.6 |
| Example 14 | Compound 16 | 14.3 ± 3.1 | 8.7 ± 2.1 | 51 | 0.94 |
| Example 15 | Compound 18 | 8.3 ± 1.8 | 8.8 ± 2.7 | 79 | 1.8 |
| Example 16 | Compound 20 | 9.4 ± 3.5 | 6.7 ± 1.6 | 62 | 1.2 |
| Example 17 | Compound 26 | 6.9 ± 3.7 | 8.4 ± 1.0 | 81 | 2.0 |
| Comparative Example 2 | MDP | 0.5 ± 1.0 | 0.5 ± 0.6 | 22 | 0.32 |

Examples 18 to 21

Except that the phosphoric acid ester group-containing methacrylates 10, 12, 22 and 24 obtained in the above Production Examples were used in place of the compound 2, the same operation as in Example 9 was carried out to prepare compositions to be used as dental materials. Subsequently, the same test as in Example 9 was conducted to obtain a shear test result. The result is shown in Table 4.

TABLE 4

| | Phosphoric acid ester group-containing methacrylic compounds | Results of shear test on bovine tooth | |
|---|---|---|---|
| | | Enamel (MPa) | Dentin (MPa) |
| Example 18 | Compound 10 | 4.6 ± 2.5 | 6.9 ± 1.7 |
| Example 19 | Compound 12 | 8.9 ± 1.5 | 7.7 ± 1.6 |
| Example 20 | Compound 22 | 3.2 ± 1.6 | 4.5 ± 1.2 |
| Example 21 | Compound 24 | 8.7 ± 1.6 | 3.0 ± 0.9 |
| Comparative Example 2 | MDP | 0.5 ± 1.0 | 0.5 ± 0.6 | of a barium aluminum borosilicate glass filler (GM 27884, particle diameter: 1.5 μm, 1.6% silane-treated product, manufactured by NEC SCHOTT Components Corporation), and the resulting mixture was mixed to give a uniform pasty composition to be used as a dental material. The composition of Example 22 is an example of compositions suitable for evaluation of performance as a resin. Except that bovine tooth dentin was used, a plastic mold was placed on a dentin flat surface blown with compressed air, the composition was packed in two portions, and a dental composite resin (Venus Diamond) was not used, the same tests as in Example 1 were conducted to obtain bending test and shear test results. The results are shown in Table 4.

Comparative Example 3

Except that MDP (10-methacryloyloxydecyl dihydrogen phosphate) was used in place of the compound 2, the same operation as in Example 22 was carried out to prepare a composition to be used as a dental material. Subsequently, the same tests as in Example 22 were conducted to obtain bending test and shear test results. The results are shown in Table 5.

TABLE 5

| | Phosphoric acid ester group-containing methacrylic compounds | Results of shear test on bovine tooth Dentin (MPa) | Cured product bending test result Elastic modulus (GPa) |
|---|---|---|---|
| Example 22 | Compound 2 | 20.2 ± 4.0 | 6.5 |
| Comparative Example 3 | MDP | 10.4 ± 2.8 | 5.7 |

Example 23

1.0 g (4.7 parts by weight) of the compound 2 obtained in Production Example 1, 6.0 g (28 parts by weight) of Bis-GMA (bisphenol A diglycidyl methacrylate, manufactured by Shin-Nakamura Chemical Co, Ltd.), 6.0 g (28 parts by weight) of HEMA (Acryester HO (registered trademark), manufactured by Mitsubishi Rayon Co., Ltd.), 0.020 g (0.94 parts by weight) of TPO (2,4,6-trimethylbenzoyl-diphenyl-phosphine oxide: IRGACURE TPO, manufactured by BASF SE), 0.40 g (1.9 parts by weight) of CQ (camphaquinone, manufactured by Wako Pure Chemical Industries, Ltd.), 0.20 g (0.94 parts by weight) of ethyl 4-(dimethylamino)benzoate (manufactured by Wako Pure Chemical Industries, Ltd.), 0.20 g (0.94 parts by weight) of p-tolyldiethanolamine (manufactured by Tokyo Chemical Industry Co., Ltd.), 3.0 g (14 parts by weight) of BHT (dibutylhydroxytoluene: manufactured by Wako Pure Chemical Industries, Ltd.), 3.0 g (14 parts by weight) of ethanol (ultradehydrated: manufactured by Wako Pure Chemical Industries, Ltd.) and 3.0 g (14 parts by weight) of distilled water were added into a container, and stirred to uniformity at 50° C. to give a mixture. To the mixture was added 1.2 g (5.7 parts by weight) of a barium aluminum borosilicate glass filler (GM 27884, particle diameter: 1.5 μm, 1.6% silane-treated product, manufactured by NEC SCHOTT Components Corporation), and the resulting mixture was mixed to give a uniform liquid composition to be used as a dental material. The composition of Example 22 is an example of compositions suitable for evaluation of performance as a resin. Except that bovine tooth dentin was used, and after application of the composition, compressed air was blown with a low blowing force to remove the solvent, the same test as in Example 1 was conducted to obtain a shear test result. The result is shown in Table 6.

Comparative Example 4

Except that MDP (10-methacryloyloxydecyl dihydrogen phosphate) was used in place of the compound 2, the same operation as in Example 23 was carried out to prepare a composition to be used as a dental material. Subsequently, the same test as in Example 23 was conducted to obtain a shear test result. The result is shown in Table 6.

TABLE 6

| | Phosphoric acid ester group-containing methacrylic compounds | Results of shear test on bovine tooth Dentin (MPa) |
|---|---|---|
| Example 23 | Compound 2 | 28.5 ± 04.9 |
| Comparative Example 4 | MDP | 19.4 ± 5.8 |

The results in Tables 5 and 6 have also revealed that the compositions containing the adhesive monomers for dental materials of the invention have higher adhesive strength with the tooth as compared to the compositions containing the conventional adhesive monomers for dental materials, and the cured products of the compositions containing the adhesive monomers for dental materials of the invention have more sufficient mechanical strength as compared to the cured products of the compositions containing the conventional adhesive monomers for dental materials.

The invention claimed is:

1. An adhesive monomer for dental materials comprising a compound represented by the general formula (1) below, in which the core (X) below and the terminal group (Y1) below are bonded to each other directly or via the linking group (Z) below:

$$X(Y1)_{n^{1a}}(Z-Y1)_{n^{1b}} \quad (1)$$

wherein in the general formula (1), $n^{1a}$ represents the number of terminal groups (Y1) directly bonded to the core (X), $n^{1b}$ represents the number of terminal groups (Y1) bonded to the core (X) via the linking group (Z), and the sum of $n^{1a}$ and $n^{1b}$ is equal to the valence of the core (X);

the core (X) is a $C_{1-200}$ polyvalent organic group having a valence of 3 to 12 containing an oxygen atom or a nitrogen atom in which an atom bonded to the terminal group (Y1) or the linking group (Z) is the oxygen atom or the nitrogen atom;

the terminal group (Y1) is a phosphorus-containing group represented by the general formula (2) below, a phosphorus-containing group represented by the general formula (3) below, a (meth)acryloyl group-containing group (Y2) represented by the general formula (4) below, a (meth)acryloyl group, a $C_{1-20}$ hydrocarbon group or a hydrogen atom, and a plurality of terminal groups (Y1) may be the same as or different from each other, with the proviso that among all the terminal groups (Y1) in the compound represented by the general formula (1), one or more terminal groups are phosphorus-containing groups represented by the general formula (2) below or phosphorus-containing groups represented by the general formula (3) below, and one or more terminal groups are (meth)acryloyl group-containing groups (Y2); and the linking group (Z) is a divalent group represented by the general formula (5) below, and when the compound represented by the general formula (1) contains a plurality of linking groups (Z), the linking groups (Z) may be the same as or different from each other;

(2)

(3)

wherein in the general formula (3), one end of the group is bonded to the core (X) or the linking group (Z), and the other end of the group is bonded to the core (X) or the linking group (Z) present in another compound represented by the general formula (1);

(4)

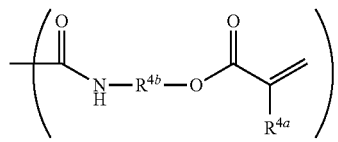

wherein in the general formula (4), $R^{4a}$ represents a hydrogen atom or a methyl group, $R^{4b}$ represents a $C_{2-6}$ linear alkylene group or a $C_{2-6}$ linear oxyalkylene group, and the linear alkylene group or the linear oxyalkylene group is optionally substituted with a $C_{1-6}$ alkyl group or a (meth)acryloyloxymethylene group in place of a hydrogen atom; and (5)

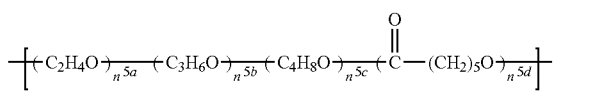

wherein in the general formula (5), $n^{5a}$, $n^{5b}$, $n^{5c}$ and $n^{5d}$ represent the unit numbers of respective repeating units, and are each 0 to 100, the sum of $n^{5a}$, $n^{5b}$, $n^{5c}$ and $n^{5d}$ is 1 to 100, the left end of the group is bonded to the core (X), and the right end of the group is bonded to the terminal group (Y1).

2. The adhesive monomer for dental materials according to claim 1, wherein the terminal group (Y1) is a phosphorus-containing group represented by the general formula (2), a phosphorus-containing group represented by the general formula (3), a (meth)acryloyl group-containing group (Y2) represented by the general formula (4), or a hydrogen atom.

3. The adhesive monomer for dental materials according to claim 1, wherein the terminal group (Y1) is a phosphorus-containing group represented by the general formula (2), a phosphorus-containing group represented by the general formula (3), or a (meth)acryloyl group-containing group (Y2) represented by the general formula (4).

4. The adhesive monomer for dental materials according to claim 1, wherein in the linking group (Z) $n^{5a}$, $n^{5b}$, $n^{5c}$ and $n^{5d}$ are each 0 to 20, and the sum of $n^{5a}$, $n^{5b}$, $n^{5c}$ and $n^{5d}$ is 1 to 20.

5. The adhesive monomer for dental materials according to claim 1, wherein the linking group (Z) is a divalent group represented by the general formula (6) below:

(6)

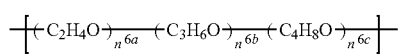

wherein in the general formula (6), $n^{6a}$, $n^{6b}$ and $n^{6c}$ represent the unit numbers of respective repeating units, and are each 0 to 20, the sum of $n^{6a}$, $n^{6b}$ and $n^{6c}$ is 1 to 20, the left end of the group is bonded to the core (X), and the right end of the group is bonded to the terminal group (Y1).

6. The adhesive monomer for dental materials according to claim 1, wherein the linking group (Z) is a divalent group represented by the general formula (7) below:

(7)

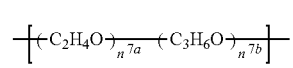

wherein in the general formula (7), $n^{7a}$ and $n^{7b}$ represent the unit numbers of respective repeating units, and are each 0 to 20, the sum of $n^{7a}$ and $n^{7b}$ is 1 to 20, the left end of the group is bonded to the core (X), and the right end of the group is bonded to the terminal group (Y1).

7. The adhesive monomer for dental materials according to claim 1, wherein the core (X) is at least one selected from the group consisting of groups represented by the general formulas (8a) to (8j) below:

(8a)

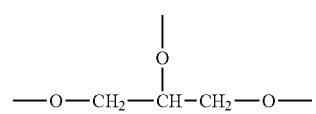

(8b)

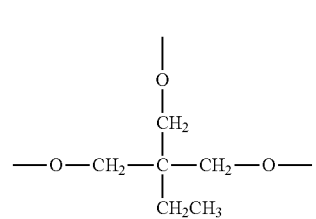

(8c)

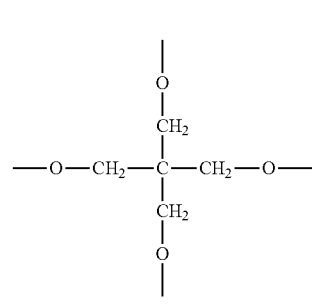

(8d)

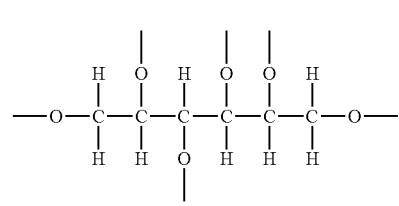

(8e)

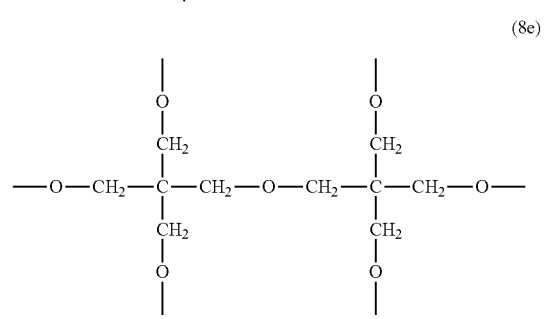

-continued (8f)

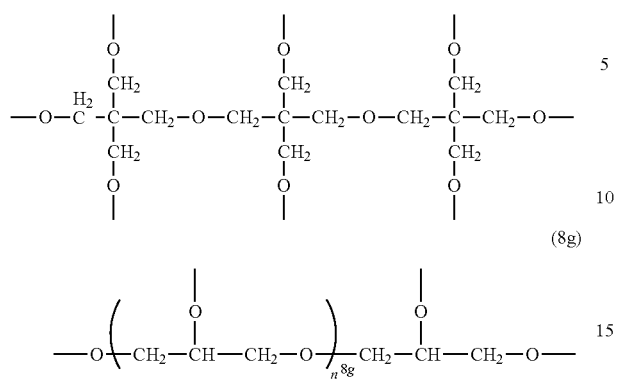

(8g)

wherein in the general formula (8g), $n^{8g}$ is an integer of 1 to 40

(8h)

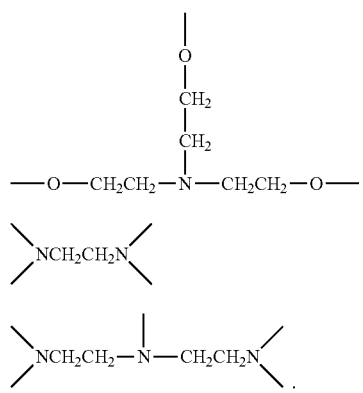

(8i)

(8j)

8. The adhesive monomer for dental materials according to claim 1, wherein the (meth)acryloyl group-containing group (Y2) is at least one selected from the group consisting of groups represented by the general formulas (4a) to (4f) below:

(4a)

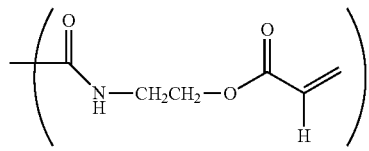

-continued (4b)

(4c)

(4d)

(4e)

(4f)

9. A monomer composition for dental materials comprising the adhesive monomer for dental materials according to claim 1.

10. The monomer composition for dental materials according to claim 9, wherein the monomer composition for dental materials is negative in a reverse mutation test.

11. A dental material comprising the adhesive monomer for dental materials according to claim 1.

12. The dental material according to claim 11, wherein the dental material is negative in a reverse mutation test.

13. A kit comprising the dental material according to claim 11.

* * * * *